US006248063B1

(12) United States Patent
Barnhill et al.

(10) Patent No.: US 6,248,063 B1
(45) Date of Patent: Jun. 19, 2001

(54) COMPUTER ASSISTED METHODS FOR DIAGNOSING DISEASES

(75) Inventors: Stephen D. Barnhill, Savannah, GA (US); Zhen Zhang, Mt. Pleasant, SC (US)

(73) Assignee: Horus Therapeutics, Inc., Hilton Head, SC (US)

(*) Notice: Subject to any disclaimer, the term of this patent is extended or adjusted under 35 U.S.C. 154(b) by 0 days.

(21) Appl. No.: 08/997,092

(22) Filed: Dec. 22, 1997

Related U.S. Application Data

(63) Continuation of application No. 08/642,848, filed on May 3, 1996, now Pat. No. 5,769,074, which is a continuation-in-part of application No. 08/323,446, filed on Oct. 13, 1994, now abandoned

(60) Provisional application No. 60/001,425, filed on Jul. 25, 1995.

(51) Int. Cl.[7] .................................................. A01B 5/00
(52) U.S. Cl. .......................... 600/300; 706/21; 128/924
(58) Field of Search .................. 600/300; 128/920–924; 395/22; 706/16, 21–22, 25, 31

(56) References Cited

U.S. PATENT DOCUMENTS

| | | |
|---|---|---|
| 4,290,114 | 9/1981 | Sinay . |
| 4,635,643 | 1/1987 | Brown . |
| 4,740,364 | 4/1988 | Hodgen . |
| 4,857,456 | 8/1989 | Urist . |
| 4,862,897 | 9/1989 | Eisenberg et al. . |
| 4,965,725 | 10/1990 | Rutenberg . |
| 5,092,343 | 3/1992 | Spitzer et al. . |
| 5,130,936 | 7/1992 | Sheppard et al. . |
| 5,251,626 | 10/1993 | Nickolls et al. . |
| 5,260,871 | 11/1993 | Goldberg . |
| 5,280,792 | 1/1994 | Leong et al. . |
| 5,285,793 | 2/1994 | Slovut et al. . |
| 5,312,443 | 5/1994 | Adams et al. . |
| 5,463,548 | 10/1995 | Asada et al. . |
| 5,590,665 | * 1/1997 | Kanai .................................... 128/898 |
| 5,790,761 | * 8/1998 | Heseltine et al. ........................ 395/22 |

FOREIGN PATENT DOCUMENTS

93/12255    6/1993   (WO) .

OTHER PUBLICATIONS

Barnhill et al., "Osteoporosis: A Possible Autoimmune Etiology", Abstract of the 80th Meeting of the Association of Clinical Scientists, Charleston, SC (May 14–17, 1987).
Brochure Dianon Systems—"Physician Participation Program Oncosite™ Biomarker Tests" 1986, Rev. (Jun. 1992).
Gene Bylinsky, "Computers That Learn by Doing", *Fortune*, vol. 96 (Sep. 6, 1993).
Harvey E. Dytch, et al., "Artificial Neural Networks and Their Use in Quantitative Pathology", *Ana & Quant. Cyt. &m Hist.*, vol. 12, No. 6, pp. 379–393 (Dec. 1990).
Jack M. Fletcher, et al., "Linear Discriminant Function Analysis in Neurophysiological Research: Some Uses and Abuses", *Cortex*, vol. 14, pp. 564–577 (1978).
Steven J. Fraleigh, "Fuzzy Logic and Neutral Networks: Practical Tools for Process Management", PCAI, pp. 17 & 18 (May/Jun. 1994).

(List continued on next page.)

*Primary Examiner*—Francis J. Jaworski
(74) *Attorney, Agent, or Firm*—Jones & Askew, LLP

(57) ABSTRACT

The simultaneous multi access reasoning technology system of the present invention utilizes both existing knowledge and implicit information that can be numerically extracted from training data to provide a method and apparatus for diagnosing disease and treating a patient. This technology further comprises a system for receiving patient data from another location, analyzing the data in a trained neural network, producing a diagnostic value, and optionally transmitting the diagnostic value to another location.

39 Claims, 70 Drawing Sheets

OTHER PUBLICATIONS

John H. Frenster, "Neural Networks for Pattern Recognition in Medical Diagnosis", Ann. Intl. Conf. *IEEE Eng. Med. & Bio. Soc.,* vol. 12, No. 3, pp. 1423–1424 (1990).

James W. Furlong, et al., "Neural Network Analysis of Serial Cardiac Enzyme Data, A Clinical Application of Artificial Machine Intelligence", *Clin. Chem.,* vol. 96, No. 1, pp. 134–141 (1991).

Griffiths, et al., "Separation and Identification of Alkaline Phosphatase Isoenzymes and Isoforms in Serum of Healthy Persons by Isoelectric Focusing", *Clinical Chemistry, American Assoc. for Clinc. Chem.,* vol. 33, No. 12, pp. 2171–2177, (Dec. 1987).

S.C. Henzen–Logmans, et al., "Use of statistical evaluation of antigen profiles in differential diagnosis between colonic and ovarian adenocarcinomas", *J. Clin. Pathol,* vol. 41, pp. 644–649 (1988).

Allen Jost, "Neural Networks", *Credit World,* pp. 26–33, (Mar./Apr. 1993).

H.J. Kappen, et al., "Neural network analysis to predict treatment outcome", *Annals of Oncology,* vol. 4, (1993).

Hiroshi Kobayashi, et al., "Field Trial for the Early Detection of Patients with Ovarian Cancer Patients by the Statistical Analysis Using Malahonobis Generalized Distance", *ACTA Obst. Gynaec.,* JPN, vol. 44, No. 2, pp. 171–180 (1992).

Philip S. Maclin, et al., "How to improve a neural network for early detection of hepatic cancer", *Cancer Letters,* vol. 77, pp. 95–101 (1994).

Benoit H. Mulsant, M.D., "A Neural Network as an Approach to Clinical Diagnosis", *Neural Modeling,* vol. 7, No. 1, pp. 25–36 (1990).

Steven Piantadosi, et al., "Neural Network vs. Logistic regression for Prediction of Pathological State or Disease Progression Among Men with Clinically Localized Prostate Cancer", Abstract#750.

Peter M. Ravdin, et al, "A practical application of neural network analysis for predicting outcome of individual breast cancer patients", *Breast Cancer Research & Treatment,* vol. 22, pp. 285–293 (1992).

Gilbert Reibnegger, et al., "Neural networks as a tool for utilizing laboratory information: Comparison with linear discriminate analysis and with classification and regression trees", *Proc. Natl. Acad. Sci. USA,* vol. 88, pp. 11426–11430 (Dec. 1991).

"Resolve®—ALP—Instructions for Use," Isolanb, Inc., Revised: May 18, 1988).

David E. Rumelhart, et al. "Learning representations by back–propagating errors", *Nature,* vol. 323, No. 9, pp. 533–536 (1986).

Peter K. Sharpe, et al., "Artificial Neural Networks in Diagnosis of Thyroid Function form in Vitro Laboratory tests," *Clin. Chem.,* No. 11, pp. 2248–2253 (1993).

Solbert, "Establishment and Use of Reference Values", *Textbook of Clinical Chemistry* (Tietz, ed.) W.B. Saunders, Philadelphia, pp. 356 and 380–382 (1986).

K.D. Swenerton, M.D., et al., "Ovarian Carcinoma: A Multivariate Analysis of Prognostic Factors", *Obst. & Gyn.,* vol. 65, No. 2, pp. 264–269 (Feb. 1985).

M. Wann, et al. "The Influence of Training Sets on Generalization in Feed–Forward Neural Networks", *In Proc. Int. Joint Conf. Neural Network* (San Diego), Col. III, pp. 137–142 (1990).

Peter Wilding, et al., "Application of back propogation neural networks to diagnosis of breast and ovarian cancer", *Cancer Letters,* vol. 77, pp. 145–153 (1994).

Wilkes et al, "The Efficacy of Measuring Bone Mineral Density in Asymptomatic Women: A Preliminary Report," *Journal of the Medical Association of Georgia,* 57–58, (Jan. 1988).

Hiromitsu Yabushita et al., "Combination Assay of CA125, TPA, IAP, CEA and Ferritin in Serum for Ovarian Cancer", *Gyn. Oncol.,* vol. 29, pp. 66–75 (1988).

Young, et al., "Specimen Collection and Processing; Sources of Biological Variation", *Textbook of Clinical Chemistry,* (Tietz, ed.) W.B. Saudners, Philadelphia, pp. 480 and 508–512, (1986).

Yuzbeng Wu, et al., "Artificial Neural Networks in Mammography: Application to Decision Making in the Diagnosis of Breast Cancer", *Radiology,* vol. 187, No. 1, pp. 81–87 (1993).

Astion et al., 1992, Application of neural networks to the interpretation of laboratory data in cancer diagnosis. *Clin. Chem.* vol. 38, No. 1 pp. 34–38 (1992).

Bassoe, Cark–F., "Automated Diagnoses from Clinical Narratives: A Medical System Based on Computerized Medical Records, Natural Language Processing, and Neural Network Technology", *Neural Networks,* vol. 8. No. 2. pp. 313–319, (1995).

Moneta, C., Parodi, G., Rovetta, S., and Zunini, R., "Automated Diagnosis and Disease Characterization using Neural Network Analysis", *IEEE International Conference on Systems, Man and Cybernetics,* vol. 1, pp. 123–128, (1992).

Mazess, R., et al., "Bone Density of the Radius, Spine, and Proximal Femur in Osteoporosis," *J. of Bone and Mineral Research,* vol. 3, pp. 13–18, (1988).

Riggs, B.L., et al., "Involutional Osteoporosis", *New Engl. J. of Med.,* vol. 314, pp. 1676–1686, (1986).

Cummings, S.R., et al., "Should Perimenopausal Women Be Screened for Osteoporosis?", *Ann. Int. Med.,* vol. 104, pp. 817–823, (1986).

Courpron, P., "Bone Tissue Mechanisms Underlying Osteoporosis," *Orthop. Clin. North Amer.,* vol. 12, p. 513–545, (1981).

Frost, H.M., "Mechanical Determinants of Bone Modeling," *Metabol. Bone. Dis. Rel. Res.,* vol. 4, p. 217–229, (1982).

Mulsant, B.H., "A Neural Network as an Approach to Clinical Diagnosis", *MD Computing,* vol. 7, pp. 25–36 (1990).

Cohen, I., et al., "Diagnosing Autism: A Neural Net–Based Tool", PCAI, pp. 22–25 (May/Jun. 1994).

Boone J.M.,et al., "Neural Networks in Radiologic Diagnosis. I. Introduction and Illustration", Invest. Radiol., vol. 25, pp. 1012–1016, (1990).

Gross, G.W., et al., "Neural Networks in Radiologic Diagnosis. II. Interpretation of Neonatal Chest Radiographs", Invest. Radiol., vol. 25, pp. 1017–1023 (1990).

Wu, Y., et al., "Artificial Neural Networks in Mammography: Application to Decision Making in the Diagnosis of Breast Cancer", *Radiology,* vol. 187, pp. 81–87 (1993).

Kappen, H.J., et al., "Neural Network Analysis to Predict Treatment Outcome", *Annals of Oncology,* vol. 4, Supp. 4, pp. S31–S34 (1993).

Ravdin, P.M., et al., "A practical application of neural network analysis of predicting outcome of individual breast cancer patients", *Breast Cancer Research and Treatment,* vol. 22, pp. 285–293 (1992).

Wilding, P., et al., "Application of back propogation neural networks to diagnosis of breast and ovarian cancer", Cancer Letters, vol. 77, pp. 145–153 (1994).

Sharpe, P.K., et al., "Artificial Neural Networks in Diagnosis of Thyroid Function from in Vitro Laboratory Tests," *Clin. Chem.* vol. 39, No. 11, pp. 2248–2253 (1993).

Snow, P.S. et al., "Artificial Neural Networks in the Diagnosis and Prognosis of Prostat Cancer: A Pilot Study" *J. Urology*, vol. 152: 1923–1926 (1994).

Furlong, J.W., "Neural Network of Serial Cardiac Enzyme Data: A Clinical Application of Artificial Machine Intelligence", *Am. J. Clin. Pathol.*, vol. 96, No. 1, pp. 134–141 (Jul. 1991).

Mazess, R., et al., "Performance Evaluation of a Dual-Energy X–Ray Bone Densitometer", *Calcif. Tissue Int.*, vol. 44, pp. 228–232 (1989).

Mazess, R. B., et al., "Measurement of Bone by DualPhoton Absorptiometry (DPA) and Dual–Energy X–Ray Absorptiometry (DEXA)", *Annales Chirugiae et Gynaecologiae*, vol. 77, pp. 187–203 (1988).

Frenster, J.H., "Neural Networks for Pattern Recognition in Medical Diagnosis", *Annual International Conference in the IEEE Engineering in Medicine and Biology Society*, vol. 12, No. 3, issued 1990, pp. 1423–1424.

Taylor, J.G., *The Promise of Neural Networks*, Springer–Verlag, pp. 10–19, 37–61, 64–95.

Hernandez, C.A. et al., "How to Choose the Training Data for Neural Network Medical Diagnosis Systems", *ISA*, pp. 283–290 (1993).

Bavarian, B., "Chapter 19: Neural Networks", pp. 421–429.

\* cited by examiner

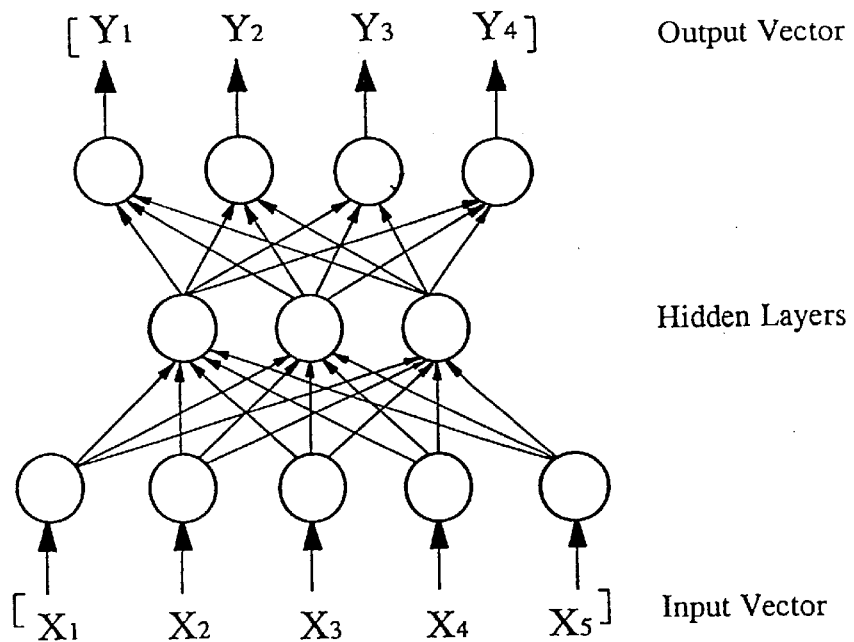
FIG. 1
FIG. 2
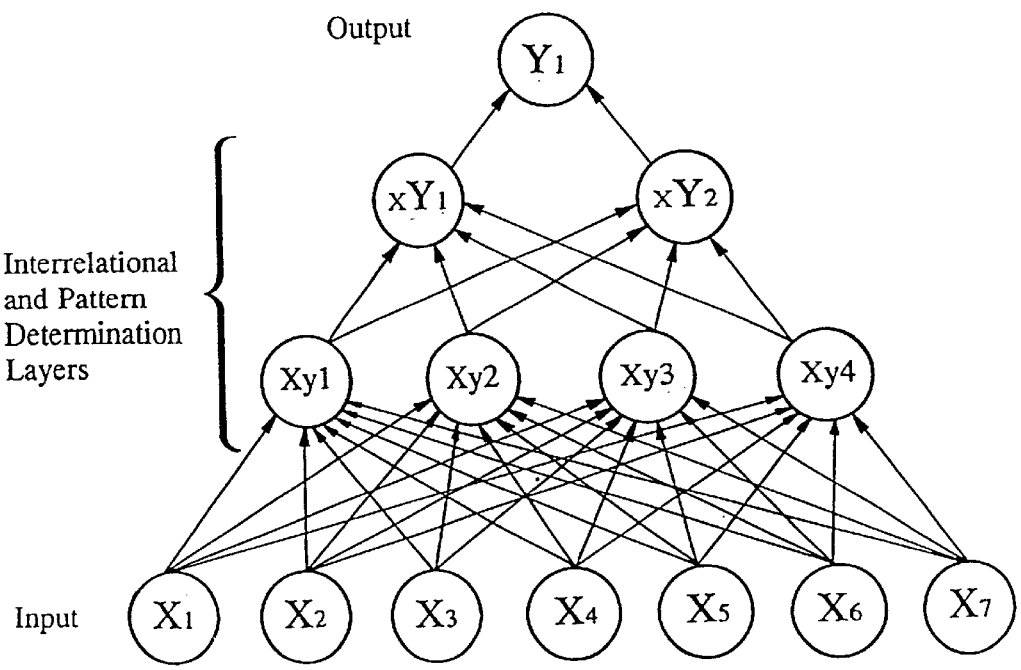

Prostate Cancer Prognosis Training Data

| nTPS | nPSA | PAP | CKA | Testosterone | Stable | Progress | ANNoutput1 | ANNoutput2 | Actual | Index |
|---|---|---|---|---|---|---|---|---|---|---|
| 0.53 | 0.69 | 7.8 | 1.3 | 5.6 | 0.1 | 0.9 | 0.10 | 0.90 | 0.9 | 0.90 |
| 0.55 | 0.59 | 0.7 | 0.4 | 1.9 | 0.9 | 0.1 | 0.90 | 0.10 | 0.1 | 0.10 |
| 0.8 | 0.44 | 0.6 | 1 | 0.3 | 0.9 | 0.1 | 0.90 | 0.10 | 0.1 | 0.10 |
| 0.6 | 0.02 | 1.3 | 1.2 | 1.6 | 0.9 | 0.1 | 0.89 | 0.11 | 0.1 | 0.11 |
| 0.92 | 0 | 1.2 | 1.7 | 1.2 | 0.9 | 0.1 | 0.90 | 0.10 | 0.1 | 0.10 |
| 0.3 | 0.02 | 1.5 | 0.8 | 0.5 | 0.9 | 0.1 | 0.90 | 0.10 | 0.1 | 0.10 |
| 0.62 | 0.04 | 0.7 | 0.6 | 0.8 | 0.9 | 0.1 | 0.90 | 0.10 | 0.1 | 0.10 |
| 1.13 | 0 | 0.4 | 0.9 | 1.1 | 0.9 | 0.1 | 0.90 | 0.10 | 0.1 | 0.10 |
| 1.66 | 0.01 | 0.5 | 0.9 | 1 | 0.9 | 0.1 | 0.90 | 0.10 | 0.1 | 0.10 |
| 0.8 | 0.26 | 1.6 | 0.6 | 0.3 | 0.9 | 0.1 | 0.89 | 0.11 | 0.1 | 0.11 |
| 0.82 | 0.42 | 1.1 | 1.2 | 0.9 | 0.9 | 0.1 | 0.90 | 0.10 | 0.1 | 0.10 |
| 0.81 | 0.44 | 2.9 | 0.4 | 0.1 | 0.9 | 0.1 | 0.90 | 0.10 | 0.1 | 0.10 |
| 0.68 | 0.66 | 5.5 | 0.2 | 0.3 | 0.1 | 0.9 | 0.10 | 0.90 | 0.9 | 0.90 |
| 0.68 | 0.22 | 3 | 0.9 | 2.9 | 0.1 | 0.9 | 0.10 | 0.90 | 0.9 | 0.90 |
| 0.55 | 0.02 | 1.4 | 1 | 0.7 | 0.9 | 0.1 | 0.90 | 0.10 | 0.1 | 0.10 |
| 0.5 | 0.01 | 0.5 | 0.7 | 2 | 0.9 | 0.1 | 0.90 | 0.10 | 0.1 | 0.10 |
| 0.31 | 0.02 | 0.5 | 10 | 4.3 | 0.1 | 0.9 | 0.17 | 0.83 | 0.9 | 0.83 |
| 0.66 | 0.44 | 2.6 | 1.2 | 4.1 | 0.1 | 0.9 | 0.11 | 0.89 | 0.9 | 0.89 |
| 1.6 | 0.02 | 2.6 | 4.8 | 0.4 | 0.1 | 0.9 | 0.11 | 0.89 | 0.9 | 0.89 |
| 1.99 | 0.01 | 1.9 | 5.4 | 0.5 | 0.9 | 0.1 | 0.88 | 0.12 | 0.1 | 0.12 |
| 0.66 | 0.44 | 2.6 | 1.2 | 4.1 | 0.1 | 0.9 | 0.10 | 0.90 | 0.9 | 0.90 |
| 0.75 | 0.93 | 29.2 | 0.2 | 5.1 | 0.1 | 0.9 | 0.10 | 0.90 | 0.9 | 0.90 |
| 1.04 | 1.76 | 77 | 1.2 | 7 | 0.9 | 0.1 | 0.90 | 0.10 | 0.1 | 0.10 |
| 0.56 | 1 | 8.1 | 0.4 | 0.9 | 0.9 | 0.1 | 0.90 | 0.10 | 0.1 | 0.10 |
| 0.8 | 0.86 | 7.3 | 2.3 | 0.4 | 0.1 | 0.9 | 0.10 | 0.90 | 0.9 | 0.90 |
| 0.47 | 0.37 | 3.3 | 1 | 5.1 | 0.1 | 0.9 | 0.10 | 0.90 | 0.9 | 0.90 |
| 0.49 | 0.02 | 1.7 | 0.6 | 0.2 | 0.9 | 0.1 | 0.90 | 0.10 | 0.1 | 0.10 |
| 0.59 | 0.02 | 0.9 | 0.4 | 0.2 | 0.9 | 0.1 | 0.90 | 0.10 | 0.1 | 0.10 |

FIG. 5A

Prostate Cancer Prognosis Training Data

| nTPS | nPSA | PAP | CKA | Testosterone | Stable | Progress | NNoutput1 | NNoutput2 | Actual | Index |
|---|---|---|---|---|---|---|---|---|---|---|
| 0.44 | 0.02 | 1 | 0.3 | 0.3 | 0.9 | 0.1 | 0.90 | 0.10 | 0.1 | 0.10 |
| 0.45 | 0.01 | 1 | 0.1 | 0.3 | 0.9 | 0.1 | 0.89 | 0.11 | 0.1 | 0.11 |
| 0.89 | 0.01 | 0.6 | 1.1 | 0.6 | 0.9 | 0.1 | 0.89 | 0.11 | 0.1 | 0.11 |
| 1.73 | 1.28 | 12.1 | 5 | 3.8 | 0.1 | 0.9 | 0.10 | 0.90 | 0.9 | 0.90 |
| 1.83 | 0.15 | 5.1 | 1.8 | 0.4 | 0.9 | 0.1 | 0.90 | 0.10 | 0.1 | 0.10 |
| 0.82 | 0.01 | 0.4 | 0.5 | 0.1 | 0.9 | 0.1 | 0.90 | 0.10 | 0.1 | 0.10 |
| 0.62 | 0.04 | 0.7 | 0.6 | 0.8 | 0.9 | 0.1 | 0.90 | 0.10 | 0.1 | 0.10 |
| 0.35 | 0.01 | 1 | 0.6 | 1 | 0.9 | 0.1 | 0.90 | 0.10 | 0.1 | 0.10 |
| 1.06 | 0.43 | 3.8 | 1 | 4.6 | 0.1 | 0.9 | 0.10 | 0.90 | 0.9 | 0.90 |
| 0.25 | 0.04 | 0.3 | 0.7 | 0.4 | 0.9 | 0.1 | 0.90 | 0.10 | 0.1 | 0.10 |
| 0.11 | 0.03 | 1.8 | 1.5 | 0.5 | 0.9 | 0.1 | 0.90 | 0.10 | 0.1 | 0.10 |
| 0.74 | 0.01 | 0.2 | 0.5 | 0.1 | 0.9 | 0.1 | 0.89 | 0.11 | 0.1 | 0.11 |

FIG. 5B

Prostate Cancer Prognosis Testing Data

| nTPS | nPSA | PAP | CKA | Testosterone | Stable | Progress | NNoutput1 | NNoutput2 | Actual | Index |
|---|---|---|---|---|---|---|---|---|---|---|
| 0.39 | 0.15 | 2.3 | 1 | 1.4 | 0.9 | 0.1 | 0.89 | 0.11 | 0.1 | 0.11 |
| 0.9 | 0.05 | 2 | 1.3 | 0.6 | 0.9 | 0.1 | 0.90 | 0.10 | 0.1 | 0.10 |
| 0.43 | 0.29 | 1.9 | 2.2 | 0.8 | 0.9 | 0.1 | 0.90 | 0.10 | 0.1 | 0.10 |
| 0.63 | 0.37 | 3.4 | 1 | 5 | 0.1 | 0.9 | 0.10 | 0.90 | 0.9 | 0.90 |
| 0.52 | 0.01 | 0.3 | 1.8 | 0.1 | 0.9 | 0.1 | 0.88 | 0.12 | 0.1 | 0.12 |
| 1.33 | 0.42 | 0.1 | 1.1 | 0.6 | 0.1 | 0.9 | 0.77 | 0.23 | 0.9 | 0.23 |
| 0.76 | 0.6 | 51.7 | 0.5 | 3.9 | 0.1 | 0.9 | 0.10 | 0.90 | 0.9 | 0.90 |
| 0.64 | 0 | 1.1 | 2.3 | 0.7 | 0.9 | 0.1 | 0.88 | 0.12 | 0.1 | 0.12 |
| 0.3 | 0.05 | 1.1 | 2.2 | 0.7 | 0.9 | 0.1 | 0.87 | 0.13 | 0.1 | 0.13 |
| 1.14 | 1.01 | 1.3 | 1 | 0.5 | 0.9 | 0.1 | 0.89 | 0.11 | 0.1 | 0.11 |
| 0.7 | 0.03 | 0.6 | 0.1 | 1.5 | 0.9 | 0.1 | 0.90 | 0.10 | 0.1 | 0.10 |
| 0.42 | 0.25 | 2.2 | 0.9 | 6.6 | 0.9 | 0.1 | 0.81 | 0.19 | 0.1 | 0.19 |

FIG. 5C

ProstAsure™ Training Data

| ID | AGE | PSA | PAP | CKBB | CKMB | CKMM | TOTAL CK | DRE | ETHNIC | GROUP |
|---|---|---|---|---|---|---|---|---|---|---|
| 2 | 72 | 12.24 | 1.59 | 0.9 | 6 | 54.5 | 61.4 | 3 | 1 | 3 |
| 3 | 61 | 6.17 | 0.57 | 0 | 4.4 | 239.7 | 244.1 | 3 |  | 3 |
| 7 | 73 | 7.8 | 0.88 | 0.5 | 0 | 131.8 | 132.3 | 3 | 1 | 3 |
| 8 | 67 | 54.84 | 1.26 | 2.5 | 2.3 | 344.3 | 349.1 | 3 | 1 | 3 |
| 11 | 62 | 0.4 | 0.7 | 0.6 | 1.2 | 116.3 | 118.1 | 2 | 3 | 1 |
| 27 | 70 | 0.52 | 0.29 | 1.7 | 0 | 285.9 | 287.6 | 2 | 2 | 5 |
| 36 | 72 | 117.25 | 8.31 | 2.2 | 2.6 | 100.9 | 105.7 | 3 | 2 | 3 |
| 41 | 80 | 7.22 | 0.98 | 1.5 | 2 | 76.7 | 80.2 | 3 | 1 | 3 |
| 45 | 60 | 2.17 | 0.55 | 0.5 | 1.5 | 87.1 | 89.1 | 2 | 3 | 1 |
| 50 | 86 | 54.04 | 0.75 | 0 | 0 | 46.2 | 46.2 | 3 | 1 | 3 |
| 55 | 77 | 5.1 | 3.14 | 0 | 0 | 84 | 84 | 2 | 1 | 1 |
| 63 | 37 | 1.5 | 0.24 | 0.8 | 1.8 | 107.2 | 109.8 | 2 | 3 | 1 |
| 71 | 76 | 21.42 | 1.6 | 0 | 2.8 | 229.3 | 232.1 | 3 | 1 | 3 |
| 73 | 74 | 0.93 | 0.63 | 0.8 | 1.4 | 57.2 | 59.4 | 1 | 3 | 1 |
| 77 | 67 | 2.31 | 1.08 | 0 | 2 | 47.8 | 49.8 | 1 | 1 | 1 |
| 80 | 66 | 1.04 | 0.88 | 1 | 2.6 | 95.2 | 98.8 | 2 | 1 | 1 |
| 81 | 67 | 0.86 | 1.25 | 0 | 1.1 | 65.1 | 66.2 | 2 | 3 | 1 |
| 82 | 78 | 3.81 | 1.01 | 0 | 2.3 | 63 | 65.3 | 1 | 1 | 1 |
| 91 | 57 | 1.93 | 0.94 | 0.9 | 2.3 | 75.9 | 79.1 | 1 | 1 | 1 |
| 98 | 43 | 0.96 | 1.23 | 1 | 0 | 93.1 | 94.1 | 2 | 1 | 1 |
| 115 | 70 | 1.46 | 1 | 0.6 | 6.9 | 200.2 | 207.7 | 2 | 1 | 1 |
| 132 | 60 | 3.23 | 1.3 | 0.4 | 1.9 | 82.2 | 84.5 | 2 | 1 | 1 |
| 135 | 50 | 0.56 | 0.99 | 0 | 5.7 | 408.4 | 414.1 | 1 | 1 | 1 |
| 137 | 61 | 6.78 | 1.49 | 0.9 | 2.6 | 65.2 | 68.7 | 2 | 1 | 1 |
| 138 | 68 | 26.62 | 4.14 | 1.1 | 3.1 | 246.2 | 250.4 | 2 | 3 | 1 |
| 139 | 54 | 8.7 | 1.32 | 0 | 2.4 | 80 | 82.4 | 1 | 1 | 3 |
| 140 | 73 | 4.85 | 1.03 | 0.8 | 2 | 55.8 | 58.6 | 3 | 1 | 3 |
| 160 | 56 | 1.31 | 1.21 | 0 | 2.7 | 151.5 | 154.2 | 2 | 1 | 1 |
| 168 | 72 | 1.59 | 1.15 | 1.6 | 3 | 89.6 | 94.2 | 2 | 1 | 1 |
| 179 | 68 | 5.84 | 3.72 | 0.8 | 2.8 | 126.9 | 130.5 | 2 | 5 | 1 |
| 187 | 84 | 3.45 | 1.42 | 0.5 | 3.6 | 97.5 | 101.6 | 2 | 1 | 1 |
| 196 | 63 | 1.88 | 1.08 | 0 | 2.3 | 91.7 | 94 | 1 | 1 | 1 |
| 200 | 70 | 2.85 | 1.04 | 0.7 | 3.6 | 78.4 | 82.7 | 2 | 1 | 1 |
| 205 | 71 | 0.4 | 0.59 | 0.7 | 2.6 | 140.3 | 143.6 | 2 | 1 | 1 |
| 208 | 69 | 3.32 | 1.04 | 0.5 | 3.2 | 90.6 | 94.3 | 2 | 1 | 1 |
| 213 | 81 | 0.4 | 1.56 | 0.9 | 2.4 | 62.1 | 65.4 | 2 | 1 | 1 |
| 214 | 69 | 1.08 | 1.6 | 1.1 | 0 | 53.6 | 54.7 | 2 | 1 | 1 |
| 220 | 72 | 1.92 | 1.77 | 0.7 | 2.1 | 88.2 | 91 | 2 | 1 | 1 |
| 245 | 55 | 50.91 | 4.5 | 0 | 1.4 | 177.8 | 179.2 | 3 | 2 | 3 |
| 247 | 83 | 24.41 | 3.79 | 0 | 2.3 | 50.7 | 53 | 3 | 1 | 3 |
| 263 | 64 | 20.44 | 1.57 | 0.9 | 1.4 | 77.7 | 80 | 3 | 1 | 3 |
| 264 | 68 | 4.73 | 2.96 | 0.5 | 1.4 | 52.8 | 54.7 | 2 | 3 | 1 |
| 265 | 60 | 2.14 | 1.04 | 0.9 | 1.5 | 44.5 | 46.9 | 3 | 3 | 3 |
| 272 | 78 | 4.59 | 0.92 | 0 | 3.8 | 93.9 | 97.7 | 1 | 1 | 1 |
| 278 | 65 | 5.63 | 2.7 | 0.9 | 4.6 | 154.7 | 160.2 | 2 | 1 | 1 |
| 296 | 46 | 0.74 | 0.94 | 1 | 1.5 | 1452.1 | 1454.6 | 1 | 1 | 5 |
| 312 | 23 | 0.54 | 0.97 | 0 | 0.8 | 228.3 | 229.1 | 4 | 2 | 5 |

FIG. 6A

| ID | AGE | PSA | PAP | CKBB | CKMB | CKMM | TOTAL CK | DRE | ETHNIC | GROUP |
|---|---|---|---|---|---|---|---|---|---|---|
| 314 | 37 | 0.67 | 0.95 | 0 | 1.6 | 190.7 | 192.3 | 4 | 2 | 5 |
| 315 | 36 | 0.4 | 1.31 | 0 | 6.3 | 460.8 | 467.1 | 4 | 2 | 5 |
| 321 | 37 | 0.56 | 1 | 0 | 1.9 | 288.3 | 290.2 | 4 | 4 | 5 |
| 327 | 41 | 1.08 | 1.1 | 0 | 3.3 | 463 | 466.3 | 4 | 2 | 5 |
| 328 | 46 | 1.13 | 1.05 | 0 | 1 | 479 | 480 | 4 | 2 | 5 |
| 330 | 47 | 0.86 | 0.97 | 1 | 2.8 | 368.1 | 371.9 | 4 | 2 | 5 |
| 331 | 52 | 8.03 | 1.36 | 0.9 | 0 | 145.6 | 146.5 | 4 | 2 | 5 |
| 334 | 47 | 0.71 | 0.84 | 0 | 1.9 | 230.1 | 232 | 4 | 2 | 5 |
| 337 | 47 | 0.4 | 0.84 | 0 | 0 | 104.8 | 104.8 | 4 | 2 | 5 |
| 340 | 58 | 4.1 | 1.57 | 0 | 2.2 | 558.8 | 561 | 4 | 4 | 5 |
| 347 | 73 | 1.19 | 1.28 | 1.1 | 3.2 | 420.5 | 424.8 | 4 | 1 | 5 |
| 350 | 83 | 1.82 | 0.48 | 0 | 5.6 | 235.4 | 241 | 4 | 1 | 5 |
| 351 | 70 | 1.92 | 0.87 | 0.9 | 4.8 | 201 | 206.7 | 4 | 1 | 5 |
| 355 | 81 | 2.48 | 2.09 | 1.1 | 3.5 | 153.1 | 157.7 | 4 | 1 | 5 |
| 358 | 68 | 3.29 | 1.46 | 0 | 2.3 | 141.9 | 144.2 | 4 | 1 | 5 |
| 361 | 62 | 0.9 | 1.54 | 1.1 | 2.2 | 137.6 | 140.9 | 4 | 1 | 5 |
| 363 | 72 | 0.4 | 1.09 | 1.3 | 3.1 | 130.2 | 134.6 | 4 | 1 | 5 |
| 368 | 66 | 4.12 | 1.67 | 1.1 | 3.4 | 137.2 | 141.7 | 4 | 1 | 5 |
| 370 | 66 | 2.77 | 1.12 | 1.1 | 3.1 | 91.8 | 96 | 4 | 1 | 5 |
| 373 | 68 | 1.86 | 1.27 | 1.3 | 1.6 | 126.7 | 129.6 | 4 | 1 | 5 |
| 380 | 68 | 1.62 | 1.26 | 0.8 | 3.8 | 119.3 | 123.9 | 4 | 1 | 5 |
| 386 | 81 | 3.04 | 3 | 0 | 6.3 | 184.3 | 190.6 | 4 | 1 | 5 |
| 387 | 70 | 0.6 | 1.24 | 0.8 | 2.8 | 90 | 93.6 | 4 | 1 | 5 |
| 389 | 31 | 0.4 | 0.93 | 0 | 2.1 | 402.9 | 405 | 4 | 2 | 5 |
| 391 | 39 | 1.16 | 0.73 | 0 | 0.6 | 116.6 | 117.2 | 4 | 2 | 5 |
| 392 | 30 | 1.1 | 0.74 | 0 | 0.8 | 160 | 160.8 | 4 | 1 | 5 |
| 396 | 49 | 1.06 | 1.81 | 0.9 | 3.4 | 252 | 256.3 | 4 | 2 | 5 |
| 397 | 45 | 0.4 | 1.33 | 0.8 | 1.6 | 196.9 | 199.3 | 4 | 2 | 5 |
| 399 | 51 | 1.6 | 0.86 | 1 | 4.5 | 191 | 196.5 | 4 | 2 | 5 |
| 401 | 33 | 0.4 | 0.87 | 0 | 0.6 | 206.7 | 207.3 | 4 | 2 | 5 |
| 402 | 31 | 0.4 | 0.92 | 0.5 | 2.8 | 307.9 | 311.2 | 4 | 2 | 5 |
| 403 | 33 | 0.71 | 1.08 | 0.4 | 1.8 | 860.5 | 862.7 | 4 | 2 | 5 |
| 407 | 37 | 1.39 | 0.85 | 0.5 | 2.5 | 309.3 | 312.3 | 4 | 2 | 5 |
| 408 | 37 | 0.58 | 1.41 | 1 | 4.4 | 226.5 | 231.9 | 4 | 2 | 5 |
| 409 | 29 | 0.4 | 0.74 | 0 | 0.7 | 120.4 | 121.1 | 4 | 2 | 5 |
| 412 | 38 | 0.4 | 1.34 | 0 | 2.2 | 142.9 | 145.1 | 4 | 2 | 5 |
| 413 | 27 | 0.4 | 1.05 | 0 | 1.2 | 145.6 | 146.8 | 4 | 2 | 5 |
| 414 | 28 | 0.4 | 1.36 | 0 | 1.7 | 129.8 | 131.5 | 4 | 2 | 5 |
| 420 | 43 | 0.4 | 0.47 | 0 | 2.2 | 114 | 116.2 | 4 | 2 | 5 |
| 425 | 28 | 0.4 | 0.77 | 0 | 2.7 | 111.1 | 113.8 | 4 | 2 | 5 |
| 426 | 58 | 1.3 | 1.65 | 0 | 8.3 | 412.8 | 421.1 | 4 | 2 | 5 |
| 429 | 59 | 0.65 | 1.78 | 0 | 4.3 | 200.9 | 205.2 | 4 | 2 | 5 |
| 432 | 57 | 0.93 | 1.12 | 0.5 | 3.2 | 279.8 | 283.5 | 4 | 2 | 5 |
| 434 | 46 | 3.01 | 0.92 | 0 | 0.8 | 137 | 137.8 | 4 | 2 | 5 |
| 438 | 56 | 0.62 | 2.23 | 0.4 | 2.9 | 297.1 | 300.4 | 4 | 2 | 5 |
| 440 | 56 | 0.6 | 1.23 | 0.6 | 0 | 365.2 | 365.8 | 4 | 2 | 5 |
| 442 | 59 | .4 | 1.53 | 0 | 0 | 251.1 | 251.1 | 4 | 2 | 5 |

FIG. 6B

| ID | AGE | PSA | PAP | CKBB | CKMB | CKMM | TOTAL CK | DRE | ETHNIC | GROUP |
|---|---|---|---|---|---|---|---|---|---|---|
| 454 | 71 | 0.65 | 0.48 | 0 | 2.8 | 157.1 | 159.9 | 3 | 1 | 3 |
| 455 | 70 | 6.65 | 0.86 | 0.7 | 1.9 | 125.2 | 127.8 | 3 | 3 | 3 |
| 456 | 63 | 13.93 | 1.17 | 1.4 | 4 | 126.2 | 131.6 | 3 | 1 | 3 |
| 458 | 79 | 1.61 | 0.58 | 0.8 | 1.9 | 130.2 | 132.9 | 1 | 1 | 3 |
| 466 | 68 | 9.08 | 7.17 | 0.7 | 0 | 62.4 | 63.1 | 2 | 1 | 3 |
| 468 | 70 | 86.59 | 21.21 | 1.5 | 5.1 | 380.3 | 386.9 | 3 | 2 | 3 |
| 470 | 44 | 5.19 | 0.91 | 0.5 | 0 | 58.6 | 59.1 | 2 | 1 | 3 |
| 471 | 59 | 7.16 | 1.03 | 0.3 | 0 | 97.7 | 98 | 3 | 1 | 3 |
| 477 | 82 | 62.6 | 1.03 | 0.8 | 2.6 | 77.3 | 80.7 | 3 | 1 | 3 |
| 479 | 52 | 6.2 | 0.99 | 1.1 | 1.6 | 106.8 | 109.5 | 1 | 1 | 3 |
| 495 | 77 | 6.85 | 1.39 | 0 | 3.2 | 110.8 | 114 | 1 | 1 | 3 |
| 501 | 40 | 0.67 | 0.82 | 1.3 | 3.3 | 283.6 | 288.2 | 1 | | 5 |
| 502 | 65 | 3.18 | 1.28 | 0.7 | 4.7 | 177.2 | 182.6 | 1 | | 5 |
| 507 | 47 | 2.61 | 1.19 | 0.7 | 3.1 | 116.9 | 120.7 | 1 | | 5 |
| 508 | 52 | 0.55 | 0.56 | 1.9 | 3.9 | 227.7 | 233.5 | 1 | | 5 |
| 509 | 50 | 0.73 | 1.39 | 1.6 | 2.6 | 217.9 | 222.1 | 1 | | 5 |
| 511 | 53 | 0.53 | 0.94 | 1.1 | 3 | 137.3 | 141.4 | 1 | | 5 |
| 515 | 47 | 1.23 | 1.12 | 1.4 | 1.9 | 57.2 | 60.5 | 1 | | 5 |
| 516 | 46 | 1.35 | 1.13 | 1.5 | 7.4 | 334.2 | 343.1 | 1 | | 5 |
| 518 | 43 | 0.71 | 0.98 | 1.4 | 3.2 | 249.8 | 254.4 | 1 | | 5 |
| 519 | 48 | 0.86 | 0.9 | 0.8 | 5.4 | 374.5 | 380.7 | 1 | | 5 |
| 520 | 47 | 0.91 | 0.88 | 0 | 2.1 | 130.6 | 132.7 | 1 | | 5 |
| 526 | 41 | 1.16 | 1.1 | 1.1 | 4 | 301.4 | 306.5 | 1 | | 5 |
| 530 | 67 | 1.31 | 0.91 | 0 | 9.1 | 277.9 | 287 | 1 | | 5 |
| 533 | 40 | 0.82 | 1.06 | 0.8 | 2.8 | 181.6 | 185.2 | 1 | | 5 |
| 540 | 66 | 0.77 | 1.02 | 0.7 | 4.8 | 212.6 | 218.1 | 1 | | 5 |
| 542 | 70 | 1.06 | 1.16 | 0.8 | 10.2 | 203 | 214 | 2 | | 1 |
| 543 | 73 | 12.45 | 1.47 | 1.2 | 5.9 | 139.3 | 146.4 | 2 | | 1 |
| 548 | 64 | 10.42 | 1.5 | 1.4 | 2.7 | 138.2 | 142.3 | 2 | | 1 |
| 549 | 64 | 1.5 | 0.61 | 1.1 | 3.7 | 193.2 | 198 | 2 | | 1 |
| 557 | 62 | 0 | 0.56 | 0.9 | 2.2 | 202.9 | 206 | 2 | | 1 |
| 559 | 76 | 3.84 | 1.26 | 1.7 | 7.2 | 136.7 | 145.6 | 2 | | 1 |
| 560 | 64 | 0.89 | 0.85 | 0.9 | 1.7 | 117 | 119.6 | 2 | | 1 |
| 570 | 49 | 0.55 | 0.66 | 1 | 5.1 | 182.9 | 189 | 2 | | 1 |
| 572 | 56 | 0.58 | 0.92 | 0.9 | 2.1 | 115.4 | 118.4 | 2 | | 1 |
| 575 | 59 | 4.01 | 0.88 | 0.9 | 2.4 | 159 | 162.3 | 2 | | 1 |
| 578 | 62 | 1.12 | 0.97 | 0.5 | 5.4 | 203 | 208.9 | 2 | | 1 |
| 586 | 39 | 0.95 | 1.31 | 1.3 | 1.6 | 165.2 | 168.1 | 2 | | 1 |
| 595 | 54 | 1.59 | 1.18 | 0.7 | 2.7 | 101.3 | 104.7 | 2 | | 1 |
| 599 | 78 | 5.65 | 1.28 | 2 | 3.3 | 225.9 | 231.2 | 2 | | 1 |
| 609 | 52 | 1.98 | 0.77 | 1 | 3.4 | 152 | 156.4 | 2 | | 1 |
| 654 | 73 | 1.2 | 0.55 | 0 | 2.2 | 209.3 | 211.5 | 3 | | 3 |
| 655 | 76 | 2.73 | 5.98 | 0 | 3.2 | 470.2 | 473.4 | 3 | | 3 |
| 667 | 69 | 5.45 | 1.05 | 0 | 1.7 | 169.7 | 171.4 | 3 | | 3 |
| 670 | 61 | 8.59 | 2.26 | 0.6 | 3 | 93.3 | 96.9 | 3 | | 3 |
| 676 | 73 | 7.55 | 1.04 | 0 | 5 | 356.6 | 361.6 | 3 | | 3 |
| 681 | 72 | 0.4918 | 0.72 | 1.3 | 2.1 | 107.8 | 111.2 | 3 | | 3 |

FIG. 6C

| ID | AGE | PSA | PAP | CKBB | CKMB | CKMM | TOTAL CK | DRE | ETHNIC | GROUP |
|---|---|---|---|---|---|---|---|---|---|---|
| 682 | 85 | 20.54 | 1.26 | 0.7 | 2.6 | 60.6 | 63.9 | 3 | | 3 |
| 686 | 81 | 7.39 | 1.14 | 1.1 | 2.5 | 88.3 | 91.9 | 3 | | 3 |
| 687 | 83 | 7.6 | 1.33 | 0 | 3.9 | 178.6 | 182.5 | 3 | | 3 |
| 690 | 92 | 65.87 | 16.43 | 2.4 | 7.2 | 153.7 | 163.3 | 3 | | 3 |
| 694 | 73 | 16.38 | 1.74 | 0 | 1.9 | 85.7 | 87.6 | 3 | | 3 |
| 700 | 71 | 8.8 | 0.82 | 0.9 | 2.5 | 54.5 | 57.9 | 3 | | 3 |
| 701 | 77 | 29.76 | 3.13 | 0.7 | 1.9 | 51.7 | 54.3 | 3 | | 3 |
| 703 | 77 | 11.57 | 1.17 | 0.4 | 5.4 | 150.1 | 155.9 | 3 | | 3 |
| 707 | 80 | 10.58 | 1.9 | 0 | 2 | 62.6 | 64.6 | 3 | | 3 |
| 711 | 64 | 7.93 | 1.53 | 0.8 | 1.8 | 69.4 | 72 | 3 | | 3 |
| 735 | 67 | 201.09 | 68.79 | 2.5 | 2.3 | 44.5 | 49.3 | 3 | | 3 |
| 736 | 77 | 28.37 | 2.14 | 0.6 | 2.7 | 36.6 | 39.9 | 3 | | 3 |
| 763 | 76 | 298.23 | 76.54 | 2.2 | 2.4 | 138.8 | 143.4 | 3 | | 3 |
| 766 | 63 | 70.84 | 0.8 | 0.6 | 1.6 | 123.6 | 125.8 | 3 | | 3 |
| 768 | 56 | 18.73 | 4.01 | 0 | 0.9 | 101.2 | 102.1 | 3 | | 3 |

FIG. 6D

ProstAsure™ Training Data

| HTI ID | AGE | PSA | PAP | CKBB | CKMB | CKMM | DRE | GROUP | STAGE | ProstAsure |
|---|---|---|---|---|---|---|---|---|---|---|
| 541 | 42 | 1.91 | 0.92 | 0 | 1.5 | 295.3 | enlarged | 1 | | 10.4 |
| 544 | 76 | 4.67 | 2.18 | 1.4 | 2.7 | 109.4 | enlarged | 1 | | 30.1 |
| 545 | 58 | 1.71 | 1.28 | 0.6 | 2.1 | 76.8 | enlarged | 1 | | 24.2 |
| 547 | 48 | 0.9 | 0.9 | 0 | 3.9 | 156.4 | enlarged | 1 | | 12.6 |
| 550 | 52 | 1.28 | 0.69 | 0 | 2.3 | 107.1 | enlarged | 1 | | 21.8 |
| 551 | 71 | 1.23 | 0.72 | 1.6 | 2.8 | 114.5 | enlarged | 1 | | 27.6 |
| 552 | 58 | 14.76 | 1.79 | 1 | 7.3 | 280 | enlarged | 1 | | 41.3 |
| 555 | 75 | 5.74 | 1 | 0.7 | 1.7 | 132 | enlarged | 1 | | 41.8 |
| 556 | 84 | 4.46 | 1.06 | 1.1 | 3.3 | 108.3 | enlarged | 1 | | 39.8 |
| 558 | 41 | 1.28 | 0.77 | 1.3 | 5.2 | 269.2 | enlarged | 1 | | 9.9 |
| 561 | 62 | 4.23 | 0.63 | 1.4 | 4.5 | 216.5 | enlarged | 1 | | 29.9 |
| 562 | 47 | 0.55 | 0.74 | 0.4 | 2.1 | 176.3 | enlarged | 1 | | 10.9 |
| 563 | 70 | 0.74 | 1.08 | 0.7 | 4.3 | 164 | enlarged | 1 | | 17.1 |
| 564 | 79 | 1.6 | 0.84 | 0.9 | 4.7 | 176.3 | enlarged | 1 | | 25.2 |
| 567 | 59 | 1.52 | 1.33 | 1.1 | 4.1 | 308.8 | enlarged | 1 | | 10.3 |
| 568 | 61 | 1.64 | 0.87 | 0.7 | 3.3 | 84.1 | enlarged | 1 | | 28.1 |
| 569 | 86 | 0 | 0.73 | 0.5 | 10.1 | 557.6 | enlarged | 1 | | 11.1 |
| 571 | 53 | 0.77 | 0.79 | 0 | 1.5 | 178 | enlarged | 1 | | 12.9 |
| 573 | 66 | 0.7 | 1 | 1.1 | 2.1 | 96.2 | enlarged | 1 | | 22.2 |
| 574 | 67 | 2.22 | 1.37 | 0.7 | 1.8 | 39.6 | enlarged | 1 | | 33.2 |
| 576 | 38 | 0.52 | 0.64 | 0 | 2.1 | 70.9 | enlarged | 1 | | 15.3 |
| 577 | 62 | 0 | 0.57 | 0.3 | 9.1 | 529 | enlarged | 1 | | 8.3 |
| 580 | 67 | 1.05 | 0.94 | 0 | 12.5 | 382.7 | enlarged | 1 | | 10.7 |
| 581 | 70 | 2.88 | 0.92 | 0 | 3.4 | 118.2 | enlarged | 1 | | 32.8 |
| 582 | 65 | 1.53 | 0.87 | 0.6 | 3.2 | 104.9 | enlarged | 1 | | 27.0 |
| 583 | 65 | 3.03 | 1.33 | 1.1 | 3.4 | 117 | enlarged | 1 | | 27.3 |
| 584 | 65 | 0.78 | 0.72 | 0 | 3.4 | 209.4 | enlarged | 1 | | 14.8 |
| 585 | 67 | 3 | 1.26 | 0 | 2.8 | 120.9 | enlarged | 1 | | 28.9 |
| 587 | 61 | 1.18 | 1.05 | 1.6 | 0 | 104.1 | enlarged | 1 | | 21.2 |
| 588 | 75 | 6.5 | 1.87 | 0 | 1.2 | 61.7 | enlarged | 1 | | 44.5 |
| 589 | 70 | 1.57 | 1.05 | 1.1 | 3.4 | 194.8 | enlarged | 1 | | 18.5 |
| 590 | 77 | 11.33 | 1.11 | 0 | 6 | 237.5 | enlarged | 1 | | 49.4 |
| 591 | 64 | 2.31 | 1.5 | 0 | 2.6 | 231.2 | enlarged | 1 | | 15.1 |
| 592 | 74 | 5.96 | 1.46 | 0.6 | 5.5 | 147.3 | enlarged | 1 | | 36.4 |
| 593 | 62 | 3.16 | 0.92 | 1.3 | 1.6 | 93.3 | enlarged | 1 | | 33.4 |
| 594 | 70 | 9.49 | 0.71 | 1 | 2.6 | 114.9 | enlarged | 1 | | 57.9 |
| 596 | 67 | 4.09 | 0.93 | 0.6 | 1.8 | 116.3 | enlarged | 1 | | 36.7 |
| 597 | 45 | 1.76 | 0.72 | 1.2 | 12.2 | 98.5 | enlarged | 1 | | 21.4 |
| 598 | 61 | 0 | 0.44 | 0 | 1 | 139.5 | enlarged | 1 | | 18.7 |
| 600 | 57 | 1.56 | 0.78 | 0 | 2 | 99.8 | enlarged | 1 | | 25.4 |
| 601 | 64 | 4.75 | 1.47 | 0.7 | 5.9 | 304 | enlarged | 1 | | 19.9 |
| 602 | 64 | 1.18 | 1.29 | 1.2 | 4.5 | 121.7 | enlarged | 1 | | 18.7 |
| 603 | 59 | 1.79 | 1.01 | 0.4 | 3.6 | 176.7 | enlarged | 1 | | 17.7 |
| 604 | 69 | 1.45 | 1.93 | 0.8 | 1.9 | 41.6 | enlarged | 1 | | 26.0 |
| 605 | 67 | 2.13 | 1.19 | 1 | 1.3 | 102.2 | enlarged | 1 | | 27.4 |
| 606 | 83 | 2.38 | 1.59 | 0.4 | 3.2 | 41.3 | enlarged | 1 | | 36.5 |
| 607 | 68 | 2.41 | 1 | 1.1 | 4.3 | 161.6 | enlarged | 1 | | 24.6 |
| 608 | 59 | 1.46 | 0.64 | 0.6 | 1.6 | 82.4 | enlarged | 1 | | 29.5 |
| 610 | 59 | 1.62 | 0.94 | 0.7 | 4.1 | 242 | enlarged | 1 | | 13.6 |
| 611 | 59 | 1.12 | 0.79 | 0.7 | 3.4 | 226.1 | enlarged | 1 | | 13.3 |
| 612 | 68 | 1.55 | 0.79 | 0.6 | 5 | 206.9 | enlarged | 1 | | 19.0 |
| 613 | 70 | 4.3 | 1.47 | 0.8 | 3.8 | 401 | enlarged | 1 | | 19.6 |

FIG. 7A

| | | | | | | | | | |
|---|---|---|---|---|---|---|---|---|---|
| 614 | 58 | 5.02 | 4.19 | 0.6 | 4.1 | 199.4 | enlarged | 1 | 19.4 |
| 615 | 66 | 1.29 | 1.17 | 0.8 | 1.6 | 89.3 | enlarged | 1 | 25.0 |
| 616 | 58 | 1.52 | 0.97 | 1.4 | 5.8 | 154.2 | enlarged | 1 | 18.1 |
| 617 | 65 | 6.52 | 2.01 | 0.9 | 4.6 | 268.2 | enlarged | 1 | 23.9 |
| 618 | 62 | 5.47 | 0.92 | 0.9 | 4.1 | 208.7 | enlarged | 1 | 31.8 |
| 619 | 61 | 4.48 | 1.09 | 0.9 | 2.1 | 104.9 | enlarged | 1 | 35.4 |
| 620 | 62 | 0.83 | 0.92 | 1.5 | 7.1 | 403.9 | enlarged | 1 | 9.8 |
| 621 | 70 | 1.53 | 0.86 | 0 | 4.1 | 218.3 | enlarged | 1 | 18.0 |
| 622 | 63 | 3.31 | 1.21 | 0 | 3.2 | 3516.9 | enlarged | 1 | 16.3 |
| 623 | 60 | 3.29 | 1.04 | 0.6 | 3.5 | 169.9 | enlarged | 1 | 24.7 |
| 624 | 69 | 2.53 | 1.82 | 0.4 | 9.1 | 353 | enlarged | 1 | 13.0 |
| 625 | 76 | 3.43 | 1.09 | 0.9 | 3.1 | 96.8 | enlarged | 1 | 36.7 |
| 626 | 70 | 2.35 | 1.15 | 0.8 | 4.1 | 240.7 | enlarged | 1 | 17.8 |
| 627 | 49 | 0.68 | 0.9 | 0.7 | 4.1 | 400.5 | enlarged | 1 | 7.9 |
| 628 | 62 | 2.02 | 0.94 | 0.8 | 1.7 | 108.5 | enlarged | 1 | 27.1 |
| 629 | 76 | 1.85 | 1.23 | 0.8 | 3.9 | 9.5 | enlarged | 1 | 38.4 |
| 630 | 49 | 0.81 | 0.84 | 0.9 | 2.3 | 137 | enlarged | 1 | 14.5 |
| 631 | 51 | 1.01 | 1.14 | 0.3 | 2 | 83.6 | enlarged | 1 | 18.4 |
| 632 | 59 | 1.65 | 0.69 | 1.8 | 2 | 129.6 | enlarged | 1 | 24.2 |
| 633 | 61 | 0.76 | 0.78 | 0.6 | 2.6 | 129.4 | enlarged | 1 | 19.8 |
| 634 | 83 | 1.54 | 1.01 | 0.8 | 3.1 | 165.2 | enlarged | 1 | 25.0 |
| 635 | 46 | 0.72 | 0.59 | 0.8 | 1.7 | 168.8 | enlarged | 1 | 13.0 |
| 636 | 78 | 13.2 | 2.86 | 1.4 | 9.2 | 291.5 | enlarged | 1 | 34.8 |
| 637 | 78 | 4.37 | 1.35 | 0 | 2.5 | 85.3 | enlarged | 1 | 39.9 |
| 639 | 70 | 4.74 | 1.37 | 1 | 2.9 | 65.8 | enlarged | 1 | 39.7 |
| 640 | 54 | 1.06 | 1.2 | 0.8 | 2.1 | 126.9 | enlarged | 1 | 15.5 |
| 641 | 63 | 4.54 | 1.57 | 1.6 | 6.5 | 198.4 | enlarged | 1 | 23.0 |
| 642 | 55 | 4.4 | 2.21 | 0.6 | 3.3 | 171.1 | enlarged | 1 | 20.3 |
| 643 | 84 | 1.76 | 0.82 | 0.8 | 2.1 | 181.7 | enlarged | 1 | 26.4 |
| 644 | 71 | 1.68 | 1.22 | 1.1 | 2.6 | 72.5 | enlarged | 1 | 29.5 |
| 645 | 62 | 1.92 | 0.72 | 0 | 3.7 | 300.3 | enlarged | 1 | 13.8 |
| 646 | 68 | 3.27 | 1.71 | 0.9 | 2.5 | 120.8 | enlarged | 1 | 26.2 |
| 647 | 45 | 1.39 | 0.68 | 1.3 | 2.6 | 122.6 | enlarged | 1 | 18.7 |
| 648 | 61 | 2 | 0.97 | 1.3 | 2.5 | 140.5 | enlarged | 1 | 22.7 |
| 649 | 74 | 0.82 | 0.85 | 0.8 | 3.9 | 184 | enlarged | 1 | 19.0 |
| 650 | 67 | 3.04 | 1.51 | 0.9 | 8.9 | 426.3 | enlarged | 1 | 15.1 |
| 651 | 76 | 0.83 | 0.93 | 0 | 9.5 | 248.7 | enlarged | 1 | 13.8 |
| 866 | 52 | 1.02 | 1 | 0.8 | 1.7 | 157.4 | enlarged | 1 | 14.0 |
| 867 | 73 | 2.93 | 1.02 | 1.9 | 2.7 | 120 | enlarged | 1 | 31.3 |
| 868 | 59 | 0.63 | 0.64 | 0.8 | 0.9 | 69.7 | enlarged | 1 | 26.2 |
| 869 | 68 | 4.42 | 1.27 | 0.9 | 2 | 84.4 | enlarged | 1 | 37.5 |
| 870 | 67 | 2.55 | 0.74 | 0.9 | 2.5 | 106.3 | enlarged | 1 | 33.7 |
| 871 | 67 | 0.76 | 0.75 | 1 | 2 | 81.5 | enlarged | 1 | 27.5 |
| 872 | 43 | 0.86 | 1.03 | 0.6 | 10.3 | 232 | enlarged | 1 | 8.6 |
| 873 | 64 | 1.72 | 1.5 | 1.5 | 2.2 | 113 | enlarged | 1 | 20.1 |
| 874 | 55 | 1.21 | 1.35 | 0.9 | 6.7 | 218.6 | enlarged | 1 | 10.8 |
| 875 | 61 | 2.3 | 0.93 | 0.3 | 2.7 | 408.8 | enlarged | 1 | 13.9 |
| 876 | 78 | 12.61 | 0.84 | 0 | 1.5 | 96 | enlarged | 1 | 67.2 |
| 877 | 61 | 1.2 | 0.83 | 0.8 | 2.1 | 165.5 | enlarged | 1 | 18.3 |
| 878 | 70 | 1.94 | 1.03 | 0.7 | 2.4 | 108.5 | enlarged | 1 | 28.8 |
| 879 | 75 | 0.74 | 0.66 | 0 | 2.7 | 149.2 | enlarged | 1 | 24.9 |
| 880 | 65 | 1.94 | 0.91 | 0.5 | 1.8 | 102.7 | enlarged | 1 | 28.9 |
| 881 | 66 | 3.51 | -0.87 | 1 | 1.6 | 64.4 | enlarged | 1 | 39.9 |

FIG. 7B

| | | | | | | | | | |
|---|---|---|---|---|---|---|---|---|---|
| 882 | 69 | 5.46 | 1.57 | 0.7 | 2.5 | 105.4 | enlarged | 1 | 36.8 |
| 883 | 63 | 12.21 | 2.88 | 1.9 | 2.9 | 191.8 | enlarged | 1 | 36.3 |
| 884 | 62 | 4.27 | 1.53 | 0.8 | 3.8 | 142.8 | enlarged | 1 | 27.3 |
| 885 | 59 | 2.38 | 0.76 | 0.8 | 1.7 | 87.7 | enlarged | 1 | 31.9 |
| 886 | 61 | 3.56 | 1.08 | 1.8 | 1.5 | 87.9 | enlarged | 1 | 32.6 |
| 887 | 66 | 0.72 | 0.85 | 1.1 | 2.9 | 192.1 | enlarged | 1 | 15.2 |
| 888 | 65 | 0.86 | 0.91 | 1 | 3.2 | 129.1 | enlarged | 1 | 20.4 |
| 889 | 78 | 0.69 | 1.13 | 1.5 | 4.3 | 132.7 | enlarged | 1 | 20.8 |
| 99999 | 70 | 5.25 | 1.44 | 0.8 | 4.3 | 226 | enlarged | 1 | 26.9 |
| 638* | 65 | 1.54 | 0.95 | 1.1 | 3.6 | 74.5 | enlarged | 1 | 29.0 |
| 661 | 83 | 1.48 | 2.7 | 1.8 | 1.7 | 60.1 | normal | 3 | A | 22.5 |
| 663 | 73 | 41.76 | 5.08 | 0.8 | 2.5 | 148.8 | normal | 3 | A | 56.3 |
| 664 | 71 | 1.83 | 0.99 | 0 | 2.2 | 103.9 | normal | 3 | A | 29.9 |
| 673 | 72 | 4.88 | 0.8 | 0.4 | 2.1 | 168.5 | normal | 3 | A | 37.5 |
| 675 | 65 | 0 | 1.22 | 0 | 1.5 | 120.7 | normal | 3 | A | 15.5 |
| 680 | 70 | 0 | 0.72 | 2.4 | 2.1 | 262.6 | normal | 3 | A | 10.2 |
| 772 | 76 | 2.28 | 1.14 | 0.9 | 1.9 | 86 | normal | 3 | A | 33.4 |
| 773 | 77 | 7.41 | 0.87 | 1.1 | 4 | 139.8 | normal | 3 | A | 47.3 |
| 774 | 58 | 1 | 0.91 | 0.7 | 2.8 | 119.5 | normal | 3 | A | 19.6 |
| 775 | 85 | 1.03 | 1.59 | 0.6 | 2.5 | 120.2 | normal | 3 | A | 22.9 |
| 897 | 71 | 1.14 | 0.75 | 0 | 1.8 | 185.6 | normal | 3 | A | 20.6 |
| 898 | 71 | 1.1 | 0.45 | 0 | 18.3 | 857.6 | normal | 3 | A | 14.3 |
| 899 | 74 | 12.3 | 2.89 | 1 | 2.3 | 192.4 | normal | 3 | A | 40.3 |
| 900 | 59 | 0 | 0.86 | 0.6 | 3.3 | 131.8 | normal | 3 | A | 14.6 |
| 901 | 73 | 22.96 | 1.75 | 0.9 | 2.9 | 131 | normal | 3 | A | 61.9 |
| 902 | 67 | 0.87 | 1.15 | 0.5 | 2.9 | 113.7 | normal | 3 | A | 21.1 |
| 903 | 71 | 3.06 | 1.02 | 0.6 | 2 | 181.7 | normal | 3 | A | 26.6 |
| 904 | 72 | 2.98 | 1.79 | 1.9 | 1.8 | 74 | normal | 3 | A | 28.6 |
| 905 | 76 | 1.24 | 0.9 | 1.6 | 3.2 | 124.1 | normal | 3 | A | 26.2 |
| 906 | 80 | 8.65 | 1.5 | 1.2 | 1.2 | 53 | normal | 3 | A | 51.4 |
| 907 | 71 | 20.29 | 2.34 | 0.4 | 2.3 | 114.6 | normal | 3 | A | 57.5 |
| 908 | 67 | 0.59 | 0.8 | 0 | 3.1 | 120.8 | normal | 3 | A | 22.2 |
| 909 | 75 | 2.47 | 1.38 | 1 | 4 | 99.2 | normal | 3 | A | 29.9 |
| 910 | 74 | 45.34 | 3.43 | 1.2 | 2.4 | 90 | normal | 3 | A | 64.6 |
| 911 | 70 | 0 | 0.75 | 1.1 | 2.7 | 168.8 | normal | 3 | A | 16.1 |
| 912 | 72 | 1.05 | 0.71 | 0.6 | 2 | 147.9 | normal | 3 | A | 24.8 |
| 913 | 81 | 3.13 | 0.96 | 0.9 | 2.3 | 106.8 | normal | 3 | A | 37.1 |
| 914 | 66 | 16.73 | 2.49 | 0.4 | 2.4 | 138.8 | normal | 3 | A | 50.8 |
| 683 | 79 | 289.79 | 30.44 | 1 | 10 | 414.4 | B | 3 | B | 49.0 |
| 684 | 82 | 75.19 | 6.07 | 1.2 | 4.4 | 49.5 | B | 3 | B | 66.1 |
| 685 | 84 | 5.52 | 1.81 | 1 | 4.5 | 100.1 | B | 3 | B | 37.4 |
| 688 | 79 | 35.32 | 11.91 | 1.4 | 2.7 | 189.5 | B | 3 | B | 43.3 |
| 689 | 79 | 11.79 | 0.94 | 0 | 3.1 | 227.6 | B | 3 | B | 54.2 |
| 691 | 79 | 10.7 | 1.11 | 0.8 | 2.6 | 102 | B | 3 | B | 56.8 |
| 692 | 81 | 6.57 | 1.24 | 1.1 | 2 | 61.5 | B | 3 | B | 48.1 |
| 693 | 77 | 7.25 | 1.29 | 1 | 4 | 154.7 | B | 3 | B | 41.2 |
| 695 | 79 | 4.85 | 1.24 | 1.9 | 6.8 | 159.8 | B | 3 | B | 33.1 |
| 696 | 60 | 4.09 | 0.87 | 1 | 2.9 | 260.4 | B | 3 | B | 22.8 |
| 697 | 68 | 7.76 | 1.17 | 1.9 | 1.7 | 87.7 | B | 3 | B | 46.3 |
| 698 | 68 | 14.22 | 1.1 | 1 | 3.1 | 160.1 | B | 3 | B | 57.7 |
| 699 | 72 | 20.32 | 3.35 | 0 | 2.4 | 203 | B | 3 | B | 47.3 |
| 702 | 73 | 24.75 | 2.36 | 1 | 1.9 | 143.8 | B | 3 | B | 56.8 |
| 704 | 70 | 23.2 | 2.91 | 0.8 | 2.1 | 137.6 | B | 3 | B | 53.7 |

FIG. 7C

| | | | | | | | | | |
|---|---|---|---|---|---|---|---|---|---|
| 705 | 72 | 143.58 | 7.26 | 1.1 | 3.1 | 138.1 | B | 3 | B | 67.8 |
| 706 | 66 | 2.76 | 1.2 | 1.3 | 2.8 | 149.4 | B | 3 | B | 24.6 |
| 708 | 67 | 7.95 | 1.47 | 0.6 | 2.7 | 73.9 | B | 3 | B | 47.9 |
| 709 | 68 | 4.92 | 0.98 | 0 | 1.8 | 121.5 | B | 3 | B | 39.3 |
| 710 | 65 | 4.85 | 1.08 | 0.7 | 2.7 | 111.8 | B | 3 | B | 37.5 |
| 789 | 69 | 2.03 | 0.78 | 0.7 | 1.8 | 73.7 | B | 3 | B | 35.2 |
| 790 | 57 | 3.73 | 1.33 | 0.7 | 3.8 | 124 | B | 3 | B | 27.0 |
| 791 | 76 | 6.73 | 1.12 | 0.9 | 2 | 48.2 | B | 3 | B | 50.8 |
| 792 | 76 | 28.64 | 2.5 | 0.5 | 1.8 | 87.4 | B | 3 | B | 64.3 |
| 793 | 78 | 6.22 | 2 | 1.3 | 3.5 | 117.5 | B | 3 | B | 35.6 |
| 794 | 64 | 3.71 | 1.31 | 2.9 | 4.7 | 132.5 | B | 3 | B | 27.0 |
| 795 | 72 | 11.63 | 1.71 | 1.1 | 2.2 | 178.7 | B | 3 | B | 46.1 |
| 796 | 65 | 17.96 | 1.37 | 1.3 | 2.4 | 52.7 | B | 3 | B | 64.9 |
| 797 | 75 | 10.43 | 2.84 | 0.7 | 4.8 | 113.6 | B | 3 | B | 43.3 |
| 798 | 74 | 41.23 | 38.48 | 0.5 | 3.8 | 94.9 | B | 3 | B | 51.0 |
| 799 | 63 | 6.8 | 0.82 | 0.6 | 6.7 | 247.3 | B | 3 | B | 35.6 |
| 800 | 73 | 22.16 | 1.24 | 0.6 | 2.5 | 73.3 | B | 3 | B | 71.9 |
| 801 | 67 | 3.32 | 1.78 | 0.7 | 1.8 | 71.7 | B | 3 | B | 30.8 |
| 802 | 73 | 7.32 | 1.23 | 0.8 | 3 | 104 | B | 3 | B | 46.1 |
| 803 | 64 | 11.02 | 1.17 | 0.5 | 1 | 49.6 | B | 3 | B | 61.4 |
| 804 | 53 | 6.53 | 0.88 | 0 | 0.9 | 66.3 | B | 3 | B | 49.4 |
| 805 | 74 | 32.48 | 2.06 | 0.5 | 0.6 | 88.4 | B | 3 | B | 70.5 |
| 806 | 72 | 1.6 | 1.4 | 0.6 | 2 | 55.4 | B | 3 | B | 30.6 |
| 807 | 74 | 25.37 | 0.72 | 0.3 | 0 | 46.4 | B | 3 | B | 73.8 |
| 808 | 59 | 12.09 | 1.37 | 0.6 | 2.2 | 96.1 | B | 3 | B | 56.7 |
| 809 | 81 | 33.18 | 0.99 | 0.4 | 2.4 | 57.7 | B | 3 | B | 72.9 |
| 810 | 57 | 6.82 | 3.52 | 1.1 | 0 | 82.9 | B | 3 | B | 31.9 |
| 811 | 67 | 5.96 | 1.47 | 1.7 | 1.4 | 27.9 | B | 3 | B | 44.1 |
| 812 | 62 | 34.72 | 2.04 | 0.9 | 2.4 | 140.5 | B | 3 | B | 67.4 |
| 813 | 69 | 17.22 | 1.27 | 1 | 1.9 | 62.2 | B | 3 | B | 66.0 |
| 814 | 65 | 12.68 | 1.12 | 0.7 | 1.8 | 65 | B | 3 | B | 63.4 |
| 815 | 74 | 9.15 | 0.95 | 0.3 | 1 | 120.8 | B | 3 | B | 54.6 |
| 816 | 74 | 33.25 | 2.46 | 0.4 | 2.7 | 161.8 | B | 3 | B | 63.6 |
| 817 | 69 | 4.2 | 0.95 | 0.5 | 3.6 | 108.8 | B | 3 | B | 38.0 |
| 818 | 77 | 9.85 | 3.13 | 1.6 | 3.3 | 62.7 | B | 3 | B | 43.7 |
| 819 | 61 | 2 | 0.86 | 1 | 2.6 | 105.5 | B | 3 | B | 27.6 |
| 820 | 54 | 9.46 | 0.38 | 0.5 | 0.3 | 85.6 | B | 3 | B | 65.9 |
| 821 | 71 | 5.9 | 0.97 | 0.9 | 2.6 | 125.3 | B | 3 | B | 42.2 |
| 822 | 60 | 8.85 | 13.03 | 0.7 | 2.1 | 81.9 | B | 3 | B | 36.5 |
| 823 | 72 | 7.49 | 1.9 | 0.6 | 3.6 | 149.9 | B | 3 | B | 37.2 |
| 824 | 61 | 34.12 | 16.12 | 1.2 | 2.3 | 99.7 | B | 3 | B | 47.6 |
| 825 | 75 | 8.92 | 1.13 | 0.7 | 2.4 | 88.4 | B | 3 | B | 53.4 |
| 826 | 61 | 5.13 | 1.94 | 0.8 | 2.5 | 151.4 | B | 3 | B | 26.6 |
| 827 | 70 | 11.01 | 1.75 | 0.4 | 3.5 | 146.6 | B | 3 | B | 48.0 |
| 828 | 61 | 53.63 | 1.69 | 0.8 | 2.7 | 113 | B | 3 | B | 70.5 |
| 829 | 55 | 4.94 | 1.6 | 0.5 | 1.1 | 182 | B | 3 | B | 24.5 |
| 830 | 65 | 64.16 | 0.59 | 0.2 | 2.4 | 142.8 | B | 3 | B | 71.4 |
| 831 | 80 | 3.58 | 0.52 | 0 | 0.9 | 89.8 | B | 3 | B | 46.0 |
| 832 | 59 | 17.4 | 0.99 | 0.6 | 3 | 140.4 | B | 3 | B | 66.3 |
| 833 | 68 | 790.46 | 41.76 | 1.2 | 2.1 | 60.4 | B | 3 | B | 71.4 |
| 834 | 63 | 25.86 | 1.42 | 0.7 | 1.9 | 162.9 | B | 3 | B | 67.0 |
| 835 | 66 | 50.54 | 3.02 | 0.8 | 2 | 38.1 | B | 3 | B | 73.1 |
| 836 | 64 | 52.21 | -2.47 | 1.1 | 3.8 | 173 | B | 3 | B | 65.5 |

FIG. 7D

| | | | | | | | | | | |
|---|---|---|---|---|---|---|---|---|---|---|
| 837 | 72 | 12.63 | 2.42 | 1.3 | 1.9 | 71.7 | B | 3 | B | 49.8 |
| 838 | 60 | 19.02 | 1.47 | 1.2 | 1.3 | 68.4 | B | 3 | B | 64.0 |
| 839 | 72 | 50.75 | 22.69 | 0 | 2.9 | 87.5 | B | 3 | B | 54.3 |
| 840 | 63 | 18.86 | 1.82 | 0.9 | 1.1 | 76.2 | B | 3 | B | 61.0 |
| 841 | 65 | 9.77 | 1.76 | 0.6 | 2.6 | 80.9 | B | 3 | B | 49.3 |
| 842 | 76 | 10.63 | 2.06 | 1.2 | 2 | 55.5 | B | 3 | B | 50.8 |
| 843 | 73 | 11.25 | 1.43 | 0.6 | 2.3 | 60.7 | B | 3 | B | 58.3 |
| 844 | 71 | 146.44 | 2.9 | 0.3 | 0.7 | 156.7 | B | 3 | B | 70.4 |
| 845 | 65 | 10.28 | 1.58 | 0.9 | 2.8 | 114.5 | B | 3 | B | 48.4 |
| 846 | 68 | 46.72 | 3.12 | 1.1 | 2.8 | 105.8 | B | 3 | B | 66.1 |
| 847 | 70 | 22.1 | 3.5 | 1 | 4 | 211.8 | B | 3 | B | 45.2 |
| 848 | 76 | 22.23 | 2.63 | 0.8 | 3.5 | 103.8 | B | 3 | B | 56.5 |
| 849 | 81 | 20.94 | 2.21 | 0.9 | 3.1 | 152.3 | B | 3 | B | 54.5 |
| 850 | 67 | 55.47 | 6.6 | 2.1 | 2.1 | 88.6 | B | 3 | B | 54.1 |
| 851 | 60 | 12.63 | 3.16 | 1 | 2.3 | 92.1 | B | 3 | B | 45.5 |
| 852 | 50 | 10.33 | 1.77 | 1.6 | 0.9 | 112 | B | 3 | B | 42.3 |
| 853 | 55 | 19.38 | 1.17 | 1.4 | 3.3 | 193.9 | B | 3 | B | 58.8 |
| 854 | 66 | 25.14 | 17.38 | 1.5 | 2.5 | 85.9 | B | 3 | B | 45.4 |
| 855 | 64 | 5.42 | 1.41 | 3.4 | 3.3 | 161 | B | 3 | B | 29.6 |
| 856 | 69 | 7.97 | 1.61 | 0.8 | 2.8 | 58.1 | B | 3 | B | 48.0 |
| 857 | 67 | 14.04 | 3.1 | 1.6 | 3.5 | 141.2 | B | 3 | B | 42.2 |
| 858 | 62 | 2.87 | 1.34 | 0.5 | 2.8 | 84.7 | B | 3 | B | 29.5 |
| 860 | 63 | 6.38 | 1.04 | 0.6 | 2 | 90.8 | B | 3 | B | 45.2 |
| 861 | 72 | 53.16 | 4.07 | 0.9 | 3.5 | 86.8 | B | 3 | B | 66.0 |
| 862 | 64 | 12.15 | 1.19 | 0.6 | 4.1 | 180 | B | 3 | B | 52.8 |
| 859* | 65 | 44.32 | 28.31 | 46.2 | 2.7 | 108.7 | B | 3 | B | 40.6 |
| 714 | 68 | 30.72 | 3.83 | 0.3 | 6.1 | 318.2 | C | 3 | C | 46.1 |
| 718 | 77 | 18.58 | 1.75 | 1.2 | 3 | 112.4 | C | 3 | C | 57.8 |
| 720 | 80 | 40.38 | 3.27 | 1.3 | 3.5 | 34.1 | C | 3 | C | 66.0 |
| 723 | 59 | 332.64 | 21.75 | 0.7 | 2.9 | 176 | C | 3 | C | 63.5 |
| 724 | 67 | 42.76 | 3.11 | 0.7 | 3.8 | 84 | C | 3 | C | 67.7 |
| 727 | 71 | 49.33 | 5.67 | 1.1 | 4.3 | 99.9 | C | 3 | C | 58.4 |
| 729 | 79 | 7.65 | 0.49 | 0.5 | 3.1 | 195 | C | 3 | C | 52.9 |
| 734 | 79 | 2722.4 | 566.92 | 6.4 | 3.6 | 111.8 | C | 3 | C | 49.2 |
| 738 | 77 | 78.03 | 4.21 | 0.9 | 6.2 | 201.9 | C | 3 | C | 65.2 |
| 741 | 71 | 6.98 | 0.86 | 1.3 | 2.5 | 119 | C | 3 | C | 46.9 |
| 776 | 67 | 275.16 | 132.2 | 0.7 | 2.3 | 198.5 | C | 3 | C | 43.3 |
| 777 | 60 | 7.32 | 1.77 | 1.5 | 6.1 | 172.5 | C | 3 | C | 31.4 |
| 778 | 74 | 15.29 | 0.6 | 0.7 | 1.4 | 102.5 | C | 3 | C | 68.7 |
| 863 | 51 | 2.25 | 0.67 | 0.7 | 0.8 | 82.5 | C | 3 | C | 29.9 |
| 864 | 71 | 34.66 | 7.36 | 0.6 | 1.5 | 34.7 | C | 3 | C | 59.7 |
| 865 | 65 | 1.5 | 1.4 | 0.8 | 4.9 | 191.4 | C | 3 | C | 14.9 |
| 915 | 81 | 71.36 | 1.48 | 0.7 | 12 | 275 | C | 3 | C | 61.5 |
| 916 | 89 | 23.43 | 2.21 | 0.9 | 2.8 | 121.6 | C | 3 | C | 57.6 |
| 917 | 77 | 69.19 | 12.95 | 1.6 | 2 | 82.4 | C | 3 | C | 53.6 |
| 918 | 63 | 176.84 | 6.88 | 0.6 | 2.1 | 99.5 | C | 3 | C | 71.8 |
| 919 | 69 | 92.76 | 4.6 | 1 | 2.5 | 89.5 | C | 3 | C | 70.9 |
| 920 | 73 | 60.67 | 5.85 | 0.7 | 2.7 | 79.2 | C | 3 | C | 64.1 |
| 921 | 77 | 89.95 | 3.71 | 0 | 4.5 | 56.1 | C | 3 | C | 75.2 |
| 922 | 85 | 85.69 | 2.58 | 1.5 | 4.5 | 75.8 | C | 3 | C | 69.1 |
| 923 | 74 | 12.37 | 2.59 | 0.8 | 4.5 | 200.1 | C | 3 | C | 41.0 |
| 924 | 85 | 0 | 0.57 | 1.2 | 2.9 | 104.9 | C | 3 | C | 28.5 |
| 925 | 71 | 8.88 | 0.6 | 0.5 | 2.7 | 52.3 | C | 3 | C | 65.4 |

FIG. 7E

| | | | | | | | | | |
|---|---|---|---|---|---|---|---|---|---|
| 926 | 83 | 62.44 | 2.79 | 0.5 | 1.5 | 204.5 | C | 3 | C | 67.2 |
| 927 | 78 | 26.73 | 2.45 | 0.8 | 4.9 | 155.6 | C | 3 | C | 57.5 |
| 928 | 53 | 6.25 | 6.55 | 1 | 1.5 | 69.7 | C | 3 | C | 29.5 |
| 929 | 90 | 35.29 | 3.26 | 0 | 2.5 | 74 | C | 3 | C | 65.0 |
| 930 | 81 | 45.46 | 21.05 | 0 | 2.1 | 94.3 | C | 3 | C | 54.1 |
| 931 | 75 | 31.66 | 6.53 | 0 | 4.4 | 191.4 | C | 3 | C | 48.9 |
| 932 | 69 | 39.93 | 1.58 | 1 | 2.2 | 89 | C | 3 | C | 71.4 |
| 743 | 86 | 450.13 | 427.6 | 9.5 | 1.2 | 65.6 | | 3 | D | 48.4 |
| 747 | 74 | 345.62 | 70.55 | 2.2 | 3.8 | 219.8 | | 3 | D | 42.5 |
| 748 | 67 | 2000 | 26.31 | 1.3 | 2.4 | 167.6 | | 3 | D | 65.0 |
| 749 | 78 | 0 | 0.63 | 0.9 | 3.4 | 94.4 | | 3 | D | 28.3 |
| 750 | 78 | 155.97 | 7.36 | 1.3 | 1.7 | 97.4 | | 3 | D | 69.2 |
| 751 | 84 | 85.38 | 2.88 | 0.6 | 1.5 | 85.2 | | 3 | D | 72.8 |
| 756 | 76 | 29.84 | 20.62 | 1 | 6.2 | 195.1 | | 3 | D | 40.8 |
| 757 | 72 | 44.55 | 11.14 | 1.4 | 1.4 | 105.1 | | 3 | D | 50.6 |
| 760 | 64 | 16.95 | 2.05 | 0.9 | 1.1 | 77.7 | | 3 | D | 57.1 |
| 764 | 77 | 149.7 | 5.81 | 1.7 | 4.5 | 114 | | 3 | D | 65.7 |
| 765 | 65 | 2343.6 | 159.5 | 1.2 | 1.4 | 75.2 | | 3 | D | 66.9 |
| 770 | 76 | 10.35 | 1.1 | 1.1 | 3.5 | 122.9 | | 3 | D | 53.4 |
| 779 | 77 | 33.38 | 2.27 | 1.3 | 2.3 | 59 | | 3 | D | 67.0 |
| 780 | 85 | 22.2 | 2.42 | 1.2 | 2.7 | 148.7 | | 3 | D | 52.6 |
| 781 | 84 | 123.26 | 2.83 | 0.9 | 1.6 | 54.3 | | 3 | D | 72.6 |
| 782 | 67 | 23.7 | 1.75 | 0.8 | 1.4 | 93.1 | | 3 | D | 65.5 |
| 783 | 81 | 30.96 | 1.3 | 0.9 | 2.2 | 52.5 | | 3 | D | 71.4 |
| 784 | 82 | 118.9 | 47.38 | 0.8 | 1.1 | 104.6 | | 3 | D | 51.9 |
| 785 | 80 | 251.26 | 2.65 | 1.1 | 2.7 | 58.1 | | 3 | D | 71.7 |
| 786 | 88 | 48.35 | 2.84 | 3.6 | 2.3 | 43.1 | | 3 | D | 66.4 |
| 787 | 71 | 236.5 | 35.43 | 1.4 | 1.3 | 44.3 | | 3 | D | 58.3 |
| 788 | 75 | 61.71 | 1.21 | 1 | 0.9 | 84 | | 3 | D | 71.2 |
| 933 | 72 | 191.66 | 85.79 | 1 | 4.5 | 101 | | 3 | D | 49.9 |
| 934 | 91 | 13.67 | 1.28 | 0.8 | 2.8 | 130.4 | | 3 | D | 56.8 |
| 935 | 80 | 236.01 | 116.27 | 0.9 | 3.5 | 136.6 | | 3 | D | 48.5 |
| 936 | 74 | 197.49 | 11.19 | 1.5 | 2.3 | 236.5 | | 3 | D | 59.6 |
| 937 | 78 | 231.32 | 75.89 | 1 | 4.1 | 160.3 | | 3 | D | 47.7 |
| 938 | 74 | 530.07 | 15.46 | 1.7 | 1.7 | 99.7 | | 3 | D | 66.7 |
| 939 | 57 | 742.27 | 83.76 | 0.7 | 1 | 56.5 | | 3 | D | 62.5 |
| 940 | 80 | 162.79 | 6.79 | 0.3 | 4 | 94.8 | | 3 | D | 73.5 |
| 941 | 74 | 3475.3 | 72.76 | 18.3 | 0 | 41.2 | | 3 | D | 67.4 |
| 942 | 65 | 2093.3 | 53.84 | 8.8 | 1.8 | 126.4 | | 3 | D | 62.7 |
| 943 | 88 | 39.37 | 1.62 | 0.5 | 2.9 | 59.1 | | 3 | D | 72.8 |
| 944 | 75 | 223.71 | 10.98 | 0.8 | 2.7 | 63.3 | | 3 | D | 73.1 |
| 945 | 53 | 13.43 | 1.91 | 1.5 | 1.4 | 132.8 | | 3 | D | 46.5 |
| 946 | 62 | 475.53 | 4.31 | 1.2 | 1.7 | 148.9 | | 3 | D | 66.4 |
| 947 | 84 | 26.59 | 2.83 | 1.2 | 3.5 | 62.2 | | 3 | D | 59.2 |
| 503 | 68 | 1.08 | 1.14 | 2.9 | 1.7 | 51.3 | normal | 5 | | 26.6 |
| 504 | 39 | 0.73 | 0.69 | 1.1 | 2.2 | 105.5 | normal | 5 | | 14.3 |
| 505 | 61 | 0.94 | 1.29 | 0.7 | 3.1 | 97.8 | normal | 5 | | 19.3 |
| 506 | 57 | 2.54 | 1.39 | 0.9 | 3.6 | 163.4 | normal | 5 | | 18.6 |
| 510 | 49 | 2.07 | 1.38 | 1.1 | 5 | 166.9 | normal | 5 | | 14.6 |
| 512 | 47 | 0.65 | 0.73 | 0.7 | 1.6 | 82.9 | normal | 5 | | 18.3 |
| 513 | 60 | 0.7 | 0.96 | 1.4 | 4.1 | 205.4 | normal | 5 | | 12.0 |
| 514 | 46 | 1.41 | 0.88 | 0 | 2 | 233.5 | normal | 5 | | 11.0 |
| 517 | 52 | 1.47 | 1.13 | 0.7 | 2.5 | 92.5 | normal | 5 | | 20.2 |

FIG. 7F

| | | | | | | | | | |
|---|---|---|---|---|---|---|---|---|---|
| 981 | 43 | 0.79 | 0.92 | 0.6 | 3.8 | 285.7 | normal | 5 | 7.9 |
| 982 | 46 | 1.13 | 1.05 | 1.2 | 1 | 171.6 | normal | 5 | 12.1 |
| 983 | 61 | 0.88 | 0.69 | 1 | 1.6 | 85 | normal | 5 | 26.1 |
| 984 | 42 | 1.15 | 1.74 | 0.9 | 2.5 | 241.7 | normal | 5 | 8.3 |
| 985 | 61 | 0 | 1.39 | 0.7 | 1.5 | 64.4 | normal | 5 | 17.5 |
| 986 | 41 | 0.64 | 1.03 | 0.6 | 2.8 | 136.3 | normal | 5 | 10.6 |
| 987 | 56 | 0.88 | 0.7 | 0.9 | 1.6 | 77.9 | normal | 5 | 24.6 |
| 988 | 45 | 1.52 | 1.35 | 0.6 | 2.9 | 152.4 | normal | 5 | 12.7 |
| 989 | 52 | 0.77 | 0.53 | 0.7 | 0.9 | 127.7 | normal | 5 | 19.2 |
| 990 | 53 | 2.45 | 1.14 | 2.4 | 2.2 | 148 | normal | 5 | 19.5 |
| 991 | 39 | 0.7 | 0.98 | 0.7 | 3.2 | 191.1 | normal | 5 | 8.9 |
| 992 | 51 | 1.1 | 1.06 | 1.2 | 3.5 | 240.9 | normal | 5 | 10.3 |
| 993 | 60 | 1.96 | 0.81 | 0.3 | 1 | 53.3 | normal | 5 | 33.8 |
| 994 | 50 | 0.62 | 1.08 | 0.4 | 2.8 | 146.3 | normal | 5 | 11.8 |
| 995 | 51 | 1.11 | 0.56 | 0.4 | 3.6 | 269.1 | normal | 5 | 10.9 |
| 996 | 68 | 0.65 | 1.05 | 0.5 | 3.9 | 196.8 | normal | 5 | 13.8 |
| 997 | 11 | 3.22 | 0.86 | 0.8 | 2.5 | 95.9 | normal | 5 | 17.7 |
| 998 | 60 | 0.78 | 0.67 | 0.6 | 0.9 | 81.5 | normal | 5 | 26.0 |
| 999 | 53 | 0.7 | 0.68 | 0 | 1.6 | 74.9 | normal | 5 | 22.6 |
| 1000 | 56 | 1.19 | 0.83 | 0 | 1.6 | 157 | normal | 5 | 17.0 |
| 1001 | 47 | 0.73 | 0.92 | 1 | 2.7 | 120.5 | normal | 5 | 14.0 |
| 1002 | 48 | 1.03 | 0.92 | 0.5 | 1.8 | 212.6 | normal | 5 | 10.7 |
| 1003 | 39 | 0.86 | 0.91 | 0.4 | 0.9 | 181.5 | normal | 5 | 9.8 |
| 1004 | 61 | 0.8 | 0.36 | 0.5 | 1.9 | 104.6 | normal | 5 | 28.1 |
| 1005 | 50 | 0.52 | 0.49 | 0.7 | 1.1 | 106.2 | normal | 5 | 19.2 |
| 1006 | 39 | 0.97 | 1.27 | 0.6 | 0.6 | 279 | normal | 5 | 7.7 |
| 1007 | 49 | 0.51 | 0.74 | 1 | 1.7 | 106.3 | normal | 5 | 16.1 |
| 1008 | 62 | 0.72 | 0.69 | 1.1 | 2 | 113.2 | normal | 5 | 22.4 |
| 1009 | 41 | 0 | 0.93 | 0.6 | 0.9 | 75.6 | normal | 5 | 12.2 |
| 1010 | 49 | 0.61 | 1.17 | 0.4 | 1.9 | 128.6 | normal | 5 | 12.2 |
| 1011 | 41 | 0.58 | 1.24 | 0.5 | 1.8 | 118.9 | normal | 5 | 10.4 |
| 1012 | 55 | 0.84 | 0.44 | 1 | 1.8 | 103.8 | normal | 5 | 24.6 |
| 1013 | 50 | 1.69 | 1.23 | 0.9 | 1.4 | 132.2 | normal | 5 | 16.5 |
| 1014 | 51 | 2.35 | 0.87 | 0.9 | 1.3 | 111.2 | normal | 5 | 24.7 |
| 1015 | 49 | 0.53 | 1.19 | 0.8 | 2.3 | 104.6 | normal | 5 | 13.1 |
| 1016 | 72 | 1.03 | 0.94 | 1.2 | 2 | 87.8 | normal | 5 | 27.8 |
| 1017 | 53 | 1.06 | 1.22 | 0.8 | 1.7 | 87.5 | normal | 5 | 18.3 |
| 1018 | 63 | 3.25 | 0.97 | 0.8 | 2.6 | 173.8 | normal | 5 | 25.9 |
| 1019 | 45 | 0 | 0.62 | 0.6 | 0.6 | 97.6 | normal | 5 | 14.1 |
| 1020 | 60 | 0.74 | 0.76 | 0.8 | 2.8 | 184.9 | normal | 5 | 14.8 |
| 1021 | 41 | 1.41 | 0.86 | 0.4 | 0.8 | 111.1 | normal | 5 | 16.4 |
| 1022 | 51 | 0.83 | 0.74 | 0.5 | 0.6 | 82.6 | normal | 5 | 21.2 |
| 1023 | 41 | 1.47 | 0.78 | 0.6 | 1.8 | 120 | normal | 5 | 16.6 |
| 1024 | 46 | 2.22 | 0.95 | 0.5 | 1 | 73.8 | normal | 5 | 25.1 |
| 1025 | 47 | 1.03 | 0.95 | 0.6 | 1.5 | 104.7 | normal | 5 | 16.5 |
| | 48 | 1.6 | 0.81 | 0 | 1.2 | 150.6 | normal | 5 | 16.9 |

FIG. 7G

| | | | | | | | | | |
|---|---|---|---|---|---|---|---|---|---|
| 521 | 57 | 0.74 | 0.74 | 0 | 2.4 | 282 | normal | 5 | 9.4 |
| 522 | 65 | 0.58 | 1.21 | 0 | 1.7 | 113.8 | normal | 5 | 18.5 |
| 523 | 70 | 3.58 | 1.52 | 1.4 | 2.8 | 176.6 | normal | 5 | 23.9 |
| 524 | 41 | 0.65 | 0.97 | 0.7 | 1.4 | 169.7 | normal | 5 | 9.7 |
| 525 | 53 | 0.92 | 1.15 | 0.8 | 2.8 | 219.4 | normal | 5 | 10.2 |
| 527 | 37 | 0.78 | 1.04 | 0 | 1.1 | 110.6 | normal | 5 | 11.4 |
| 528 | 62 | 0.55 | 0.92 | 1.4 | 5.8 | 126.3 | normal | 5 | 17.0 |
| 529 | 42 | 0.56 | 0.95 | 0.7 | 0 | 110.4 | normal | 5 | 12.3 |
| 531 | 64 | 0.71 | 0.56 | 0.9 | 3 | 92.1 | normal | 5 | 27.2 |
| 532 | 25 | 0 | 0.88 | 1 | 1.3 | 201.6 | normal | 5 | 7.0 |
| 534 | 41 | 0.63 | 0.83 | 0.7 | 3.9 | 153 | normal | 5 | 10.7 |
| 535 | 40 | 0.69 | 0.95 | 1.4 | 3.6 | 207.5 | normal | 5 | 9.0 |
| 536 | 64 | 0.98 | 0.99 | 0.8 | 3.9 | 114.9 | normal | 5 | 21.4 |
| 537 | 41 | 0.68 | 0.91 | 0.9 | 2.7 | 166.2 | normal | 5 | 10.2 |
| 538 | 68 | 2.13 | 1.1 | 1 | 3.5 | 47.7 | normal | 5 | 34.2 |
| 539 | 69 | 1.73 | 0.96 | 1.1 | 2.9 | 40.8 | normal | 5 | 34.8 |
| 553 | 48 | 1.39 | 1.18 | 1.1 | 2.5 | 329.4 | normal | 5 | 9.3 |
| 554 | 46 | 2.11 | 0.95 | 1.2 | 2.3 | 86.7 | normal | 5 | 23.0 |
| 565 | 46 | 1.14 | 1.47 | 0 | 3.4 | 267.3 | normal | 5 | 8.4 |
| 566 | 48 | 1.52 | 0.9 | 1 | 3.4 | 105 | normal | 5 | 19.6 |
| 948 | 43 | 1.03 | 1.05 | 0.2 | 1.2 | 99.5 | normal | 5 | 14.8 |
| 949 | 44 | 0 | 0.74 | 0.6 | 2.2 | 121.1 | normal | 5 | 11.3 |
| 950 | 52 | 1.1 | 0.69 | 0.5 | 3.5 | 136.8 | normal | 5 | 18.1 |
| 951 | 54 | 0.69 | 1.13 | 0.3 | 2.6 | 176.2 | normal | 5 | 11.3 |
| 952 | 42 | 0.8 | 0.9 | 0.4 | 3.3 | 158.9 | normal | 5 | 10.9 |
| 953 | 51 | 0.85 | 0.52 | 0.8 | 2 | 98.5 | normal | 5 | 22.2 |
| 954 | 43 | 0.87 | 0.9 | 0.7 | 2.2 | 110.9 | normal | 5 | 14.2 |
| 955 | 42 | 0.53 | 0.72 | 0.6 | 5.5 | 390.4 | normal | 5 | 7.3 |
| 956 | 46 | 1.18 | 0.63 | 1.8 | 3.4 | 215.2 | normal | 5 | 12.9 |
| 957 | 42 | 0.81 | 0.89 | 0.7 | 1.9 | 134 | normal | 5 | 12.3 |
| 958 | 47 | 1.39 | 0.58 | 1.7 | 3.2 | 247.9 | normal | 5 | 12.9 |
| 959 | 48 | 0 | 0.34 | 0.4 | 2.5 | 257 | normal | 5 | 8.3 |
| 960 | 54 | 0.65 | 0.77 | 0.4 | 1.3 | 96.2 | normal | 5 | 19.7 |
| 961 | 56 | 3.6 | 1.01 | 0.2 | 0 | 201.5 | normal | 5 | 22.7 |
| 962 | 63 | 2.63 | 0.56 | 0.5 | 3.1 | 107.9 | normal | 5 | 35.0 |
| 963 | 50 | 1.4 | 1.03 | 0.8 | 1.6 | 157.5 | normal | 5 | 14.8 |
| 964 | 53 | 1.48 | 1.02 | 0 | 1.4 | 61.3 | normal | 5 | 25.2 |
| 965 | 56 | 0 | 0.67 | 0.7 | 5.4 | 147.8 | normal | 5 | 13.6 |
| 966 | 43 | 0 | 0.72 | 0.6 | 2.3 | 167.1 | normal | 5 | 9.1 |
| 967 | 43 | 0.92 | 0.43 | 0.9 | 2.1 | 119.7 | normal | 5 | 18.3 |
| 968 | 50 | 1.18 | 0.55 | 0.8 | 2.1 | 124.8 | normal | 5 | 20.7 |
| 969 | 51 | 0.86 | 0.72 | 0.9 | 2.8 | 131.4 | normal | 5 | 16.8 |
| 970 | 62 | 1.5 | 0.9 | 1 | 4.2 | 116.3 | normal | 5 | 23.9 |
| 971 | 44 | 1.84 | 0.92 | 0.8 | 1.2 | 109 | normal | 5 | 19.3 |
| 972 | 42 | 2 | 1.41 | 0.3 | 3.2 | 332 | normal | 5 | 9.7 |
| 973 | 43 | 0 | 0.96 | 1.3 | 3.1 | 192.2 | normal | 5 | 8.0 |
| 974 | 63 | 1.64 | 0.86 | 1 | 2.9 | 44.5 | normal | 5 | 33.1 |
| 975 | 48 | 1.05 | 0.77 | 1 | 1.7 | 92.8 | normal | 5 | 19.7 |
| 976 | 48 | 1.53 | 1.16 | 0.7 | 1.6 | 113.1 | normal | 5 | 17.0 |
| 977 | 40 | 0.72 | 0.98 | 0.4 | 0.5 | 52 | normal | 5 | 16.5 |
| 978 | 35 | 0.91 | 0.97 | 0.6 | 0.8 | 185.8 | normal | 5 | 9.2 |
| 979 | 46 | 0.93 | 0.89 | 0.6 | 2.4 | 180.1 | normal | 5 | 11.4 |
| 980 | 42 | 1.25 | -1.06 | 0.6 | 2.6 | 175.4 | normal | 5 | 11.3 |

FIG. 7H

Training Data for Osteoporosis
Neural Network Diagnostic System

| PATIENT | AGE | CAL | PHOS | ETWO | PROG | TALP | TINTES | PLIVER | SCORE |
|---|---|---|---|---|---|---|---|---|---|
| 1 | 61 | 9.7 | 3.6 | 15 | 0.2 | 82 | 0 | 67.317 | 0.645 |
| 2 | 55 | 9.2 | 3.9 | 83 | 7.9 | 31 | 3.7 | 49.032 | 0.747 |
| 3 | 33 | 9.4 | 3.6 | 12 | 0.1 | 39 | 2.8 | 62.821 | 0.819 |
| 4 | 43 | 8.5 | 4 | 4 | 0.3 | 39 | 2.6 | 50.513 | 0.841 |
| 5 | 58 | 9.5 | 3.5 | 40 | 0.1 | 75 | 0 | 78.267 | 0.660 |
| 6 | 48 | 9.6 | 3.8 | 145 | 7.5 | 49 | 0 | 59.388 | 0.679 |
| 7 | 56 | 8.6 | 3.8 | 43 | 0.1 | 48 | 0 | 60.833 | 0.698 |
| 8 | 36 | 9.4 | 4.1 | 106 | 6 | 77 | 0 | 54.156 | 0.819 |
| 9 | 32 | 8.5 | 3.6 | 18 | 0.7 | 52 | 0 | 51.538 | 0.810 |
| 10 | 33 | 9.4 | 3.6 | 65 | 2.4 | 63 | 4.6 | 70.794 | 0.815 |
| 11 | 74 | 9.2 | 4.2 | 13 | 0.2 | 70 | 0 | 62.571 | 0.619 |
| 12 | 41 | 8.8 | 4.1 | 43 | 0.7 | 70 | 13.1 | 48.000 | 0.890 |
| 13 | 28 | 9.1 | 3 | 84 | 0.3 | 76 | 7 | 52.763 | 0.802 |
| 14 | 44 | 9.1 | 3.3 | 176 | 0.6 | 82 | 10.3 | 62.805 | 1.011 |
| 15 | 62 | 9.1 | 3.4 | 90 | 0.2 | 32 | 0 | 40.625 | 0.693 |
| 16 | 36 | 9.6 | 3.8 | 59 | 0.1 | 39 | 0 | 66.154 | 0.822 |
| 17 | 60 | 8.9 | 3.4 | 129 | 0.1 | 64 | 0 | 78.125 | 0.668 |
| 18 | 42 | 9.3 | 3.8 | 35 | 0.8 | 43 | 0 | 39.070 | 0.814 |
| 19 | 35 | 9.4 | 3.7 | 58 | 0.2 | 39 | 0 | 55.128 | 0.828 |
| 20 | 47 | 9.1 | 5.2 | 42 | 1.4 | 50 | 7.6 | 60.200 | 0.762 |
| 21 | 46 | 9 | 4.5 | 95 | 7 | 52 | 10.4 | 60.192 | 0.886 |
| 22 | 37 | 9.3 | 3.4 | 231 | 0.2 | 60 | 0 | 84.667 | 0.779 |
| 23 | 30 | 9.1 | 4.2 | 5 | 0.2 | 61 | 11.3 | 52.459 | 0.837 |
| 24 | 45 | 9.2 | 3.6 | 63 | 2.3 | 44 | 5.4 | 64.318 | 0.766 |
| 25 | 42 | 9.2 | 3.5 | 139 | 0.4 | 44 | 0 | 72.045 | 0.773 |
| 26 | 61 | 9.8 | 4 | 22 | 0.3 | 70 | 0 | 49.571 | 0.669 |
| 27 | 64 | 8.8 | 4.1 | 17 | 0.2 | 73 | 5.7 | 65.068 | 0.646 |
| 28 | 79 | 10.2 | 3.9 | 13 | 0.1 | 67 | 0 | 53.731 | 0.602 |
| 29 | 33 | 8.5 | 2.9 | 20 | 0.4 | 39 | 5.2 | 47.949 | 0.791 |
| 30 | 41 | 9 | 2.5 | 120 | 0.8 | 56 | 0 | 55.893 | 0.770 |
| 31 | 50 | 9 | 3 | 79 | 0.7 | 49 | 0 | 48.367 | 0.721 |
| 32 | 46 | 9.5 | 4.1 | 22 | 0.3 | 58 | 4 | 46.034 | 0.729 |
| 33 | 51 | 9.2 | 3.2 | 162 | 0.3 | 58 | 0 | 50.172 | 0.716 |
| 34 | 45 | 9 | 3.1 | 44 | 2 | 42 | 0 | 65.714 | 0.733 |
| 35 | 45 | 9.3 | 3.8 | 123 | 12.8 | 66 | 18.3 | 54.848 | 0.965 |
| 36 | 32 | 9.3 | 3.8 | 40 | 0.6 | 40 | 4.3 | 39.000 | 0.849 |
| 37 | 51 | 8.9 | 3.6 | 71 | 2.8 | 70 | 7.1 | 55.429 | 0.713 |
| 38 | 29 | 9.2 | 4 | 117 | 16.5 | 30 | 0 | 57.000 | 0.894 |
| 39 | 31 | 9.3 | 4 | 93 | 0.3 | 41 | 0 | 25.610 | 0.885 |
| 40 | 69 | 10 | 4.2 | 15 | 0.3 | 110 | 36.4 | 45.364 | 0.615 |
| 41 | 29 | 9.2 | 3.9 | 12 | 0.1 | 147 | 18.1 | 54.694 | 0.770 |
| 42 | 67 | 9.3 | 4.7 | 3 | 0.2 | 65 | 2.9 | 48.000 | 0.663 |
| 43 | 42 | 8.8 | 3 | 57 | 2.5 | 55 | 3.9 | 31.091 | 0.827 |
| 44 | 52 | 9.6 | 3.8 | 118 | 0.6 | 53 | 3.8 | 63.774 | 0.733 |
| 45 | 51 | 10 | 4.4 | 52 | 0.3 | 62 | 8.6 | 39.516 | 0.745 |
| 46 | 46 | 8.8 | 3.6 | 73 | 3 | 45 | 0 | 26.444 | 0.788 |
| 47 | 46 | 8.9 | 4.4 | 14 | 0.4 | 64 | 0 | 62.031 | 0.783 |

FIG. 8A

| PATIENT | AGE | CAL | PHOS | ETWO | PROG | TALP | TINTES | PLIVER | SCORE |
|---|---|---|---|---|---|---|---|---|---|
| 48 | 45 | 9.1 | 4.5 | 206 | 0.2 | 84 | 19.6 | 45.357 | 0.843 |
| 49 | 81 | 9.3 | 4.2 | 4 | 0.3 | 66 | 7.4 | 64.848 | 0.594 |
| 50 | 32 | 9 | 2.5 | 25 | 1.4 | 56 | 0 | 68.929 | 0.763 |
| 51 | 52 | 9.5 | 3.8 | 11 | 0.1 | 49 | 0 | 66.735 | 0.714 |
| 52 | 47 | 8.9 | 4.7 | 15 | 0.2 | 64 | 7 | 66.563 | 0.744 |
| 53 | 60 | 9.2 | 3 | 18 | 0.2 | 101 | 23.8 | 39.604 | 0.622 |
| 54 | 47 | 9.5 | 4.5 | 8 | 0.1 | 72 | 8.2 | 66.389 | 0.702 |
| 55 | 46 | 9.5 | 3.5 | 34 | 10.6 | 67 | 9.8 | 54.925 | 0.767 |
| 56 | 57 | 10.1 | 3.9 | 38 | 0.4 | 120 | 9.6 | 73.083 | 0.649 |
| 57 | 69 | 9.5 | 3.7 | 10 | 0.1 | 91 | 0 | 68.132 | 0.612 |
| 58 | 62 | 8.7 | 3.5 | 13 | 0.2 | 65 | 0 | 52.615 | 0.650 |
| 59 | 73 | 8.9 | 4 | 15 | 0.2 | 102 | 11.1 | 60.294 | 0.594 |
| 60 | 51 | 8.9 | 3.5 | 74 | 4.4 | 51 | 0 | 69.608 | 0.726 |
| 61 | 51 | 9 | 3.7 | 12 | 0.4 | 109 | 0 | 56.330 | 0.667 |
| 62 | 63 | 9.5 | 4.7 | 9 | 0.3 | 51 | 0 | 51.961 | 0.692 |
| 63 | 77 | 9.3 | 3.2 | 17 | 0.2 | 106 | 10.7 | 51.226 | 0.567 |
| 64 | 63 | 9.2 | 4.1 | 17 | 0.2 | 51 | 7.9 | 31.569 | 0.675 |
| 65 | 73 | 9.6 | 1.1 | 19 | 0.2 | 69 | 0 | 75.217 | 0.576 |
| 66 | 83 | 9 | 3.6 | 2 | 0.1 | 57 | 0 | 81.404 | 0.581 |
| 67 | 59 | 8.8 | 3.7 | 24 | 0.1 | 85 | 6.9 | 59.294 | 0.648 |
| 68 | 60 | 8.9 | 4 | 110 | 0.3 | 40 | 0 | 66.500 | 0.706 |
| 69 | 76 | 9.4 | 3.5 | 21 | 0.1 | 54 | 5.8 | 62.593 | 0.604 |
| 70 | 59 | 9.2 | 4.6 | 15 | 0.1 | 60 | 0 | 51.500 | 0.699 |
| 71 | 63 | 9.2 | 3.4 | 121 | 0.1 | 48 | 0 | 140.833 | 0.667 |
| 72 | 63 | 9.4 | 3.2 | 65 | 0.1 | 64 | 8.3 | 62.188 | 0.648 |
| 73 | 76 | 8.9 | 3.8 | 8 | 0 | 91 | 11.8 | 58.132 | 0.587 |
| 74 | 46 | 8.6 | 3.5 | 54 | 7.4 | 73 | 10.1 | 46.301 | 0.993 |
| 75 | 57 | 9.1 | 3.7 | 195 | 0.1 | 61 | 11.4 | 55.410 | 0.695 |
| 76 | 41 | 9.1 | 3.4 | 67 | 3 | 57 | 0 | 68.772 | 0.733 |
| 77 | 61 | 9.9 | 4.3 | 20 | 0.1 | 61 | 8.6 | 57.213 | 0.679 |
| 78 | 25 | 9.1 | 3.3 | 122 | 0.6 | 62 | 0 | 66.935 | 0.821 |
| 79 | 51 | 9.2 | 3.1 | 124 | 7.7 | 79 | 11.1 | 26.835 | 0.704 |
| 80 | 57 | 8.9 | 3.9 | 15 | 0.3 | 84 | 0 | 72.500 | 0.662 |
| 81 | 76 | 8.8 | 3.1 | 12 | 0.2 | 88 | 0 | 86.023 | 0.574 |
| 82 | 64 | 9.3 | 3.4 | 131 | 0.1 | 57 | 4.5 | 55.965 | 0.662 |
| 83 | 61 | 9.4 | 3.5 | 22 | 0.5 | 86 | 9.4 | 60.581 | 0.637 |
| 84 | 42 | 9.3 | 3.4 | 150 | 14.9 | 78 | 0 | 54.744 | 0.699 |
| 85 | 28 | 8.9 | 3.5 | 177 | 9.6 | 46 | 0 | 34.348 | 0.867 |
| 86 | 26 | 9.4 | 4.1 | 139 | 0.2 | 52 | 6.9 | 52.500 | 0.878 |
| 87 | 73 | 9.3 | 3.5 | 0 | 0.2 | 72 | 11.5 | 52.361 | 0.604 |
| 88 | 37 | 9.3 | 3.1 | 55 | 2.2 | 77 | 6.4 | 56.623 | 0.756 |
| 89 | 72 | 9.2 | 4.3 | 4 | 0.2 | 111 | 6.3 | 50.811 | 0.603 |
| 90 | 69 | 9.2 | 2.8 | 14 | 0.1 | 125 | 0 | 75.360 | 0.580 |
| 91 | 88 | 9.1 | 3.3 | 19 | 0.2 | 74 | 0 | 52.027 | 0.554 |
| 92 | 76 | 9 | 3.1 | 13 | 0.1 | 65 | 6.2 | 66.308 | 0.587 |
| 93 | 77 | 8.5 | 3.1 | 10 | 0.1 | 31 | 3.2 | 31.290 | 0.609 |
| 94 | 80 | 9.2 | 2.7 | 15 | 0.1 | 67 | 0 | 72.836 | 0.568 |

FIG. 8B

| PATIENT | AGE | CAL | PHOS | ETWO | PROG | TALP | TINTES | PLIVER | SCORE |
|---|---|---|---|---|---|---|---|---|---|
| 95 | 70 | 8.8 | 4 | 19 | 0.1 | 102 | 7.1 | 67.353 | 0.603 |
| 96 | 52 | 9.7 | 3.3 | 21 | 0.1 | 94 | 20.6 | 43.298 | 0.666 |
| 97 | 76 | 9.3 | 2.4 | 66 | 0.1 | 130 | 0 | 62.769 | 0.563 |
| 98 | 74 | 9.4 | 3.2 | 19 | 0.1 | 85 | 0 | 73.529 | 0.587 |
| 99 | 70 | 9.4 | 4 | 11 | 0.1 | 56 | 0 | 60.714 | 0.639 |
| 100 | 80 | 9.5 | 3.9 | 17 | 0.1 | 77 | 0 | 72.338 | 0.587 |
| 101 | 72 | 9.4 | 3.7 | 5 | 0.1 | 93 | 0 | 79.677 | 0.598 |
| 102 | 74 | 9.6 | 2 | 24 | 0.1 | 88 | 4.9 | 61.364 | 0.563 |
| 103 | 55 | 10.1 | 3.5 | 15 | 0.1 | 68 | 6 | 35.294 | 0.684 |
| 104 | 52 | 9.1 | 4.2 | 11 | 0.2 | 71 | 2.8 | 58.732 | 0.706 |
| 105 | 60 | 9.1 | 3.1 | 29 | 0.3 | 88 | 10.7 | 46.023 | 0.631 |
| 106 | 77 | 9.1 | 4 | 15 | 0.4 | 66 | 5.8 | 68.636 | 0.603 |
| 107 | 46 | 8.8 | 4 | 14 | 0.2 | 44 | 0 | 72.500 | 0.784 |
| 108 | 52 | 8.5 | 3.2 | 14 | 0.2 | 88 | 6.1 | 43.409 | 0.663 |
| 109 | 52 | 8.6 | 3.7 | 10 | 0.1 | 62 | 3.8 | 41.452 | 0.700 |
| 110 | 79 | 9.1 | 3.8 | 13 | 0.2 | 78 | 0 | 71.795 | 0.587 |
| 111 | 66 | 9.5 | 4.4 | 9 | 0.1 | 74 | 0 | 64.189 | 0.652 |
| 112 | 40 | 9.2 | 3.1 | 38 | 0.7 | 51 | 6.8 | 41.961 | 0.758 |
| 113 | 82 | 9.7 | 3.7 | 5 | 0.1 | 70 | 5.8 | 72.714 | 0.579 |
| 114 | 66 | 10 | 4.5 | 9 | 0.1 | 66 | 0 | 67.879 | 0.662 |
| 115 | 62 | 9.3 | 3 | 34 | 0.1 | 63 | 0 | 71.587 | 0.639 |
| 116 | 60 | 8.7 | 3.9 | 14 | 0.1 | 56 | 11.7 | 59.464 | 0.669 |
| 117 | 81 | 8.8 | 3.6 | 17 | 0.2 | 96 | 7.3 | 64.792 | 0.564 |
| 118 | 75 | 9.2 | 3.3 | 11 | 0.2 | 72 | 0 | 61.528 | 0.595 |
| 119 | 66 | 8.9 | 4.5 | 9 | 0.2 | 81 | 0 | 45.062 | 0.651 |
| 120 | 78 | 8.4 | 3.9 | 7 | 0.1 | 71 | 8.5 | 62.676 | 0.591 |
| 121 | 74 | 8.8 | 2.8 | 0 | 0.1 | 62 | 0 | 62.742 | 0.592 |
| 122 | 81 | 8.8 | 3.2 | 10 | 0.1 | 61 | 6.8 | 28.033 | 0.581 |
| 123 | 74 | 10.4 | 3.4 | 11 | 0.2 | 69 | 0 | 48.551 | 0.609 |
| 124 | 82 | 8.8 | 3.4 | 17 | 0.2 | 79 | 0 | 61.772 | 0.569 |
| 125 | 44 | 8.6 | 3.2 | 208 | 0.3 | 120 | 0 | 70.417 | 0.728 |
| 126 | 69 | 8.5 | 4.5 | 18 | 0.1 | 78 | 5.9 | 57.179 | 0.634 |
| 127 | 75 | 8.7 | 3.8 | 9 | 0.2 | 69 | 0 | 66.957 | 0.605 |
| 129 | 74 | 9 | 3.8 | 8 | 0.1 | 80 | 4 | 72.375 | 0.599 |
| 130 | 89 | 8.7 | 2.9 | 32 | 0.2 | 130 | 0 | 68.615 | 0.525 |
| 131 | 77 | 9.5 | 4.2 | 41 | 0.1 | 74 | 6.8 | 69.054 | 0.606 |
| 132 | 72 | 8.9 | 3.5 | 24 | 0.3 | 58 | 0 | 43.621 | 0.620 |
| 133 | 69 | 9.2 | 3.1 | 9 | 0.2 | 94 | 8.4 | 49.468 | 0.597 |
| 134 | 71 | 9 | 6.3 | 5 | 0.1 | 70 | 4.6 | 61.571 | 0.646 |
| 135 | 68 | 9.2 | 3.6 | 11 | 0.1 | 84 | 0 | 72.857 | 0.616 |
| 136 | 85 | 9 | 3.9 | 7 | 0.1 | 71 | 12.6 | 64.366 | 0.571 |
| 137 | 43 | 9.2 | 3.8 | 149 | 0.2 | 46 | 0 | 68.261 | 0.777 |
| 138 | 49 | 9.2 | 2.9 | 73 | 3.3 | 42 | 0 | 57.619 | 0.696 |
| 139 | 41 | 8.6 | 4.1 | 117 | 15.7 | 93 | 0 | 63.656 | 0.716 |
| 140 | 67 | 9 | 3.4 | 93 | 0.1 | 59 | 0 | 73.051 | 0.646 |
| 141 | 50 | 9.8 | 2.1 | 132 | 0.2 | 45 | 3.5 | 42.000 | 0.702 |
| 142 | 70 | 9.2 | 2.7 | 13 | 0.1 | 67 | 0 | 72.985 | 0.600 |

FIG. 8C

| PATIENT | AGE | CAL | PHOS | ETWO | PROG | TALP | TINTES | PLIVER | SCORE |
|---|---|---|---|---|---|---|---|---|---|
| 143 | 66 | 9.4 | 3.3 | 14 | 0.1 | 71 | 0 | 71.690 | 0.625 |
| 144 | 52 | 9 | 3.5 | 53 | 0.3 | 64 | 3.8 | 35.156 | 0.706 |
| 145 | 82 | 8.5 | 3.1 | 15 | 0.1 | 64 | 0 | 49.063 | 0.572 |
| 146 | 64 | 9.6 | 3.6 | 149 | 0.5 | 47 | 8.7 | 58.936 | 0.675 |
| 147 | 65 | 9.1 | 4.6 | 9 | 0.3 | 78 | 0 | 41.154 | 0.661 |
| 148 | 54 | 9.4 | 4.5 | 16 | 0.2 | 96 | 5.7 | 69.583 | 0.683 |
| 149 | 48 | 9.2 | 4.1 | 33 | 0.3 | 143 | 8.7 | 34.895 | 0.708 |
| 150 | 75 | 10 | 3.9 | 10 | 0.2 | 88 | 0 | 39.545 | 0.605 |
| 151 | 57 | 9.4 | 3.9 | 10 | 0.2 | 54 | 3.4 | 51.111 | 0.692 |
| 152 | 47 | 9.4 | 4 | 42 | 0.3 | 65 | 8.6 | 51.846 | 0.739 |
| 153 | 70 | 8.8 | 3.5 | 6 | 0.1 | 65 | 5 | 37.231 | 0.621 |
| 154 | 59 | 9.2 | 4 | 9 | 0.2 | 49 | 4.4 | 47.143 | 0.690 |
| 155 | 60 | 9.2 | 4.1 | 12 | 0.1 | 56 | 2.8 | 60.357 | 0.680 |
| 156 | 49 | 9.1 | 3.6 | 59 | 0.2 | 35 | 0 | 54.571 | 0.762 |
| 157 | 59 | 9.5 | 4.1 | 7 | 0.1 | 92 | 6.5 | 45.978 | 0.660 |
| 158 | 66 | 9.2 | 3.8 | 1 | 0.2 | 46 | 0 | 40.000 | 0.660 |
| 159 | 57 | 9.2 | 4.3 | 16 | 0.2 | 81 | 5.4 | 53.704 | 0.679 |
| 160 | 41 | 10 | 4.6 | 306 | 1.2 | 46 | 0 | 75.217 | 0.763 |
| 161 | 38 | 9.5 | 3.6 | 4 | 0.2 | 68 | 5.1 | 69.265 | 0.758 |
| 162 | 35 | 9.5 | 3.4 | 36 | 0.4 | 57 | 3.3 | 64.561 | 0.785 |

FIG. 8D

Testing Data for Osteoporosis
Diagnostic System

| PATIENT | AGE | CAL | PHOS | ETWO | PROG | TALP | TINTES | PLIVER | SCORE |
|---|---|---|---|---|---|---|---|---|---|
| 123 | 52 | 9.4 | 4.2 | -1 | 0.3 | 61 | 0 | 46 | 0.722 |
| 128 | 27 | 9.8 | 4.4 | -1 | 0.4 | 58 | 0 | 43 | 0.862 |
| 131 | 39 | 9.1 | 3.9 | 156 | 11.5 | 44 | 0 | 59 | 0.820 |
| 173 | 26 | 9.5 | 3.8 | 41 | 0.2 | 98 | 0 | 60 | 0.790 |
| 201 | 30 | 9.1 | 3.5 | 123 | 3.3 | 90 | 0 | 53 | 0.814 |
| 206 | 39 | 9.2 | 2.6 | 50 | 1.5 | 74 | 89 | 42 | 0.729 |
| 213 | 46 | 9.7 | 3.4 | 37 | 0.2 | 90 | 0 | 36 | 0.708 |
| 220 | 46 | 8.8 | 3.4 | 118 | 4.3 | 90 | 9 | 63 | 0.996 |
| 223 | 49 | 9.7 | 3.3 | 72 | 0.4 | 78 | 8.6 | 38 | 0.717 |
| 234 | 38 | 9.5 | 3.2 | 186 | 12.6 | 50 | 0 | 46 | 0.803 |
| 243 | 33 | 9.3 | 4.4 | 65 | 0.3 | 58 | 0 | 40 | 0.857 |
| 244 | 53 | 9.6 | 3.7 | 96 | 0.3 | 58 | 0 | 49 | 0.725 |
| 245 | 30 | 9.5 | 3.2 | -1 | 0.1 | 64 | 0 | 53 | 0.800 |
| 247 | 28 | 9.1 | 3.6 | -1 | 0.3 | 58 | 0 | 50 | 0.821 |
| 249 | 22 | 9.3 | 3.5 | 42 | 0.2 | 98 | 11.1 | 38 | 0.782 |
| 253 | 24 | 9.2 | 3.4 | -1 | 0.3 | 68 | 0 | 63 | 0.797 |
| 254 | 30 | 9.6 | 4 | 143 | 10.1 | 45 | 0 | 31 | 0.894 |
| 256 | 19 | 9.1 | 3.8 | 219 | 0.2 | 53 | 6.1 | 32 | 0.871 |
| 258 | 30 | 9.3 | 3.4 | 60 | 0.6 | 68 | 0 | 33 | 0.829 |
| 259 | 21 | 9.2 | 4.4 | 44 | 0.2 | 108 | 0 | 54 | 0.805 |
| 260 | 23 | 9.1 | 3.8 | -1 | 0.3 | 62 | 0 | 61 | 0.818 |
| 261 | 23 | 9.4 | 3.4 | -1 | 0.2 | 85 | 0 | 32 | 0.795 |
| 265 | 24 | 9.4 | 3.2 | 191 | 0.2 | 71 | 0 | 30 | 0.829 |
| 266 | 26 | 9 | 3.9 | 91 | 0.3 | 51 | 5.5 | 47 | 0.869 |
| 268 | 20 | 9.3 | 4.3 | 62 | 0.2 | 61 | 0 | 60 | 0.857 |
| 269 | 19 | 8.9 | 3.9 | 53 | 0.8 | 68 | 0 | 42 | 0.837 |
| 271 | 20 | 8.9 | 4.1 | 277 | 18.9 | 65 | 0 | 40 | 0.869 |
| 272 | 24 | 9 | 3.3 | 58 | 0.4 | 66 | 0 | 49 | 0.815 |
| 274 | 19 | 9.7 | 3.8 | 44 | 0.3 | 120 | 0 | 70 | 0.776 |
| 276 | 25 | 9.2 | 3.9 | -1 | 0.9 | 65 | 5 | 27 | 0.837 |
| 279 | 21 | 10 | 4.6 | 115 | 0.5 | 106 | 0 | 70 | 0.834 |
| 280 | 21 | 9.5 | 4.1 | 202 | 0.9 | 68 | 0 | 57 | 0.856 |
| 281 | 20 | 9.1 | 3.6 | -1 | 0.3 | 47 | 0 | 53 | 0.831 |
| 284 | 27 | 9 | 3.3 | 376 | 0.6 | 43 | 0 | 37 | 0.855 |
| 285 | 31 | 9.6 | 3.7 | 208 | 1.2 | 60 | 0 | 62 | 0.842 |
| 286 | 27 | 9 | 3.2 | 350 | 1.5 | 65 | 0 | 60 | 0.819 |
| 287 | 22 | 9 | 3.1 | 45 | 0.2 | 66 | 0 | 39 | 0.805 |
| 290 | 23 | 9.3 | 4.3 | 57 | 0.3 | 104 | 0 | 47 | 0.817 |
| 292 | 24 | 9.4 | 3.7 | 35 | 0.3 | 62 | 0 | 43 | 0.829 |
| 296 | 21 | 9.2 | 3.2 | 65 | 0.3 | 111 | 0 | 55 | 0.767 |
| 298 | 26 | 9.4 | 3.2 | 248 | 0.8 | 57 | 0 | 35 | 0.842 |
| 321 | 39 | 8.9 | 3.6 | 84 | 0.2 | 66 | 0 | 42 | 0.785 |
| 326 | 22 | 9.4 | 3.6 | 45 | 0.4 | 50 | 0 | 37 | 0.847 |
| 331 | 48 | 9.7 | 3.1 | 47 | 0.3 | 84 | 0 | 58 | 0.677 |
| 332 | 51 | 9.8 | 3.5 | -1 | 0.3 | 64 | 0 | 40 | 0.707 |
| 333 | 53 | 9.2 | 3.3 | 166 | 1.2 | 63 | 0 | 56 | 0.705 |
| 340 | 42 | 9.1 | 2.8 | 52 | 0.2 | 67 | 0 | 64 | 0.728 |

FIG. 9A

| PATIENT | AGE | CAL | PHOS | ETWO | PROG | TALP | TINTES | PLIVER | SCORE |
|---|---|---|---|---|---|---|---|---|---|
| 342 | 50 | 9.6 | 3.8 | 76 | 0.3 | 62 | 0 | 71 | 0.730 |
| 346 | 44 | 9.2 | 3.4 | 111 | 4.9 | 72 | 12.4 | 50 | 0.977 |
| 347 | 41 | 9.5 | 3.7 | -1 | 0.2 | 77 | 0 | 69 | 0.735 |
| 359 | 54 | 9.3 | 3.6 | 95 | 0.2 | 77 | 0 | 69 | 0.693 |
| 360 | 34 | 9.4 | 3.6 | 62 | 0.4 | 76 | 0 | 63 | 0.791 |
| 364 | 40 | 10 | 4.2 | 104 | 0.3 | 62 | 9 | 57 | 0.811 |
| 365 | 46 | 9 | 3.5 | 97 | 6.7 | 54 | 0 | 64 | 0.698 |
| 375 | 53 | 9.3 | 3.9 | 75 | 0.2 | 62 | 0 | 66 | 0.718 |
| 382 | 48 | 8.7 | 4.8 | 36 | 0.2 | 63 | 0 | 66 | 0.796 |
| 386 | 24 | 9.3 | 3.8 | -1 | 0.3 | 68 | 0 | 65 | 0.812 |
| 389 | 22 | 9.1 | 4.3 | -1 | 0.3 | 66 | 0 | 65 | 0.831 |
| 391 | 32 | 9.7 | 3.3 | -1 | 0.4 | 57 | 0 | 64 | 0.797 |
| 393 | 29 | 9.6 | 3.5 | 30 | 0.5 | 47 | 0 | 61 | 0.828 |
| 394 | 27 | 8.9 | 4.1 | -1 | 0.4 | 45 | 0 | 56 | 0.848 |
| 402 | 38 | 8.7 | 3.5 | 33 | 0.6 | 43 | 0 | 46 | 0.786 |
| 403 | 32 | 9.2 | 3.4 | -1 | 0.3 | 21 | 0 | 24 | 0.842 |
| 404 | 49 | 9.2 | 4.5 | -1 | 0.1 | 100 | 0 | 53 | 0.736 |
| 407 | 52 | 9.4 | 3.3 | 152 | 0.4 | 71 | 0 | 52 | 0.704 |
| 408 | 24 | 9 | 3.7 | 132 | 0.6 | 87 | 0 | 49 | 0.819 |
| 409 | 46 | 9.2 | 4.1 | 69 | 7.1 | 52 | 0 | 58 | 0.698 |
| 412 | 52 | 9.7 | 3.6 | -1 | 0.2 | 68 | 0 | 29 | 0.704 |
| 416 | 44 | 9.7 | 3.4 | 142 | 0.7 | 80 | 0 | 79 | 0.692 |
| 417 | 49 | 9.5 | 3.4 | -1 | 0.2 | 75 | 0 | 47 | 0.708 |
| 418 | 49 | 10 | 4.2 | 403 | 1.3 | 88 | 0 | 75 | 0.678 |
| 419 | 26 | 9.3 | 3 | -1 | 0.4 | 82 | 0 | 65 | 0.767 |
| 422 | 38 | 9.2 | 3.3 | 198 | 0.2 | 76 | 0 | 24 | 0.780 |
| 539 | 46 | 9.3 | 4.5 | 793 | 0.7 | 46 | 0 | 33 | 0.813 |
| 545 | 26 | 9.7 | 3 | 96 | 0.3 | 65 | 0 | 42 | 0.825 |
| 549 | 26 | 9.5 | 3.9 | 50 | 0.4 | 46 | 7.2 | 49 | 0.862 |
| 560 | 33 | 8.9 | 3.4 | 118 | 0.3 | 79 | 7.4 | 61 | 0.791 |
| 562 | 23 | 9.4 | 3.2 | -1 | 0.4 | 58 | 0 | 36 | 0.815 |
| 579 | 20 | 9 | 3.4 | 48 | 0.5 | 80 | 0 | 53 | 0.797 |
| 588 | 36 | 9.3 | 3.5 | -1 | 0.1 | 48 | 0 | 51 | 0.793 |
| 591 | 28 | 9.7 | 3.7 | 36 | 0.5 | 52 | 0 | 54 | 0.838 |
| 593 | 35 | 9 | 3.7 | 108 | 0.3 | 69 | 9.6 | 41 | 0.811 |
| 597 | 32 | 9.3 | 3.5 | -1 | 0.3 | 53 | 0 | 71 | 0.801 |
| 602 | 49 | 9.3 | 3.6 | 180 | 4.3 | 69 | 0 | 46 | 0.693 |
| 2520 | 29 | 9.2 | 4.4 | 52 | 0.2 | 49 | 0 | 41 | 0.877 |
| 3000 | 28 | 9.4 | 3.7 | 49 | 0.4 | 66 | 0 | 53 | 0.828 |
| 3020 | 25 | 9.6 | 4 | 164 | 16.8 | 56 | 0 | 41 | 0.880 |
| 100 | 52 | 8.7 | 3.1 | 371 | 0.3 | 59 | 0 | 54 | 0.703 |
| 113 | 53 | 9.8 | 3.5 | 3 | 0.2 | 63 | 0 | 67 | 0.690 |
| 126 | 42 | 9 | 4 | 99 | 16.4 | 83 | 14.4 | 36 | 0.984 |
| 130 | 50 | 9.3 | 3.5 | 336 | 0.6 | 40 | 0 | 25 | 0.754 |
| 139 | 74 | 8.9 | 3.7 | 209 | 0.4 | 35 | 5.9 | 36 | 0.648 |
| 160 | 60 | 9.5 | 3.9 | 81 | 0.3 | 47 | 5.2 | 53 | 0.704 |
| 176 | 56 | 9 | 2.9 | 115 | 0.2 | 64 | 0 | 58 | 0.677 |

FIG. 9B

| PATIENT | AGE | CAL | PHOS | ETWO | PROG | TALP | TINTES | PLIVER | SCORE |
|---|---|---|---|---|---|---|---|---|---|
| 177 | 39 | 9.4 | 3.1 | 71 | 0.2 | 82 | 0 | 45 | 0.751 |
| 208 | 42 | 9.1 | 2.4 | 177 | 15.6 | 54 | 0 | 70 | 0.757 |
| 211 | 50 | 9.5 | 3.1 | 69 | 0.2 | 77 | 0 | 60 | 0.696 |
| 214 | 25 | 9.2 | 3.7 | -1 | 0.9 | 43 | 0 | 29 | 0.852 |
| 251 | 24 | 9.5 | 3.9 | -1 | 0.1 | 61 | 0 | 25 | 0.844 |
| 273 | 30 | 9.4 | 3 | 99 | 0.2 | 156 | 8.3 | 26 | 0.776 |
| 299 | 27 | 9.2 | 3.2 | 41 | 0.2 | 77 | 0 | 58 | 0.788 |
| 309 | 35 | 9 | 3.9 | 55 | 0.3 | 90 | 8.7 | 62 | 0.773 |
| 316 | 41 | 9.4 | 3.5 | 75 | 7.3 | 44 | 0 | 27 | 0.733 |
| 320 | 52 | 9.3 | 3.4 | 57 | 0.2 | 58 | 0 | 55 | 0.707 |
| 355 | 54 | 9.1 | 3.6 | 93 | 0.4 | 55 | 0 | 40 | 0.718 |
| 358 | 54 | 9.5 | 3.6 | 38 | 0.3 | 71 | 0 | 54 | 0.688 |
| 361 | 49 | 9 | 3.8 | 31 | 0.3 | 74 | 9.5 | 50 | 0.744 |
| 371 | 49 | 9.5 | 3.8 | -1 | 0.2 | 72 | 10.3 | 42 | 0.698 |
| 377 | 52 | 9.6 | 3.6 | 120 | 0.2 | 68 | 0 | 53 | 0.717 |
| 385 | 55 | 9 | 3.3 | -1 | 0.2 | 97 | 0 | 73 | 0.646 |
| 398 | 53 | 9.3 | 4.6 | 30 | 0.2 | 97 | 10.3 | 28 | 0.697 |
| 406 | 26 | 9.6 | 3.4 | 35 | 0.3 | 62 | 0 | 70 | 0.806 |
| 414 | 52 | 9.3 | 3.9 | 56 | 0.4 | 66 | 0 | 72 | 0.710 |
| 421 | 31 | 9 | 3.5 | 72 | 0.3 | 69 | 0 | 52 | 0.818 |
| 536 | 48 | 9.4 | 3.4 | 54 | 3.2 | 56 | 0 | 63 | 0.688 |
| 544 | 38 | 9.3 | 2.4 | 126 | 0.2 | 64 | 0 | 59 | 0.747 |
| 566 | 36 | 9.3 | 4 | -1 | 0.5 | 41 | 0 | 44 | 0.822 |
| 603 | 27 | 8.9 | 4.4 | 42 | 0.3 | 48 | 0 | 38 | 0.872 |
| 109 | 54 | 9.4 | 3.3 | 64 | 0.3 | 121 | 9.6 | 65 | 0.652 |
| 110 | 58 | 9.4 | 3.9 | 20 | 0.1 | 85 | 0 | 58 | 0.663 |
| 129 | 45 | 8.8 | 3.7 | 197 | 10.8 | 56 | 0 | 53 | 0.733 |
| 141 | 46 | 9.7 | 3.6 | 141 | 2.1 | 68 | 0 | 44 | 0.709 |
| 158 | 45 | 8.9 | 3.3 | 243 | 0.8 | 63 | 0 | 43 | 0.763 |
| 164 | 51 | 9.3 | 3.5 | 139 | 0.5 | 59 | 0 | 43 | 0.727 |
| 170 | 51 | 9.4 | 3.3 | 120 | 4.2 | 50 | 0 | 30 | 0.737 |
| 178 | 36 | 9.7 | 3.3 | 139 | 0.4 | 40 | 0 | 46 | 0.824 |
| 180 | 38 | 8.7 | 3.4 | 48 | 0.4 | 52 | 0 | 39 | 0.783 |
| 181 | 34 | 8.7 | 3.4 | 78 | 11.1 | 67 | 6.8 | 33 | 0.817 |
| 183 | 44 | 9 | 3.6 | 131 | 0.2 | 35 | 0 | 54 | 0.807 |
| 191 | 45 | 9.3 | 3.5 | -1 | 0.4 | 45 | 0 | 58 | 0.760 |
| 194 | 29 | 9.2 | 3.7 | 89 | 0.1 | 82 | 0 | 52 | 0.824 |
| 200 | 45 | 9.2 | 3.7 | 226 | 1.6 | 46 | 0 | 27 | 0.786 |
| 204 | 25 | 9.5 | 3.5 | 170 | 0.3 | 43 | 0 | 46 | 0.863 |
| 209 | 42 | 9.6 | 2.9 | 539 | 0.4 | 50 | 0 | 64 | 0.738 |
| 216 | 46 | 9.2 | 3.6 | 156 | 0.5 | 43 | 0 | 39 | 0.780 |
| 218 | 43 | 9.5 | 4.4 | 133 | 0.7 | 59 | 0 | 41 | 0.791 |
| 225 | 37 | 9 | 2.7 | 159 | 1.4 | 64 | 6.7 | 48 | 0.766 |
| 226 | 72 | 9.9 | 4.9 | 46 | 0.3 | 77 | 8.9 | 61 | 0.643 |
| 227 | 46 | 9.6 | 4.4 | -1 | 0.2 | 94 | 0 | 38 | 0.757 |
| 230 | 43 | 9.3 | 3.4 | 94 | 0 | 71 | 0 | 77 | 0.721 |
| 231 | 35 | 8.9 | 3.2 | -1 | 0.3 | 51 | 0 | 61 | 0.777 |

FIG. 9C

| PATIENT | AGE | CAL | PHOS | ETWO | PROG | TALP | TINTES | PLIVER | SCORE |
|---|---|---|---|---|---|---|---|---|---|
| 233 | 50 | 9.1 | 3.5 | 43 | 0.3 | 73 | 0 | 23 | 0.709 |
| 238 | 46 | 8.3 | 3.4 | 234 | 0.2 | 55 | 5.9 | 46 | 1.094 |
| 239 | 40 | 9.5 | 3.6 | 43 | 1.6 | 71 | 0 | 63 | 0.758 |
| 246 | 34 | 9.8 | 3.3 | -1 | 0.3 | 42 | 0 | 58 | 0.804 |
| 248 | 51 | 8.9 | 3.8 | 76 | 0.2 | 61 | 0 | 62 | 0.724 |
| 255 | 19 | 9.6 | 4.3 | 49 | 0.3 | 86 | 0 | 34 | 0.841 |
| 257 | 23 | 8.9 | 2.9 | 118 | 2.7 | 75 | 0 | 21 | 0.816 |
| 262 | 26 | 9.1 | 3.6 | -1 | 0.2 | 47 | 0 | 24 | 0.844 |
| 267 | 23 | 9 | 3.8 | 170 | 0.4 | 84 | 0 | 50 | 0.825 |
| 270 | 21 | 9.1 | 3.9 | 47 | 0.9 | 40 | 0 | 70 | 0.850 |
| 277 | 27 | 9.4 | 4.6 | 58 | 0.2 | 138 | 0 | 69 | 0.811 |
| 278 | 29 | 9.4 | 3.9 | 404 | 1.2 | 62 | 7.9 | 46 | 0.864 |
| 282 | 28 | 9.4 | 3.9 | 60 | 0.2 | 57 | 0 | 36 | 0.859 |
| 283 | 25 | 10 | 3.6 | -1 | 0.3 | 48 | 0 | 32 | 0.847 |
| 288 | 24 | 9.7 | 4.1 | 65 | 0.3 | 107 | 7.2 | 35 | 0.816 |
| 289 | 27 | 9.4 | 3.4 | 68 | 0.6 | 87 | 0 | 37 | 0.812 |
| 291 | 26 | 9.6 | 3.3 | -1 | 0.3 | 58 | 0 | 28 | 0.823 |
| 293 | 26 | 9.6 | 4 | 32 | 0.2 | 68 | 0 | 35 | 0.838 |
| 295 | 26 | 9.1 | 3.3 | 57 | 0.5 | 51 | 0 | 63 | 0.324 |
| 310 | 47 | 9.5 | 3.6 | 306 | 1.5 | 53 | 0 | 46 | 0.730 |
| 314 | 48 | 9.1 | 2.7 | -1 | 0.2 | 64 | 0 | 53 | 0.704 |
| 328 | 37 | 9.4 | 3.2 | 54 | 0.4 | 74 | 0 | 55 | 0.762 |
| 335 | 47 | 9.2 | 4.2 | 49 | 0.4 | 74 | 0 | 56 | 0.745 |
| 341 | 37 | 9.3 | 3.3 | -1 | 0.1 | 68 | 0 | 56 | 0.758 |
| 349 | 50 | 8.8 | 3.1 | 151 | 0.1 | 67 | 8 | 30 | 0.710 |
| 353 | 50 | 9 | 4.1 | 374 | 0.2 | 53 | 0 | 30 | 0.759 |
| 354 | 58 | 9.7 | 4.3 | 74 | 0.3 | 48 | 6.8 | 45 | 0.726 |
| 363 | 50 | 9.1 | 3.3 | 76 | 0.6 | 93 | 13.8 | 31 | 0.694 |
| 366 | 24 | 9.4 | 2.7 | -1 | 0.5 | 50 | 0 | 31 | 0.806 |
| 372 | 21 | 10 | 2.9 | 56 | 0.7 | 79 | 0 | 61 | 0.789 |
| 378 | 42 | 9.2 | 3.5 | 169 | 0.1 | 72 | 0 | 56 | 0.754 |
| 381 | 62 | 9.5 | 3.6 | 56 | 0.1 | 63 | 0 | 30 | 0.672 |
| 384 | 62 | 9.4 | 4 | 34 | 0.2 | 98 | 25.3 | 33 | 0.644 |
| 387 | 52 | 9.6 | 3.7 | 38 | 0.2 | 133 | 0 | 55 | 0.669 |
| 388 | 64 | 9.1 | 3.1 | 87 | 0.3 | 80 | 0 | 75 | 0.636 |
| 396 | 57 | 8.8 | 3.1 | 76 | 0.2 | 83 | 7.7 | 51 | 0.659 |
| 397 | 58 | 9.6 | 3.3 | 73 | 0.3 | 85 | 0 | 52 | 0.665 |
| 400 | 50 | 9.1 | 3.5 | -1 | 0.2 | 99 | 9.7 | 50 | 0.671 |
| 410 | 37 | 9.5 | 2.8 | -1 | 0.3 | 44 | 0 | 48 | 0.769 |
| 411 | 49 | 9.4 | 3.1 | 138 | 7.5 | 69 | 0 | 27 | 0.674 |
| 415 | 31 | 9.6 | 4.6 | -1 | 0.4 | 42 | 0 | 72 | 0.861 |
| 424 | 54 | 9.4 | 3.1 | 59 | 0.4 | 101 | 0 | 35 | 0.662 |
| 507 | 45 | 9 | 3.4 | 46 | 0.3 | 55 | 0 | 65 | 0.745 |
| 513 | 25 | 9.4 | 3.5 | 52 | 0.2 | 72 | 0 | 52 | 0.815 |
| 533 | 61 | 9.6 | 3.9 | -1 | 0.1 | 80 | 0 | 61 | 0.655 |
| 535 | 24 | 9 | 3.3 | -1 | 0.3 | 68 | 0 | 55 | 0.795 |
| 537 | 48 | 9.9 | 3.2 | 32 | 0.3 | 81 | 0 | 58 | 0.679 |

FIG. 9D

| PATIENT | AGE | CAL | PHOS | ETWO | PROG | TALP | TINTES | PLIVER | SCORE |
|---|---|---|---|---|---|---|---|---|---|
| 540 | 45 | 9.5 | 2.9 | 391 | 0.7 | 49 | 7 | 35 | 0.955 |
| 541 | 54 | 9.3 | 4.4 | -1 | 0.2 | 68 | 0 | 37 | 0.714 |
| 542 | 32 | 9.2 | 3.4 | 80 | 0.6 | 51 | 0 | 60 | 0.829 |
| 546 | 62 | 9.3 | 4.5 | 100 | 0.1 | 45 | 0 | 59 | 0.711 |
| 548 | 52 | 9.2 | 4.1 | -1 | 0.4 | 55 | 0 | 59 | 0.719 |
| 550 | 48 | 9.9 | 3.7 | 92 | 0.3 | 127 | 0 | 78 | 0.668 |
| 554 | 36 | 9.1 | 3.5 | 42 | 0.4 | 44 | 0 | 37 | 0.808 |
| 561 | 30 | 8.9 | 3 | 54 | 0.2 | 55 | 0 | 54 | 0.809 |
| 568 | 53 | 9.6 | 3.2 | -1 | 0.3 | 49 | 0 | 40 | 0.699 |
| 569 | 26 | 9.2 | 4.5 | 274 | 0.5 | 80 | 9 | 30 | 0.870 |
| 571 | 45 | 9.1 | 3.3 | 402 | 1 | 72 | 0 | 54 | 0.731 |
| 572 | 58 | 9.5 | 3.9 | 52 | 0.2 | 57 | 7.3 | 23 | 0.700 |
| 576 | 65 | 9.5 | 3.3 | 43 | 0.2 | 78 | 0 | 56 | 0.632 |
| 580 | 50 | 9.3 | 3.2 | 60 | 0.2 | 76 | 8 | 43 | 0.696 |
| 582 | 44 | 8.9 | 3 | 119 | 0.2 | 80 | 7.1 | 24 | 0.967 |
| 583 | 45 | 8.9 | 3.2 | 353 | 0.2 | 68 | 0 | 64 | 0.744 |
| 586 | 41 | 8.8 | 3.7 | 223 | 0.7 | 73 | 12.4 | 22 | 1.206 |
| 589 | 52 | 9.3 | 3.5 | -1 | 0.3 | 88 | 0 | 45 | 0.678 |
| 592 | 55 | 9.2 | 3.7 | 95 | 0.3 | 50 | 0 | 57 | 0.717 |
| 595 | 46 | 9.1 | 3 | 128 | 4.5 | 90 | 8.2 | 35 | 1.000 |
| 596 | 46 | 9.5 | 3.6 | -1 | 0.2 | 53 | 0 | 47 | 0.757 |
| 604 | 56 | 9.3 | 4.3 | -1 | 0.2 | 84 | 0 | 53 | 0.684 |
| 605 | 47 | 8.9 | 3.4 | -1 | 1.4 | 64 | 0 | 40 | 0.740 |
| 608 | 46 | 9.7 | 3.8 | -1 | 0.1 | 69 | 0 | 48 | 0.742 |
| 2500 | 30 | 9.2 | 3.6 | 70 | 0.2 | 62 | 10.1 | 42 | 0.842 |
| 3010 | 24 | 9.4 | 3.8 | 178 | 15.9 | 33 | 0 | 34 | 0.894 |
| 106 | 52 | 9.1 | 3.4 | 44 | 0.2 | 86 | 9 | 55 | 0.674 |
| 117 | 61 | 9.5 | 3.2 | -1 | 0.1 | 85 | 0 | 60 | 0.634 |
| 121 | 46 | 9.5 | 2.9 | 48 | 0.3 | 80 | 0 | 54 | 0.690 |
| 133 | 47 | 9 | 4.2 | 203 | 15 | 57 | 7 | 52 | 0.939 |
| 151 | 36 | 9.1 | 3.8 | -1 | 0.3 | 80 | 0 | 57 | 0.768 |
| 156 | 34 | 9.6 | 3.9 | 114 | 17.9 | 41 | 0 | 37 | 0.866 |
| 166 | 51 | 9.2 | 3.8 | 60 | 0.1 | 60 | 0 | 42 | 0.727 |
| 167 | 49 | 8.5 | 3.8 | 76 | 0.5 | 97 | 10 | 48 | 0.810 |
| 179 | 32 | 9.5 | 3.6 | 59 | 0.2 | 61 | 0 | 47 | 0.826 |
| 182 | 51 | 8.4 | 3.7 | 99 | 0.2 | 84 | 0 | 31 | 0.709 |
| 189 | 53 | 9.2 | 4.2 | -1 | 0.1 | 68 | 8 | 47 | 0.705 |
| 212 | 37 | 9.4 | 3.7 | 162 | 18.6 | 55 | 0 | 57 | 0.818 |
| 217 | 67 | 9.4 | 3.2 | -1 | 0.2 | 64 | 6.3 | 33 | 0.628 |
| 219 | 50 | 9.6 | 3.7 | -1 | 0.3 | 81 | 0 | 18 | 0.707 |
| 222 | 56 | 9.1 | 3.9 | 30 | 0.2 | 102 | 0 | 61 | 0.657 |
| 228 | 51 | 9.4 | 3.5 | 141 | 0.4 | 61 | 0 | 28 | 0.730 |
| 235 | 41 | 9 | 4.3 | 96 | 0.3 | 45 | 0 | 39 | 0.868 |
| 252 | 52 | 9.5 | 3.3 | 34 | 0.2 | 79 | 0 | 48 | 0.681 |
| 264 | 28 | 9.1 | 3.4 | -1 | 0.2 | 50 | 0 | 60 | 0.816 |
| 275 | 25 | 9.1 | 2.5 | -1 | 0.4 | 38 | 0 | 34 | 0.806 |
| 297 | 23 | 9.4 | 4.4 | 177 | 12.2 | 72 | 0 | 55 | 0.873 |

FIG. 9E

| PATIENT | AGE | CAL | PHOS | ETWO | PROG | TALP | TINTES | PLIVER | SCORE |
|---|---|---|---|---|---|---|---|---|---|
| 317 | 47 | 9.6 | 2.4 | -1 | 0.2 | 60 | 0 | 27 | 0.709 |
| 324 | 46 | 9.4 | 4 | 117 | 0.4 | 75 | 0 | 54 | 0.732 |
| 327 | 46 | 9 | 3.4 | 322 | 1 | 46 | 0 | 52 | 0.765 |
| 329 | 49 | 9.5 | 3.7 | 72 | 2.4 | 78 | 0 | 45 | 0.692 |
| 337 | 46 | 9.3 | 3.5 | 122 | 10.3 | 48 | 0 | 42 | 0.700 |
| 352 | 56 | 8.8 | 3.6 | 73 | 0.2 | 53 | 0 | 35 | 0.707 |
| 357 | 35 | 9.4 | 2.9 | 89 | 2.3 | 71 | 7.6 | 23 | 0.791 |
| 367 | 42 | 9.1 | 3.2 | 58 | 0.5 | 90 | 9.8 | 64 | 0.846 |
| 369 | 62 | 9.6 | 3.6 | 31 | 0.2 | 86 | 0 | 39 | 0.645 |
| 379 | 42 | 8.6 | 3.4 | 156 | 6.3 | 84 | 0 | 61 | 0.742 |
| 380 | 49 | 9.6 | 4.2 | -1 | 0.2 | 71 | 11 | 52 | 0.690 |
| 383 | 62 | 9 | 3.5 | 81 | 0.1 | 66 | 7 | 52 | 0.665 |
| 392 | 63 | 9.5 | 3.4 | -1 | 0.3 | 98 | 0 | 76 | 0.620 |
| 517 | 25 | 10 | 4 | 31 | 0.1 | 50 | 0 | 50 | 0.853 |
| 526 | 47 | 9.1 | 3.8 | 94 | 0.2 | 62 | 0 | 51 | 0.750 |
| 543 | 59 | 9.4 | 4.2 | -1 | 0.2 | 104 | 0 | 20 | 0.662 |
| 553 | 48 | 8.8 | 4.1 | 35 | 0.5 | 57 | 0 | 66 | 0.759 |
| 556 | 69 | 9.6 | 4 | 77 | 0.1 | 44 | 6.8 | 53 | 0.668 |
| 567 | 29 | 9.4 | 4.2 | -1 | 0.3 | 67 | 9.7 | 33 | 0.841 |
| 575 | 45 | 9.1 | 3.1 | 406 | 0.6 | 104 | 0 | 54 | 0.704 |
| 584 | 57 | 9.2 | 3.2 | 141 | 0.2 | 79 | 0 | 40 | 0.674 |
| 599 | 49 | 8.9 | 4 | 42 | 0.2 | 79 | 9 | 51 | 0.748 |
| 2510 | 26 | 9.5 | 3.9 | 157 | 16.2 | 56 | 0 | 25 | 0.881 |
| 105 | 75 | 9.4 | 4.1 | 42 | 0.4 | 88 | 8 | 52 | 0.605 |
| 116 | 67 | 8.9 | 4 | -1 | 0.3 | 56 | 0 | 70 | 0.647 |
| 118 | 55 | 8.9 | 4.3 | 38 | 0.2 | 78 | 0 | 37 | 0.699 |
| 119 | 56 | 9.3 | 4.3 | 75 | 0.3 | 41 | 0 | 43 | 0.740 |
| 127 | 73 | 9 | 4.1 | 30 | 0.4 | 54 | 6.5 | 35 | 0.632 |
| 134 | 50 | 9.4 | 3.7 | 486 | 0.4 | 54 | 0 | 63 | 0.737 |
| 136 | 36 | 9.1 | 3.6 | 167 | 5.7 | 154 | 0 | 74 | 0.758 |
| 140 | 56 | 9 | 3.9 | -1 | 0.2 | 94 | 0 | 58 | 0.663 |
| 143 | 55 | 9.1 | 4 | -1 | 0.2 | 65 | 0 | 38 | 0.698 |
| 145 | 49 | 9.3 | 3.3 | 67 | 8.9 | 63 | 0 | 54 | 0.656 |
| 147 | 53 | 9.1 | 3.6 | 75 | 0.2 | 103 | 4.9 | 78 | 0.670 |
| 157 | 52 | 9.2 | 3.5 | 65 | 0.2 | 70 | 0 | 62 | 0.701 |
| 159 | 57 | 9.4 | 3 | -1 | 0.2 | 129 | 30.2 | 27 | 0.631 |
| 161 | 74 | 9.3 | 3.9 | -1 | 0.1 | 62 | 0 | 34 | 0.623 |
| 162 | 62 | 9 | 4.1 | 81 | 0.1 | 54 | 7.2 | 21 | 0.698 |
| 163 | 46 | 9.2 | 2.9 | 128 | 5.7 | 62 | 0 | 35 | 0.704 |
| 165 | 57 | 9.2 | 2.9 | -1 | 0.2 | 108 | 0 | 39 | 0.629 |
| 169 | 59 | 9.5 | 3.9 | 61 | 0.1 | 64 | 0 | 34 | 0.693 |
| 174 | 40 | 9.5 | 3.2 | 261 | 4.6 | 85 | 0 | 22 | 0.764 |
| 175 | 39 | 9.1 | 2.3 | 126 | 3.5 | 90 | 0 | 36 | 0.726 |
| 185 | 78 | 8.7 | 2.9 | -1 | 0.1 | 99 | 8.5 | 35 | 0.563 |
| 186 | 73 | 9.2 | 2.9 | 62 | 0.2 | 55 | 0 | 42 | 0.616 |
| 187 | 59 | 9 | 3.8 | 55 | 1.8 | 70 | 0 | 37 | 0.682 |
| 190 | 41 | 8.7 | 3 | 110 | 11.6 | 60 | 0 | 26 | 0.772 |

FIG. 9F

| PATIENT | AGE | CAL | PHOS | ETWO | PROG | TALP | TINTES | PLIVER | SCORE |
|---|---|---|---|---|---|---|---|---|---|
| 192 | 42 | 9.5 | 4.1 | 46 | 0.4 | 58 | 0 | 66 | 0.767 |
| 195 | 58 | 9 | 3.4 | 236 | 0.1 | 61 | 0 | 40 | 0.688 |
| 202 | 67 | 9.4 | 3.2 | 66 | 0.3 | 59 | 0 | 61 | 0.641 |
| 210 | 60 | 9.6 | 3.2 | 82 | 0.1 | 49 | 4.7 | 56 | 0.681 |
| 215 | 45 | 9.2 | 3.8 | 135 | 1.8 | 70 | 0 | 56 | 0.729 |
| 221 | 52 | 9.5 | 4 | 83 | 0.8 | 60 | 0 | 57 | 0.735 |
| 224 | 53 | 8.7 | 3.6 | 110 | 0.2 | 52 | 0 | 27 | 0.726 |
| 229 | 51 | 9.5 | 4.1 | 33 | 0.3 | 97 | 0 | 51 | 0.693 |
| 237 | 59 | 9.4 | 4 | -1 | 0.2 | 90 | 9.9 | 34 | 0.660 |
| 241 | 48 | 9.6 | 3.9 | 44 | 0.5 | 68 | 0 | 31 | 0.747 |
| 263 | 23 | 9.6 | 4.2 | 39 | 0.5 | 69 | 0 | 28 | 0.853 |
| 294 | 25 | 9.3 | 3.8 | 91 | 2.9 | 64 | 0 | 54 | 0.853 |
| 308 | 54 | 8.8 | 3.1 | -1 | 0.2 | 40 | 0 | 48 | 0.692 |
| 313 | 53 | 9.8 | 4.3 | -1 | 0.4 | 90 | 0 | 40 | 0.700 |
| 319 | 31 | 9 | 3.5 | 296 | 2.8 | 49 | 0 | 27 | 0.859 |
| 322 | 42 | 9.4 | 3.3 | -1 | 0.3 | 63 | 6.6 | 41 | 0.757 |
| 323 | 56 | 8.8 | 3.6 | 38 | 0.1 | 54 | 6.5 | 54 | 0.685 |
| 334 | 68 | 8.8 | 4.1 | 83 | 0.4 | 44 | 0 | 39 | 0.676 |
| 338 | 42 | 9.9 | 3.2 | 35 | 1 | 92 | 9.4 | 41 | 0.719 |
| 339 | 52 | 9.9 | 3.7 | 84 | 0.2 | 78 | 0 | 62 | 0.711 |
| 343 | 44 | 9.1 | 3.4 | 55 | 1.3 | 75 | 8 | 55 | 0.834 |
| 344 | 61 | 9.2 | 4.3 | 82 | 0.3 | 116 | 8.3 | 65 | 0.655 |
| 351 | 46 | 9.2 | 3.9 | 140 | 0.3 | 58 | 8 | 51 | 0.905 |
| 362 | 53 | 9.6 | 3.9 | 94 | 0.1 | 83 | 0 | 72 | 0.703 |
| 373 | 62 | 9.9 | 3.4 | 172 | 0.2 | 83 | 0 | 66 | 0.654 |
| 376 | 70 | 9.9 | 4.7 | -1 | 0.1 | 109 | 0 | 38 | 0.627 |
| 390 | 72 | 9 | 3.8 | -1 | 0.2 | 108 | 14.5 | 28 | 0.597 |
| 395 | 54 | 9.2 | 4.1 | -1 | 0.3 | 96 | 0 | 67 | 0.674 |
| 399 | 49 | 9.4 | 3 | -1 | 0.4 | 64 | 0 | 50 | 0.701 |
| 401 | 83 | 8.7 | 3.8 | 31 | 0.2 | 111 | 0 | 55 | 0.558 |
| 413 | 46 | 9.4 | 3.6 | 90 | 0.1 | 98 | 25.1 | 54 | 0.746 |
| 423 | 44 | 9.2 | 3.6 | 62 | 0.2 | 47 | 0 | 45 | 0.785 |
| 527 | 38 | 9.3 | 3.3 | 40 | 0.4 | 62 | 4.1 | 56 | 0.763 |
| 552 | 54 | 9.4 | 3.7 | -1 | 0.2 | 80 | 0 | 57 | 0.679 |
| 555 | 50 | 9.5 | 3 | 108 | 0.2 | 126 | 7.4 | 50 | 0.670 |
| 557 | 59 | 9.4 | 3.5 | 192 | 0.2 | 42 | 0 | 66 | 0.697 |
| 563 | 44 | 9.5 | 3.8 | 37 | 0.5 | 46 | 0 | 39 | 0.790 |
| 565 | 70 | 9 | 3.2 | -1 | 0.2 | 54 | 0 | 45 | 0.623 |
| 570 | 24 | 9.2 | 3.5 | 50 | 0.5 | 53 | 7 | 32 | 0.842 |
| 573 | 65 | 9.9 | 4.2 | -1 | 0.3 | 59 | 0 | 56 | 0.665 |
| 574 | 65 | 9.2 | 3.2 | 122 | 0.3 | 64 | 0 | 58 | 0.649 |
| 577 | 46 | 9.5 | 4.1 | 397 | .04 | 56 | 0 | 70 | 0.738 |
| 585 | 62 | 9 | 3.5 | 56 | 0.2 | 77 | 0 | 21 | 0.658 |
| 590 | 65 | 9.2 | 3.7 | -1 | 0.2 | 72 | 0 | 57 | 0.640 |
| 594 | 55 | 9.9 | 3.6 | -1 | 0.2 | 43 | 0 | 52 | 0.705 |
| 601 | 45 | 8.9 | 3.1 | 81 | 3.4 | 75 | 6.6 | 54 | 0.858 |
| 607 | 81 | 9.7 | 3.5 | -1 | 0.1 | 66 | 0 | 31 | 0.590 |

FIG. 9G

| PATIENT | AGE | CAL | PHOS | ETWO | PROG | TALP | TINTES | PLIVER | SCORE |
|---|---|---|---|---|---|---|---|---|---|
| 111 | 69 | 9 | 3.3 | 34 | 0.4 | 68 | 9.3 | 55 | 0.615 |
| 124 | 51 | 9.2 | 3.7 | 35 | 0.2 | 69 | 0 | 48 | 0.704 |
| 149 | 52 | 9.2 | 3.9 | -1 | 0.3 | 82 | 0 | 72 | 0.686 |
| 152 | 56 | 9 | 2.5 | 79 | 0.2 | 77 | 0 | 43 | 0.659 |
| 168 | 56 | 9.1 | 4.1 | -1 | 0.1 | 76 | 0 | 45 | 0.686 |
| 196 | 61 | 9.3 | 3.3 | 69 | 0.1 | 97 | 8.8 | 36 | 0.642 |
| 330 | 63 | 8.9 | 3.8 | -1 | 0.1 | 68 | 9.6 | 54 | 0.648 |
| 345 | 65 | 8.9 | 4.2 | 40 | 0.1 | 50 | 5.3 | 19 | 0.676 |
| 356 | 53 | 9.7 | 3.5 | 54 | 0.2 | 99 | 0 | 60 | 0.673 |
| 534 | 66 | 8.9 | 3.5 | 78 | 0.1 | 61 | 0 | 53 | 0.654 |
| 551 | 67 | 9.3 | 3.5 | 47 | 0.2 | 66 | 10 | 47 | 0.635 |
| 558 | 38 | 9.3 | 3.3 | 137 | 7.9 | 85 | 0 | 66 | 0.765 |
| 578 | 51 | 8.8 | 3.9 | 34 | 0.3 | 50 | 0 | 54 | 0.722 |
| 581 | 53 | 9.3 | 3.4 | 62 | 0.2 | 56 | 0 | 54 | 0.707 |
| 104 | 63 | 9.3 | 4.3 | 77 | 0.3 | 88 | 7.6 | 41 | 0.669 |
| 120 | 66 | 9.3 | 3.8 | 35 | 0.2 | 81 | 0 | 61 | 0.633 |
| 125 | 63 | 9.3 | 4 | -1 | 0.4 | 92 | 0 | 55 | 0.642 |
| 138 | 60 | 9.3 | 2.8 | 58 | 0.3 | 84 | 0 | 77 | 0.634 |
| 144 | 68 | 9.5 | 4.6 | -1 | 0.4 | 118 | 0 | 30 | 0.632 |
| 146 | 67 | 9.8 | 3.3 | -1 | 0.2 | 74 | 0 | 59 | 0.623 |
| 150 | 44 | 9.6 | 3.8 | 65 | 0.2 | 122 | 0 | 44 | 0.716 |
| 193 | 50 | 10 | 3.2 | -1 | 0.3 | 67 | 0 | 24 | 0.705 |
| 198 | 36 | 9.4 | 3.2 | 262 | 0.6 | 101 | 14.1 | 18.3 | 0.761 |
| 207 | 57 | 9.7 | 3.5 | 33 | 0.3 | 74 | 0 | 57 | 0.668 |
| 232 | 65 | 9.4 | 4 | 80 | 0.2 | 69 | 0 | 53 | 0.668 |
| 236 | 48 | 9 | 3.6 | 73 | 8.9 | 43 | 0 | 33 | 0.704 |
| 240 | 53 | 9.1 | 4.1 | 41 | 0.2 | 56 | 5 | 39 | 0.721 |
| 242 | 57 | 9.4 | 3.8 | -1 | 0.1 | 71 | 9.8 | 34 | 0.677 |
| 315 | 64 | 9.7 | 3.5 | 46 | 0.2 | 83 | 11.4 | 37 | 0.639 |
| 318 | 49 | 9.8 | 3.2 | 168 | 3 | 46 | 0 | 34 | 0.701 |
| 325 | 57 | 9.2 | 4.3 | -1 | 0.1 | 124 | 0 | 43 | 0.662 |
| 336 | 55 | 9.2 | 3.6 | -1 | 0.3 | 76 | 10 | 28 | 0.676 |
| 348 | 58 | 8.7 | 3.5 | -1 | 0.2 | 55 | 0 | 55 | 0.672 |
| 368 | 62 | 9.4 | 3.9 | -1 | 0.2 | 68 | 0 | 45 | 0.663 |
| 370 | 77 | 9.5 | 4.1 | -1 | 0.4 | 98 | 10.2 | 21 | 0.596 |
| 374 | 76 | 9.9 | 3.7 | -1 | 0.3 | 78 | 0 | 54 | 0.600 |
| 528 | 80 | 9 | 3.9 | 6 | 0.2 | 103 | 0 | 71 | 0.571 |
| 529 | 66 | 9.1 | 3.5 | -1 | 0.1 | 67 | 0 | 54 | 0.634 |
| 538 | 79 | 9.4 | 3.9 | -1 | 0.3 | 96 | 9.4 | 39 | 0.582 |
| 547 | 73 | 9.3 | 3.6 | 126 | 0.1 | 64 | 0 | 22 | 0.636 |
| 559 | 68 | 9.7 | 3.6 | 91 | 0.1 | 37 | 0 | 57 | 0.669 |
| 564 | 80 | 9.5 | 3.6 | 33 | 0.2 | 113 | 10.7 | 52 | 0.565 |
| 598 | 69 | 9.6 | 4.4 | 128 | 0.7 | 72 | 2.5 | 57 | 0.660 |
| 600 | 64 | 9.2 | 4.5 | -1 | 0.4 | 66 | 0 | 47 | 0.671 |
| 606 | 78 | 9.5 | 3.9 | -1 | 0.1 | 77 | 0 | 58 | 0.596 |

FIG. 9H

| Radiological Diagnoses based on DEXA scans at Hip and Spine | QuiOs™ | | Row Total |
|---|---|---|---|
| | Having a Biochemical Indication of Clinically Significant Osteopenia (QuiOs™ ≤ 0.730) | Having No Biochemical Indication of Clinically Significant Osteopenia (QuiOs™ > 0.730) | |
| Advanced | 131 | 15 | 148 |
| Moderate | 161 | 97 | 258 |
| Mild | 68 | 180 | 248 |
| Normal | 7 | 67 | 74 |
| Column Total | 367 | 359 | 725 |

Sensitivity of detecting radiologically diagnosed Advanced Osteopenia as having a biochemical indication of clinically significant osteopenia:
Sensitivity = 90%

Sensitivity of detecting radiologically diagnosed Advanced or Moderate Osteopenia as having a biochemical indication of clinically significant osteopenia:
Sensitivity = 72%

Specificity of identifying Normal patients as having no biochemical indication of clinically significant osteopenia:
Specificity = 91%

Specificity of identifying Normal or Mild Osteopenia as having no biochemical indication of clinically significant osteopenia:
Specificity = 77%

Definition of DEXA based diagnoses of test subjects:

*Advanced - both DEXA scans at Lateral Spine L2-4 and Ward's Triangle have T scores ≤ -2.0;
  * Moderate - one of the DEXA scans at Lateral Spine L2-4 and Ward's Triangle has T-score ≤ 2.0, or both sites have T-scores > 2.0 and ≤ -1.0;
  Mild - one of the DEXA scans at Lateral Spine L2-4 and Ward's Triangle has T-score > -1.0 and the other has T-score ≥ -2.0, not including cases with both sites T-scores > 0.0;
  Normal - both DEXA scans at Lateral Spine L2-4 and Ward's Triangle have T-scores >0.0.

\* Clinically significant osteopenia may be confirmed by finding of low bone mass (for example, at least 2 standard deviation (SDs) below the premenopausal population mean peak).

FIG. 10

ProstAsure™ Age-Specific Reference Ranges

| Age Groups | Normal | BPH* | Cancer |
|---|---|---|---|
| 40 - 59 | ≤ 20.0 | (20.0, 32.0) | > 32.0 |
| 60 - 69 | ≤ 10.0 | (10.0, 35.0) | > 35.0 |
| ≥ 70 | ≤ 10.0 | (10.0, 37.0) | > 37.0 |

- a BPH patient with ProstAsure™ above the mid-point of his age-specific BPH reference range is labeled as Suspicious BPH and is strongly recommended for a biopsy for a definitive diagnosis.

FIG. 17

Diagnostic guidelines for the 416 samples in the test data set:

- *Presumed Normal:* PSA < 4.0 and negative DRE;
- *BPH:* Enlarged prostate by DRE (examined by Stanford Urology faculty members only);
- *Cancer:* Confirmed by biopsy and histologic report.

FIG. 18

ProstAsure Result of 416 Test Samples in a 3x3 Table

| Gold Standard | ProstAsure™ | | | |
|---|---|---|---|---|
| Diagnosis | Cancer | BPH | Normal | Row Totals |
| Cancer | 155 | 36 | 2 | 193 |
| BPH | 16 | 76 | 23 | 115 |
| Presumed Normal | 0 | 35 | 73 | 108 |
| Column Totals | 171 | 147 | 98 | 416 |

Pearson Chi-Square = 314/5556  df = 4  p = 0.0000

FIG. 19

ProstAsure Result of 193 Test Cancer Cases

| Confirmed Cancer Stages | ProstAsure™ | | | Row Totals |
|---|---|---|---|---|
| | Cancer | BPH | Normal | |
| Stage T1b | 10 | 16 | 2 | 28 |
| Stage T2 | 80 | 14 | 0 | 94 |
| Stage T3 | 29 | 5 | 0 | 34 |
| Stage TNxM$_1$ | 36 | 1 | 0 | 37 |
| Column Totals | 155 | 36 | 2 | 193 |

FIG. 20

Sensitivity and Specificity of ProstAsure

| | |
|---|---|
| Sensitivity for Detecting Prostate Cancer | 80.3% |
| Sensitivity for Detecting Stage T2 Prostate Cancer | 85.3% |
| Sensitivity for Detecting Stages T2, T3 and $TNxM_1$ Prostate Cancer | 87.9% |
| Sensitivity for Detecting BPH as BPH | 66.1% |
| Specificity for Identifying Non-Cancer as Non-Cancer | 92.8% |
| Specificity for Identifying Presumed Normal as Normal | 67.6% |

FIG. 24

MATHEMATICAL DESCRIPTION OF THE PROSTASURE™ ALGORITHM

Input variables: *age, PSA, PAP, CK-BB, CK-MB,* and *CK-MM.*

The Input Layer

Internal Input vector before truncation:

$$X = [age, PSA/PAP, \ln(PSA+1), \ln(PAP+1), CK\text{-}BB, CK\text{-}BB + CK\text{-}MB + CK\text{-}MM, x_7]^T,$$

where $$x_7 = 1.856 - 0.023 \cdot age - 0.573 \cdot \ln(PSA+1) + 0.0001 \cdot age^2 + 0.004 \cdot \ln(PSA+1) \cdot age - 0.005 \cdot \ln(PSA+1)^2$$

Truncation Threshold vectors:

$$T_{lower} = \begin{bmatrix} 20.0 & 0.0 & 0.336 & 0.0 & 0.2 & 0.0 & -0.4 \end{bmatrix}^T$$

$$T_{upper} = \begin{bmatrix} 80.0 & 18.0 & 2.565 & 1.253 & 2.0 & 300.0 & 1.2 \end{bmatrix}^T$$

FIG. 25A

Then,
for $i = 1, 2, \ldots, 7$, let $$y_i = \begin{cases} -1.0 & \text{if}(x_i \leq T_{\text{lower},i}) \\ 1.0 & \text{if}(x_i \geq T_{\text{upper},i}) \\ \dfrac{2(x_i - T_{\text{lower},i})}{(T_{\text{upper},i} - T_{\text{lower},i})} - 1.0 & \text{else} \end{cases},$$

and define $$y_0 = 1.0.$$

The augmented output of the first layer, $$Y = [y_0, y_1, \ldots, y_7]^T.$$

will be used by both ANN No. 1 and ANN No. 2 as input to their hidden layers and jump connections.

Calculation of Output of ANN No.1

There are two hidden layer slabs and one jump connection.

FIG. 25B

Output of the Gaussian Slab of hidden layer

The two weight matrices (one leads to the slab, the other away from the slab):

$$WGI = \begin{bmatrix} -0.30404 & 0.27788 & -0.12895 & -0.07592 & 0.02998 & 0.10233 & 0.25638 & -0.16338 \\ 0.02559 & 0.26265 & -0.24423 & -0.23780 & -0.05485 & 0.11606 & 0.09825 & 0.14387 \\ -0.16049 & 0.12797 & -0.26480 & -0.22189 & -0.09213 & 0.21939 & 0.13761 & 0.17154 \\ 0.19431 & -0.22778 & -0.09058 & -0.27022 & 0.13686 & 0.01684 & -0.15848 & 0.29588 \\ 0.09917 & 0.07160 & -0.31651 & -0.10221 & 0.09032 & -0.09873 & 0.18685 & 0.36407 \\ 0.03887 & 0.15684 & -0.25465 & -0.19699 & -0.33428 & 0.11620 & -0.45861 & 0.17490 \\ -0.11272 & 0.22494 & 0.35798 & 0.06121 & -0.37441 & 0.13152 & 0.05846 & -0.16484 \end{bmatrix},$$

and $$WGO = \begin{bmatrix} -0.03539 & -0.11231 & 0.19318 & -0.13088 & 0.00137 & -0.24651 & 0.50834 & -0.35074 \end{bmatrix}^T.$$

For $i = 1, \ldots, 7$, let $$s_i = \exp\left[-\left(\sum_{j=0}^{7} WGI_{i-1,j} y_j\right)^2\right]$$

and $$s_0 = 1.0.$$

The input from the Gaussian Slab to the output layer:

$$t = \sum_{j=0}^{7} WGO_j s_j.$$

FIG. 25C

Output of the Jump Connection from the Input Layer

Connection weight matrix:

$$WJO = \begin{bmatrix} -0.18985 & -0.59914 & -0.21779 & -0.39691 & 0.50123 & 0.09711 & 0.75722 & 0.59222 \end{bmatrix}^T.$$

The input from this jump connection:

$$u = \sum_{j=0}^{7} WJO_j y_j.$$

Output of the Gaussian Complement Slab of Hidden Layer

The two weight matrices (one leads to the slab, the other away from the slab):

$$WCI = \begin{bmatrix} 0.03996 & -0.16843 & -0.24602 & -0.18836 & -0.27160 & -0.25193 & -0.23948 & -0.02604 \\ -0.19282 & 0.25369 & -0.14086 & -0.25352 & 0.23105 & 0.45174 & -0.13803 & -0.16674 \\ 0.11162 & -0.11121 & 0.04799 & 0.20671 & -0.15937 & 0.12143 & 0.23656 & 0.00191 \\ -0.01729 & 0.14089 & 0.18369 & -0.00630 & 0.24071 & -0.20974 & -0.01953 & 0.11067 \\ -0.03022 & 0.07420 & 0.01791 & -0.23635 & 0.14175 & 0.24953 & -0.17246 & 0.13564 \\ 0.27442 & 0.02910 & 0.28822 & 0.11619 & -0.11845 & 0.18619 & 0.01008 & 0.14143 \\ 0.09244 & -0.16291 & 0.22994 & 0.15931 & 0.08302 & 0.09219 & 0.28190 & -0.06994 \end{bmatrix}$$

FIG. 25D and $$WCO = \begin{bmatrix} -0.12130 & -0.17390 & 0.36017 & -0.31029 & 0.02372 & 0.04508 & -0.02368 & -0.36532 \end{bmatrix}^T.$$

For $i = 1, \ldots, 7$, let $$p_i = 1.0 - \exp\left[-\left(\sum_{j=0}^{7} WCI_{i-1,j} y_j\right)^2\right]$$

and $$p_0 = 1.0.$$

The input from the Gaussian Complement Slab to the output layer:

$$q = \sum_{j=0}^{7} WCO_j p_j.$$

Output of the Output Layer of ANN No. 1

$$\text{ANN\_It} = [1/(1.0 + \exp\{-(t + u + q)\}) - 0.1]/0.8.$$

$$\text{ANN\_I}_{\text{output}} = \begin{cases} 1.0, & \text{ANN\_It} > 1.0; \\ \text{ANN\_It}, & 0.0 \leq \text{ANN\_It} \leq 1.0; \\ 0.0, & \text{ANN\_It} < 0.0. \end{cases}$$

FIG. 25E

Calculation of Output of ANN No.2

The calculations within ANN No. 2 are similar to that in ANN No. 1 except that the Weight Matrices have different entries:

$$WGI = \begin{bmatrix} -0.34718 & 0.27551 & -0.14134 & -0.04266 & 0.07152 & 0.07470 & 0.32115 & -0.20041 \\ -0.02642 & 0.21017 & -0.30465 & -0.26102 & 0.05455 & 0.23146 & 0.29731 & 0.19462 \\ -0.22531 & 0.16655 & -0.28497 & -0.35511 & -0.23839 & 0.21491 & 0.02840 & 0.24657 \\ 0.21253 & -0.22915 & -0.09318 & -0.34358 & 0.11309 & 0.01545 & -0.25071 & 0.34791 \\ 0.08815 & 0.25152 & -0.26887 & -0.10120 & -0.02611 & -0.14523 & -0.02234 & 0.35697 \\ -0.02748 & 0.13650 & -0.23501 & 0.01659 & -0.10635 & 0.27423 & -0.18645 & 0.08375 \\ -0.12284 & 0.01700 & 0.36293 & 0.07783 & -0.30955 & 0.16605 & 0.24447 & -0.09268 \end{bmatrix}$$

and $$WGO = \begin{bmatrix} 0.08647 & 0.06597 & 0.29840 & 0.24123 & -0.03399 & -0.24138 & 0.35469 & -0.25157 \end{bmatrix}^T.$$

$$WJO = \begin{bmatrix} -0.24938 & 0.13448 & -0.32493 & -0.41677 & 0.02293 & 0.09125 & 0.26847 & 0.32690 \end{bmatrix}^T.$$

FIG. 25F $$WCI = \begin{bmatrix} -0.01639 & -0.23630 & -0.20532 & -0.09187 & -0.21388 & -0.25468 & -0.18542 & -0.05661 \\ -0.17253 & 0.07024 & -0.15819 & -0.18879 & 0.27017 & 0.27356 & -0.19592 & -0.13958 \\ 0.13655 & -0.06663 & -0.03741 & 0.09749 & -0.21735 & 0.11302 & 0.18674 & 0.03812 \\ -0.01853 & 0.14126 & 0.18175 & -0.00455 & 0.24318 & -0.20837 & -0.01479 & 0.10914 \\ -0.01747 & 0.06989 & 0.00873 & -0.25874 & 0.11843 & 0.22243 & -0.20730 & 0.15072 \\ 0.27522 & 0.04568 & 0.29272 & 0.12095 & -0.11641 & 0.19068 & 0.00186 & 0.13191 \\ 0.15020 & -0.07862 & 0.15400 & 0.00660 & -0.04242 & 0.04744 & 0.13730 & -0.01896 \end{bmatrix},$$

and $$WCO = \begin{bmatrix} 0.00056 & -0.05491 & 0.14461 & -0.26470 & -0.02535 & 0.02504 & -0.07503 & -0.24079 \end{bmatrix}^T.$$

Calculation of ProstAsure™ Index $$\text{ProstAsure}^{\text{TM}} = 13.2 \cdot \ln[(1.0 + \exp(-5.0(\text{ANN\_I}_{output} - 0.5))) \cdot \\ (1.0 + \exp(-5.1(\text{ANN\_II}_{output} - 0.73)))]$$

FIG. 25G

MATHEMATICAL DESCRIPTION OF THE QUIOS™ ALGORITHM

The QuiOs™ software system uses four independent artificial neural network (ANN) classifiers to process information internally. The output of the four ANNs are combined to form a single value as the QuiOs™ quotient output.

Input variables: *age, CAL, PHOS, ETWO, PROG, TALP, PLIVER, BONE,* and *weight* and *height*, where weight is in pounds and height in inches.

The Input Layer

Internal Input vector before truncation:

$$X = [age, CAL, PHOS, ETWO, PROG, TALP, PLIVER, BONE, weight/height]^T$$

Truncation Threshold vectors:

$$T_{lower} = \begin{bmatrix} 15 & 8 & 2 & 30 & 0 & 30 & 20 & 10 & 1.5 \end{bmatrix}^T$$

FIG. 26A $$T_{upper} = \begin{bmatrix} 80 & 11 & 5 & 120 & 9 & 110 & 70 & 56 & 3.2 \end{bmatrix}^T$$

Then, for $i = 1, 2, \ldots, 9$, let $$y_i = \begin{cases} -1.0 & \text{if}(x_i \leq T_{lower,i}) \\ 1.0 & \text{if}(x_i \geq T_{upper,i}) \\ \frac{2(x_i - T_{lower,i})}{(T_{upper,i} - T_{lower,i})} - 1.0 & \text{else} \end{cases},$$

and define $$y_0 = 1.0.$$

The augmented output of the first layer, $$Y = [y_0, y_1, \ldots, y_9]^T.$$

will be used by ANN No. 1, ANN No. 2, ANN No. 3 and ANN No. 4 as input to their hidden layers and jump connections.

Calculation of Output of ANN No.1 (Def:A1)

There are two hidden layer slabs and one jump connection.

FIG. 26B

Output of the Gaussian Slab of hidden layer

The two weight matrices (one leads to the slab, the other away from the slab):

$$WGI = \begin{bmatrix} -0.303299 & 0.238712 & -0.242210 & -0.294612 & -0.038508 & 0.224696 & 0.227745 & -0.143262 & -0.286049 & -0.029747 \\ 0.058636 & 0.145796 & -0.087058 & -0.068623 & -0.089029 & 0.113563 & -0.180561 & -0.118657 & 0.241983 & -0.170411 \\ -0.190152 & -0.207428 & -0.210839 & 0.014653 & -0.258678 & 0.282687 & 0.159832 & 0.203580 & -0.138839 & 0.149946 \\ 0.188927 & 0.214520 & -0.201171 & 0.044623 & 0.064453 & 0.251277 & 0.207400 & -0.285991 & -0.135420 & -0.018804 \\ 0.039047 & 0.129192 & 0.292250 & 0.051242 & 0.159887 & 0.035729 & 0.288059 & -0.075372 & 0.047367 & -0.025483 \\ 0.008743 & -0.021639 & -0.043779 & 0.046788 & 0.158628 & -0.232591 & 0.284816 & -0.225876 & 0.101629 & 0.287513 \\ -0.061566 & -0.112765 & -0.237170 & -0.198856 & -0.004815 & -0.051817 & 0.080888 & 0.107194 & 0.218254 & 0.143057 \\ 0.238742 & -0.312350 & -0.296771 & 0.097780 & -0.116692 & -0.155416 & -0.063356 & -0.264909 & 0.139329 & -0.226328 \end{bmatrix}$$

and $$WGO = \begin{bmatrix} 0.044272 & -0.151565 & 0.101315 & 0.101873 & 0.025073 & -0.063053 & -0.206456 & -0.190877 & -0.104936 \end{bmatrix}^T.$$

For $i = 1, \ldots, 8$, let $$s_i = \exp\left[-\left(\sum_{j=0}^{9} WGI_{i-1,j} y_j\right)^2\right]$$

and $$s_0 = 1.0.$$

FIG. 26C

The input from the Gaussian Slab to the output layer:

$$t = \sum_{j=0}^{8} WGO_j s_j.$$

Output of the Jump Connection from the Input Layer

Connection weight matrix:

$$WJO = \begin{bmatrix} 0.166572 & -0.464945 & 0.272867 & 0.127949 & 0.079196 & -0.121782 & 0.011149 & 0.004464 & -0.326211 & 0.333510 \end{bmatrix}^T.$$

The input from this jump connection:

$$u = \sum_{j=0}^{9} WJO_j y_j.$$

FIG. 26D

Output of the Gaussian Complement Slab of Hidden Layer

The two weight matrices (one leads to the slab, the other away from the slab):

$$WCI = \begin{bmatrix} -0.018679 & -0.240149 & -0.191189 & 0.027975 & -0.288713 & -0.067025 & -0.132869 & 0.234963 & 0.067266 & 0.264184 \\ -0.161618 & 0.255512 & 0.183104 & 0.132861 & 0.035317 & -0.060979 & 0.149022 & -0.287206 & 0.096249 & -0.118589 \\ 0.299513 & 0.190381 & -0.013370 & 0.162412 & 0.045618 & -0.100126 & 0.068358 & 0.291491 & -0.145056 & -0.145118 \\ -0.253573 & -0.275834 & -0.207570 & 0.117841 & -0.011591 & 0.239972 & -0.198745 & 0.057308 & 0.177208 & -0.165069 \\ 0.221690 & 0.193433 & 0.006056 & -0.015392 & -0.222181 & -0.091285 & 0.155249 & -0.265039 & -0.232979 & 0.157569 \\ 0.109032 & 0.203858 & 0.133303 & -0.232763 & 0.285709 & -0.019682 & 0.179474 & 0.026983 & -0.268727 & 0.211670 \\ -0.130380 & 0.031979 & -0.053613 & -0.074793 & 0.265640 & -0.130268 & -0.054298 & -0.196747 & 0.155706 & 0.127107 \\ -0.105436 & -0.249205 & -0.124375 & 0.191354 & 0.054032 & 0.346534 & -0.005831 & 0.203441 & -0.111904 & 0.075936 \end{bmatrix}$$

and $$WCO = \begin{bmatrix} 0.133173 & -0.128342 & -0.178770 & -0.344473 & -0.302709 & 0.119805 & 0.247879 & -0.193383 & -0.304841 \end{bmatrix}^T.$$

For $i = 1, \ldots, 8$, let $$p_i = 1.0 - \exp\left[-\left(\sum_{j=0}^{9} WCI_{i-1,j} y_j\right)^2\right]$$

and $$p_0 = 1.0.$$

FIG. 26E

The input from the Gaussian Complement Slab to the output layer:

$$q = \sum_{j=0}^{8} WCO_j p_j.$$

Output of the Output Layer of ANN No. 1 (Def:A1)

$$ANN\_1t = [1/(1.0 + \exp\{-(t + u + q)\}) - 0.1] \cdot 0.6/0.8 + 0.7.$$

$$ANN\_1_{output} = \begin{cases} 1.3, & ANN\_1t > 1.3; \\ ANN\_1t, & 0.7 \leq ANN\_1t \leq 1.3; \\ 0.7, & ANN\_1t < 0.7. \end{cases}$$

Calculation of Output of ANN No.2 (Def:P6)

The calculations within ANN No. 2 are similar to that in ANN No. 1 except that there are three hidden layer slabs and no jump connections:

FIG. 26F

Output of the Gaussian Slab of hidden layer

The two weight matrices (one leads to the slab, the other away from the slab):

$$WGI = \begin{bmatrix} -0.304511 & 0.156860 & 0.194150 & 0.109730 & -0.214814 & 0.313690 & -0.306358 & 0.020778 & -0.023027 & 0.094503 \\ 0.093666 & -0.061205 & 0.139971 & 0.031490 & -0.094618 & -0.083705 & -0.056244 & 0.060931 & -0.068565 & 0.208349 \\ -0.149501 & -0.121600 & -0.201030 & -0.105023 & -0.208799 & -0.244794 & 0.021268 & -0.196617 & -0.263198 & 0.019771 \\ 0.119571 & 0.106471 & 0.232342 & -0.288205 & -0.158461 & -0.221456 & 0.034158 & 0.147091 & 0.027795 & -0.093499 \end{bmatrix}$$

and $$WGO = \begin{bmatrix} -0.143488 & -0.114805 & -0.140507 & -0.073176 & -0.088738 \end{bmatrix}^T .$$

For $i = 1, \ldots, 4$, let $$s_i = \exp\left[-\left(\sum_{j=0}^{9} WGI_{i-1,j} y_j\right)^2\right]$$

and $$s_0 = 1.0.$$

The input from the Gaussian Slab to the output layer:

$$t = \sum_{j=0}^{4} WGO_j s_j.$$

FIG. 26G

Output of the Gaussian Complement Slab of Hidden Layer

The two weight matrices (one leads to the slab, the other away from the slab):

$$WCI = \begin{bmatrix} -0.110983 & -0.140247 & 0.135954 & -0.254746 & -0.054465 & -0.151304 & -0.184793 & -0.204899 & -0.131120 & 0.129406 \\ 0.300111 & 0.114792 & 0.001408 & 0.238157 & -0.256382 & 0.224609 & -0.196205 & 0.008663 & 0.037793 & -0.026505 \\ 0.132736 & 0.012252 & -0.209015 & 0.107662 & 0.263795 & 0.197985 & 0.188538 & 0.139959 & 0.106783 & -0.223848 \\ -0.163483 & -0.376954 & 0.289039 & -0.099885 & 0.143128 & 0.116539 & -0.009555 & -0.061872 & 0.143765 & -0.044218 \end{bmatrix},$$

and $$WCO = \begin{bmatrix} -0.168260 & -0.269478 & -0.054825 & -0.006776 & -0.263971 \end{bmatrix}^T.$$

For $i = 1, \ldots, 4$, let $$p_i = 1.0 - \exp\left[-\left(\sum_{j=0}^{9} WCI_{i-1,j} y_j\right)^2\right]$$

and $$p_0 = 1.0.$$

The input from the Gaussian Complement Slab to the output layer:

$$q = \sum_{j=0}^{4} WCO_j p_j.$$

FIG. 26H

Output of the Hyperbolic Tangent Slab of Hidden Layer

The two weight matrices (one leads to the slab, the other away from the slab):

$$WTI = \begin{bmatrix} -0.173508 & 0.016635 & 0.293693 & -0.152424 & -0.195091 & 0.246886 & 0.106956 & -0.230415 & 0.286641 & -0.190840 \\ 0.104152 & 0.832558 & 0.023314 & 0.093208 & 0.277480 & -0.050450 & 0.148019 & -0.023419 & 0.174769 & -0.289061 \\ -0.101116 & 0.545488 & -0.078117 & -0.360955 & -0.148834 & -0.096666 & 0.122698 & -0.089909 & -0.206334 & -0.169374 \\ 0.177989 & 0.451628 & -0.131347 & -0.132545 & -0.191001 & 0.153561 & -0.035409 & -0.035342 & 0.036760 & -0.103554 \end{bmatrix},$$

and $$WTO = \begin{bmatrix} -0.452268 & -0.177084 & -0.942018 & -0.547621 & -0.360800 \end{bmatrix}^T.$$

For $i = 1, \ldots, 4$, let $$p_i = \tanh\left(\sum_{j=0}^{9} WCI_{i-1,j} y_j\right)$$

and $$p_0 = 1.0.$$

The input from the Hyperbolic Tangent Slab to the output layer:

$$p = \sum_{j=0}^{4} WCO_j p_j.$$

FIG. 26I

Output of the Output Layer of ANN No. 2 (Def:P6)

$$ANN\_2t = [1/(1.0 + \exp\{-(t + u + q)\}) - 0.1] \cdot 0.7/0.8 + 0.7.$$

$$ANN\_2_{output} = \begin{cases} 1.4, & ANN\_2t > 1.4; \\ ANN\_2t, & 0.7 \leq ANN\_2t \leq 1.4; \\ 0.7, & ANN\_2t < 0.7. \end{cases}$$

Calculation of Output of ANN No.3 (Def:N5)

The calculations within ANN No. 3 are similar to that in ANN No. 2 except that the three hidden layer slabs each has eight neurons instead of four:

FIG. 26J

Output of the Gaussian Slab of hidden layer

The two weight matrices (one leads to the slab, the other away from the slab):

$$WGI = \begin{bmatrix} -0.311499 & 0.252345 & -0.243936 & -0.307765 & -0.046388 & 0.227230 & 0.228276 & -0.137408 & -0.290475 & -0.034533 \\ 0.078810 & 0.150768 & -0.084642 & -0.053571 & -0.091790 & 0.072183 & -0.153177 & -0.121494 & 0.267778 & -0.177731 \\ -0.185859 & -0.211585 & -0.212699 & 0.013215 & -0.220839 & 0.298793 & 0.130587 & 0.203839 & -0.162243 & 0.158944 \\ 0.200236 & 0.206995 & -0.203445 & 0.047468 & 0.062109 & 0.236341 & 0.226444 & -0.284303 & -0.120797 & -0.017088 \\ 0.047184 & 0.127987 & 0.293139 & 0.059886 & 0.169677 & 0.027382 & 0.293456 & -0.069593 & 0.046968 & -0.024906 \\ 0.027520 & -0.027361 & -0.047854 & 0.072129 & 0.164094 & -0.258089 & 0.273489 & -0.193461 & 0.081106 & 0.292569 \\ -0.071331 & -0.125573 & -0.236940 & -0.193265 & -0.030668 & -0.060839 & 0.085274 & 0.122095 & 0.221156 & 0.143412 \\ 0.242075 & -0.317035 & -0.296463 & 0.100556 & -0.118489 & -0.150338 & -0.065739 & -0.265594 & 0.138115 & -0.220718 \end{bmatrix}$$

and $$WGO = \begin{bmatrix} 0.096809 & -0.184366 & 0.165544 & 0.132342 & 0.074554 & 0.011272 & -0.143747 & -0.159079 & -0.093388 \end{bmatrix}^T.$$

For $i = 1, \ldots, 8$, let $$s_i = \exp\left[-\left(\sum_{j=0}^{9} WGI_{i-1,j} y_j\right)^2\right]$$

and $$s_0 = 1.0.$$

FIG. 26K

The input from the Gaussian Slab to the output layer:

$$t = \sum_{j=0}^{8} WGO_j s_j.$$

Output of the Gaussian Complement Slab of Hidden Layer

The two weight matrices (one leads to the slab, the other away from the slab):

$$WCI = \begin{bmatrix} 0.067068 & -0.277972 & 0.021562 & 0.062804 & -0.172936 & -0.279037 & -0.008672 & 0.218315 & 0.073614 & 0.038780 \\ 0.167845 & -0.364681 & -0.249520 & 0.035198 & -0.113620 & -0.048020 & -0.147505 & 0.175038 & 0.297389 & -0.201101 \\ -0.156261 & 0.055856 & -0.036449 & 0.074748 & -0.206363 & 0.258555 & 0.091588 & 0.069945 & -0.141724 & 0.129049 \\ -0.168007 & -0.292758 & -0.183210 & -0.188968 & 0.295630 & -0.338230 & 0.071248 & 0.137789 & -0.177583 & 0.076636 \\ -0.358500 & -0.357640 & 0.120204 & 0.013472 & 0.050170 & 0.275712 & -0.064446 & 0.060214 & 0.020285 & 0.158880 \\ -0.243064 & -0.014222 & -0.130094 & 0.280413 & 0.296799 & -0.142208 & -0.031750 & -0.062690 & 0.105171 & 0.115886 \\ 0.169814 & 0.060385 & -0.049205 & 0.119841 & -0.237874 & -0.149832 & 0.065611 & -0.164502 & 0.046325 & 0.242909 \\ 0.235109 & 0.121191 & -0.169709 & 0.258346 & 0.054250 & 0.142676 & 0.086200 & 0.150861 & -0.085953 & -0.228881 \end{bmatrix}$$

and $$WCO = \begin{bmatrix} 0.083002 & 0.311966 & 0.332433 & 0.077694 & 0.166723 & -0.430216 & 0.069231 & 0.267888 & -0.151407 \end{bmatrix}^T.$$

For $i = 1, \ldots, 8$, let $$p_i = 1.0 - \exp\left[-\left(\sum_{j=0}^{9} WCI_{i-1,j} y_j\right)^2\right]$$

FIG. 26L and $$p_0 = 1.0.$$

The input from the Gaussian Complement Slab to the output layer:

$$q = \sum_{j=0}^{8} WCO_j p_j.$$

Output of the Hyperbolic Tangent Slab of Hidden Layer

The two weight matrices (one leads to the slab, the other away from the slab):

$$WTI = \begin{bmatrix} 0.181852 & -0.220642 & -0.120407 & 0.044137 & -0.081303 & -0.084494 & 0.260226 & -0.130878 & -0.059755 & -0.200157 \\ 0.031246 & -0.027158 & -0.041711 & -0.159582 & -0.064631 & 0.200133 & 0.006474 & 0.261437 & 0.006734 & 0.269297 \\ 0.288767 & 0.061251 & -0.261471 & -0.205342 & 0.013150 & -0.279220 & -0.081970 & -0.106213 & 0.233317 & 0.051013 \\ 0.146882 & -0.217914 & 0.282214 & 0.199160 & 0.104252 & 0.011484 & -0.023025 & 0.133946 & -0.282981 & 0.101512 \\ -0.071505 & 0.438317 & 0.097794 & -0.043531 & 0.055028 & 0.063174 & -0.012403 & 0.088958 & 0.310749 & -0.257691 \\ -0.171471 & -0.349119 & -0.204849 & -0.169181 & 0.160670 & -0.066137 & 0.164127 & -0.203203 & 0.025718 & 0.265290 \\ 0.107109 & 0.166324 & 0.226326 & 0.009660 & 0.010181 & -0.241044 & -0.127065 & 0.160021 & -0.279324 & -0.199601 \\ -0.003873 & 0.088718 & 0.193063 & 0.137650 & -0.210456 & 0.273699 & -0.029180 & 0.208754 & 0.014949 & -0.226321 \end{bmatrix}$$

and $$WTO = \begin{bmatrix} 0.183252 & -0.052317 & 0.229279 & -0.120603 & 0.105757 & -0.452093 & 0.353077 & 0.050979 & -0.039570 \end{bmatrix}^T.$$

FIG. 26M

For $i = 1, \ldots, 8$, let $$p_i = \tanh\left(\sum_{j=0}^{9} WCI_{i-1,j} y_j\right)$$

and $$p_0 = 1.0.$$

The input from the Hyperbolic Tangent Slab to the output layer:

$$p = \sum_{j=0}^{8} WCO_j p_j.$$

Output of the Output Layer of ANN No. 3 (def:N5)

$$ANN\_3t = [1/(1.0 + \exp\{-(t+u+q)\}) - 0.1]/0.8 + 0.2.$$

$$ANN\_3_{output} = \begin{cases} 1.2, & ANN\_3t > 1.2; \\ ANN\_3t, & 0.2 \leq ANN\_3t \leq 1.2; \\ 0.2, & ANN\_3t < 0.2. \end{cases}$$

FIG. 26N

Calculation of Output of ANN No.4 (Def:W5)

The calculations within ANN No. 4 (Def:W5) are similar to that in ANN No. 3 except that the weight matrices are different. These matrices are listed below:

$$WGI = \begin{bmatrix} -0.317581 & 0.297632 & -0.244844 & -0.303867 & -0.048061 & 0.233394 & 0.226828 & -0.141339 & -0.285985 & -0.026430 \\ 0.078924 & 0.150609 & -0.087954 & -0.063621 & -0.106918 & 0.081330 & -0.162497 & -0.128922 & 0.263188 & -0.189672 \\ -0.194667 & -0.220458 & -0.210237 & 0.015062 & -0.229647 & 0.296875 & 0.143333 & 0.205021 & -0.154608 & 0.147912 \\ 0.195683 & 0.210590 & -0.202320 & 0.043847 & 0.062354 & 0.244261 & 0.213795 & -0.285744 & -0.129549 & -0.020266 \\ 0.039839 & 0.134480 & 0.292321 & 0.056541 & 0.164282 & 0.032858 & 0.284708 & -0.066090 & 0.037978 & -0.024098 \\ 0.014776 & -0.040319 & -0.047488 & 0.069085 & 0.142592 & -0.252673 & 0.274213 & -0.208170 & 0.080805 & 0.280503 \\ -0.063509 & -0.129254 & -0.235887 & -0.192264 & -0.043574 & -0.069777 & 0.087271 & 0.117392 & 0.221609 & 0.136861 \\ 0.250506 & -0.359633 & -0.295168 & 0.098983 & -0.105907 & -0.153153 & -0.062647 & -0.258460 & 0.138066 & -0.208586 \end{bmatrix}$$

and $$WGO = \begin{bmatrix} 0.058284 & -0.243129 & 0.150180 & 0.116091 & 0.030351 & -0.026612 & -0.171417 & -0.190026 & -0.175634 \end{bmatrix}^T.$$

FIG. 26O $$WCI = \begin{bmatrix} 0.089654 & -0.319349 & 0.021459 & 0.051869 & -0.164530 & -0.294179 & -0.005558 & 0.216657 & 0.071950 & 0.015807 \\ 0.196057 & -0.411242 & -0.248818 & 0.025449 & -0.095066 & -0.079907 & -0.152979 & 0.186887 & 0.283471 & -0.212626 \\ -0.154878 & 0.067380 & -0.037628 & 0.076077 & -0.202998 & 0.260595 & 0.088367 & 0.068578 & -0.142619 & 0.138350 \\ -0.159035 & -0.297571 & -0.185023 & -0.194276 & 0.280066 & -0.342067 & 0.068936 & 0.133413 & -0.177978 & 0.057195 \\ -0.378611 & -0.424962 & 0.132635 & 0.009711 & 0.047677 & 0.284020 & -0.042232 & 0.073446 & 0.017639 & 0.122110 \\ -0.250513 & -0.006974 & -0.131154 & 0.279919 & 0.290128 & -0.137515 & -0.034069 & -0.073119 & 0.108263 & 0.111758 \\ 0.146231 & 0.046483 & -0.038091 & 0.119774 & -0.237538 & -0.128281 & 0.077819 & -0.167480 & 0.049247 & 0.229180 \\ 0.235577 & 0.125237 & -0.167119 & 0.263776 & 0.054606 & 0.141706 & 0.091557 & 0.148260 & -0.079524 & -0.224271 \end{bmatrix}$$

and $$WCO = \begin{bmatrix} 0.044478 & 0.343728 & 0.382640 & 0.092186 & 0.156469 & -0.488488 & 0.067684 & 0.245493 & -0.151527 \end{bmatrix}^T .$$

$$WTI = \begin{bmatrix} 0.185914 & -0.223116 & -0.120221 & 0.049680 & -0.073055 & -0.087188 & 0.256513 & -0.139769 & -0.056984 & -0.188301 \\ 0.018800 & -0.072105 & -0.034853 & -0.171640 & -0.078024 & 0.205380 & 0.018605 & 0.278282 & -0.002852 & 0.232018 \\ 0.287595 & 0.096301 & -0.263217 & -0.199921 & 0.015438 & -0.276603 & -0.082866 & -0.109825 & 0.238246 & 0.061665 \\ 0.149936 & -0.231894 & 0.283239 & 0.198094 & 0.106940 & 0.007897 & -0.019705 & 0.135741 & -0.283984 & 0.100589 \\ -0.055912 & 0.510950 & 0.086551 & -0.030021 & 0.064546 & 0.057143 & -0.029228 & 0.072175 & 0.322555 & -0.209581 \\ -0.175119 & -0.402445 & -0.198701 & -0.181748 & 0.146292 & -0.067412 & 0.182934 & -0.192846 & 0.023265 & 0.226906 \\ 0.100464 & 0.144808 & 0.229419 & 0.006443 & 0.004543 & -0.237530 & -0.123392 & 0.162878 & -0.282155 & -0.216111 \\ -0.007425 & 0.063786 & 0.195472 & 0.139475 & -0.209694 & 0.275823 & -0.030529 & 0.207303 & 0.014163 & -0.226975 \end{bmatrix}$$

FIG. 26P and $WTO = [\ 0.144731\ \ 0.010671\ \ 0.232360\ \ -0.167825\ \ 0.140772\ \ -0.511001\ \ 0.386374\ \ 0.060320\ \ 0.002589\ ]^T$.

Calculation of QuiOs™ Index $$f_1 = \begin{cases} 1.0, & \text{ANN\_1}_{output} \geq 1.04; \\ (\text{ANN\_1}_{output} - 0.95)/0.09, & 0.95 \leq \text{ANN\_1}_{output} < 1.04; \\ 0.0, & \text{ANN\_1}_{output} < 0.95. \end{cases}$$

$$f_2 = \begin{cases} 1.0, & \text{ANN\_2}_{output} \geq 0.94; \\ (\text{ANN\_2}_{output} - 0.85)/0.09, & 0.85 \leq \text{ANN\_2}_{output} < 0.94; \\ 0.0, & \text{ANN\_2}_{output} < 0.85. \end{cases}$$

$$f_3 = \begin{cases} 1.0, & \text{ANN\_3}_{output} \geq 0.85; \\ (\text{ANN\_3}_{output} - 0.75)/0.1, & 0.75 \leq \text{ANN\_3}_{output} < 0.85; \\ 0.0, & \text{ANN\_3}_{output} < 0.75. \end{cases}$$

$$f_4 = \begin{cases} 1.0, & \text{ANN\_4}_{output} \geq 0.8; \\ (\text{ANN\_4}_{output} - 0.7)/0.1, & 0.7 \leq \text{ANN\_4}_{output} < 0.8; \\ 0.0, & \text{ANN\_4}_{output} < 0.7. \end{cases}$$

FIG. 26Q

We define an additional variable $T = \text{ANN\_3}_{\text{output}}/\text{ANN\_4}_{\text{output}}$, then $$f_5 = \begin{cases} 1.0, & T < 1.0; \\ (1.24 - T)/0.24, & 1.0 \leq T < 1.24; \\ 0.0, & T \geq 1.24. \end{cases}$$

$$\text{QuiOs}^{\text{TM}} = \frac{0.807413}{1.0 + \exp\left\{-1.1\left[\ln\left(1.0 + 10.0 \times \sum_{i=1}^{5} f_i\right) + 0.446843\right]\right\}}$$

FIG. 26R

COMPUTER ASSISTED METHODS FOR DIAGNOSING DISEASES

CROSS REFERENCE TO RELATED APPLICATIONS

The present application is a continuation of application Ser. No. 08/642,848, now U.S. Pat. No. 5,769,074, filed May 3, 1996, which is a continuation-in-part and claims priority to U.S. Provisional Application Ser. No. 60/001,425 filed Jul. 25, 1995. U.S. application Ser. No. 08/642,848 was also a continuation-in-part of U.S. application Ser. No. 08/323,446, filed on Oct. 13, 1994, now abandoned.

TECHNICAL FIELD

The present invention relates to methods for diagnosing, screening or prognosing diseases. More particularly, the present invention relates to a method for diagnosing, screening or prognosing diseases in humans or animals, and for determining the severity and cause of the disease.

The present invention further relates to a computer assisted method for diagnosing, screening or prognosing diseases, utilizing one or multiple neural networks to obtain a diagnostic index. In preferred embodiments of the present invention, the method is used to diagnose, and prognose diseases such as osteoporosis and cancers, including but not limited to ovarian, breast, testicular, colon and prostate cancer. In another preferred embodiment, the invention includes a system to receive patient data transmitted from data transmitting stations, to process these data through the trained neural networks to produce a diagnostic value or prognostic value, and to transmit these values to a remote data receiving means.

BACKGROUND OF THE INVENTION

As used herein, the term "disease" is defined as a deviation from the normal structure or function of any part, organ or system of the body (or any combination thereof). A specific disease is manifested by characteristic symptoms and signs, including both chemical and physical changes. A disease is often associated with a variety of other factors including but not limited to demographic, environmental, employment, genetic and medically historical factors. Certain characteristic signs, symptoms, and related factors can be quantitated through a variety of methods to yield important diagnostic information. For purposes of this application, the quantifiable signs, symptoms and/or analytes in biological fluids characteristic of a particular disease are defined as "biomarkers" for the disease. Current diagnostic and prognostic methods depend on the identification and evaluation of these biomarkers, both individually and as they relate to one another. Often the diagnosis of a particular disease involves the subjective analysis by a clinician, such as a physician, veterinarian, or other health care provider, of the data obtained from the measurement of the factors mentioned above in conjunction with a consideration of many of the traditionally less quantitative factors such as employment history. Unfortunately, this subjective process of diagnosing or prognosing a disease usually cannot accommodate all the potentially relevant factors and provide an accurate weighting of their contribution to a correct diagnosis or prognosis.

Generally, the pathological process involves gradual changes that become apparent only when overt change has occurred. In many instances, pathological changes involve subtle alterations in multiple biomarkers. It is uncommon that a single biomarker will be indicative of the presence or absence of a disease. It is the pattern of those biomarkers relative to one another and relative to a normal reference range, that is indicative of the presence of a disease. Additional factors including but not limited to demographic, environmental, employment, genetic and medically historical factors may contribute significantly to the diagnosis or prognosis of a disease, especially when considered in conjunction with patterns of biomarkers. Unfortunately, the subjective diagnostic process of considering the multiple factors associated with the cause or presence of a disease is somewhat imprecise and many factors that may contribute significantly are not afforded sufficient weight or considered at all.

When individual biomarkers do not show a predictable change and the patterns and interrelationships among the biomarkers viewed collectively are not clear, the accuracy of a physician's diagnosis is significantly reduced. Also, as the number of biomarkers and demographic variables relevant for the diagnosis of a particular disease increases, the number of relevant diagnostic patterns among these variables increases. This increasing complexity decreases the clinician's ability to recognize patterns and accurately diagnose or predict disease.

Prostate cancer affects numerous individuals each year and many of them are killed by the disease. The early and accurate diagnosis of prostate cancer has been very difficult to achieve with reliability and accuracy. However, early diagnosis of prostate cancer is essential to maximizing the possibility of successfully treating the disease. Current screening techniques include digital rectal examination (DRE), transurethral prostatic biopsy, and measurement of prostate specific antigen (PSA) in the blood. Reliance on serum PSA levels, especially low PSA levels, as a sole diagnostic measure of prostate cancer often provides unacceptable levels of inaccurate diagnosis. These screening techniques miss many cases of early stage prostate cancer resulting in growth of the cancer within the prostate gland and also outside the capsule of the gland. It is essential to diagnose this disease in the early stages, well before metastases have occurred.

In addition, diagnostic methods should be capable of distinguishing between benign prostatic hyperplasia (BPH) and prostate cancer and to distinguish between cases of cancer and non-cancer. What is also needed is a valid, reliable, sensitive and accurate technique that can diagnose or prognose prostate cancer at an early stage and also distinguish the various stages of prostate cancer which can be characterized as T1b, T2, T3 and TN×M1.

Osteoporosis and osteopenia provide another example of disease with multiple biomarkers, the following biomarkers collectively show characteristic changes in the presence of osteoporosis: calcium, phosphate, estradiol (follicular, mid-cycle, luteal, or post-menopausal), progesterone (follicular, mid-cycle, luteal, mid-luteal, oral contraceptive, or over 60 years), alkaline phosphatase, percent liver-ALP, and total intestinal-ALP. After measuring these biomarkers, a diagnosing clinician would next compare the measurements to a normal reference range. While some of the biomarkers may fall outside the normal reference range, others may fall clearly within the normal reference range. In some circumstances, all of the biomarker values may fall within a normal reference range. Presented with such data, a clinician may suspect that a patient has undergone some bone loss, but will be unable to reach a conclusive and meaningful diagnosis as to the presence of the disease osteoporosis.

The characteristic changes in biomarkers associated with some diseases are well documented; however, the quantitative interpretation of each particular biomarker in diagnosing a disease and determining a prognosis is not well established. The difficulties inherent in formulating a diagnosis from the analysis of a set of laboratory data is best illustrated by looking closer at conventional diagnostic methods for a specific disease. A discussion of the disease osteoporosis follows.

The term "osteopenia" as used herein means any decrease in bone mass below the normal. The term "osteoporosis" as used herein means a specific form of generalized osteopenia characterized by a decrease in bone density, low bone mass, and microarchitectural deterioration of bone tissue.

Osteopenia encompasses a group of diseases with diverse etiologies typified by reduction in bone mass per unit volume to a level below that which is necessary for adequate mechanical support. Osteoporosis is the result of the gradual depletion of the inorganic portion of the skeleton and can be caused by any number of factors. Primary osteoporosis is an age related disorder that is particularly common in women and is characterized by decreased bone mass in the absence of other recognizable causes. However, osteoporosis occurs in both men and women. In women it is recognized usually at the $5^{th}$ or $6^{th}$ decade, following menopause. In men osteoporosis is often recognized around their $6^{th}$ or $7^{th}$ decade of life.

Several demographic parameters are associated with enhanced risk of developing osteoporosis. The following is a partial list of individuals whose demographics and behavior place them at risk for developing osteoporosis:

Post-menopausal women

Cigarette smokers

Heavy users of alcohol

Users of a variety of drugs, such as steroids

Female runners and ballet dancers

Male marathoners consuming too few calories

Bulemics and anorexics

People with poor diets

People allergic to dairy products

People affected with cancer

Fair and slim women

All men and women over the age of 65.

In addition to being female, the three most significant risk factors are poor diet, lack of exercise, and being postmenopausal. Other risk factors which are associated with osteoporosis include racial factors such as Caucasian or Oriental ancestry, a fair complexion, and a family history of osteoporosis.

The onset of osteoporosis may be insidious or sudden, following trauma. The most common complaint associated with osteoporosis is back pain. Eventually, the pain may spread to the pelvis, the thorax, and the shoulders. In the spine, the vertebrae can compress, and the back can take on a "bent" appearance. Conditions such as kyphosis (humpback) or scoliosis may occur. If the spine becomes deformed, other body parts can be affected as well. For example, the ribs can be pushed against the pelvis, or the stomach can be pushed into the pelvis. In addition to spinal problems, osteoporosis can also lead to fractures of the hip, wrist, and ribs. These fractures can occur with only slight trauma and sometimes with no trauma at all. Mazess B., et al., "Bone Density of the Radius, Spine, and Proximal Femur in Osteoporosis," *J. of Bone and Mineral Research*, Vol. 3, pgs. 13–18, (1988); Riggs B. L., et al., "Involutional Osteoporosis", *New Engl. J. Med.*, Vol. 314, pgs. 1676–1686, (1986). The changes associated with osteoporosis are gradual so osteoporosis is often not detected in its early stages.

Calcium and phosphorus are the main components of the inorganic portion of the skeleton. Chemical analysis of blood may reveal calcium, phosphorus, and alkaline phosphatase within the normal range. However, an isoenzyme of alkaline phosphatase may be significantly increased. Increased bone resorption seen in osteoporotic patients, which occurs as a result of the action of osteoclasts, usually involves the dissolution of both minerals and organic matrix eventually leading to increased excretion of urinary hydroxyproline. Serum estradiol which is secreted almost entirely by the ovary is significantly decreased in these patients.

An early decrease in bone mass can be measured by non-invasive assessment of the skeleton by four widely available methods that are known to those skilled in the art, including single photon absorptometry, dual photon absorptometry (DPA), dual-energy x-ray absorptometry (DXA), and quantitative computed tomography (CAT scan). Several of these methods are used to measure mineral content in the bone, and some are relatively selective for certain bones or trabecular versus cortical bone. These methods also provide different levels of radiation exposure.

Magnetic resonance imaging (MRI) and positron emission tomographic (PET) techniques may also reveal information useful in the diagnosis of various diseases including osteopenia and osteoporosis by providing information concerning bone density and vitality.

Radiographic absorptometry (RA) is a method for non-invasive measurement of bone mineral x-rays of the hand. Radiographs, taken with a standard x-ray machine, are sent to a central laboratory for computer-controlled analysis.

Current standard diagnostic techniques, are not effective for early detection of osteoporosis. Changes seen in osteoporosis are very gradual, and often go undetected in the early stages of the disease. Osteoporosis is often not detected in its early stages because bone mass must be decreased by about 30% to 40% before it is apparent using standard x-ray diagnostic techniques. Preventing osteoporosis by detecting early bone loss is far better than identifying the disease at relatively advanced stages and subsequently attempting to prevent its progression. Once major deterioration has occurred and gaps exist between the ends of fractured trabecular bone, no current treatment can be expected to restore the lost bone. Thus, therapeutic efforts must be directed toward prevention and early recognition of the progressive disease so treatment can be instituted before essentially irreversible structural damage ensues. Cummings S. R., et al., "Should Perimenopausal Women Be Screened for Osteoporosis?", *Ann. Int. Med.*, Vol. 104, pgs. 817–823, (1986); Courpron P., "Bone Tissue Mechanisms Underlying Osteoporosis," *Orthop. Clin. North Am.*, Vol. 12, pgs. 545, (1981); Frost H. M., "Mechanical Determinants of Bone Modeling," *Metabol. Bone. Dis. Rel. Res.*, Vol. 4, pgs. 217–229, (1982). What is needed is a method for early detection and prediction of osteoporosis that considers the multiple biomarker and demographic variables associated with the disease.

One of the problems with the current methods for diagnosing osteoporosis is that the procedures do not give any information about the underlying cause of the osteoporosis, making it difficult to prescribe an appropriate course of treatment for the patient. For example, a common cause of postmenopausal osteoporosis is an estrogen deficit, which x-ray techniques cannot measure. Another problem inherent in the current diagnostic methods for osteopenia is that all of the current methods require expensive, sophisticated medical instrumentation to perform the bone density measurements. Additionally, patients must be exposed to x-rays. This makes a general screening of high risk populations impractical due to the expense and unavailability of the necessary instrumentation to the average clinic.

In view of the difficulties associated with extracting a diagnosis from the laboratory data for a set of predictive biomarkers, and also from demographic data optionally combined with biomarker data, there is need for automated diagnostic systems that are capable of complex pattern recognition. There have been several attempts at using computational models to achieve pattern recognition in diagnostics. One of the most popular computational methods for making diagnoses from multivariate laboratory data has been discriminate function analysis. However, diagnostic systems that rely exclusively on classical pattern recognition technology (geometric, syntactic, template, statistical) are not effective for evaluating the characteristic biomarker patterns of many disease states partially due to the inherent non-linear nature of the problem and a lack of known mathematical structure in the observed data. There is no clear set of rules that accurately describes how to analyze a set of biomarkers to reach a diagnosis.

In recent years, artificial neural networks have been gaining popularity as a means for recognizing and analyzing subtle diagnostic patterns in multivariate laboratory data. Neural networks possess the ability to discern patterns and trends too subtle or too complex for humans and conventional computational methods to identify. While humans can not easily assimilate more than two or three variables at once, neural networks can perceive correlations among hundreds of variables. Examples of areas in which neural networks have been explored for their value in clinical diagnosis and/or prognosis include:

psychiatry (See Mulsant, B. H., "A Neural Network as an Approach to Clinical Diagnosis", *MD Computing*, Vol. 7, pp. 25–36 (1990));

autism (See Cohen, I., et al., "Diagnosing Autism: A Neural Net-Based Tool", PCAI, pp. 22–25 (May/Jun. 1994); pediatric radiology (See Boone, J. M., et al., "Neural Networks in Radiologic Diagnosis. I. Introduction and Illustration", *Invest. Radiol.,* Vol. 25, pp. 1012–1016, (1990) and Gross, G. W., et al., "Neural Networks in Radiologic Diagnosis. II. Interpretation of Neonatal Chest Radiographs", *Invest. Radiol.,* Vol. 25, pp. 1017–1023 (1990));

breast cancer (See Astion, M. L., et al., "Application of Neural Networks to the Interpretation of Laboratory Data in Cancer Diagnosis", Clin. Chem., Vol. 38, No. 1, pp. 34–38 (1992); Wus Y., et al., "Artificial Neural Networks in Mammography: Application to Decision Making in the Diagnosis of Breast Cancer", *Radiology,* Vol. 187, pp. 81–87 (1993); Kappen, H. J., et al., "Neural Network Analysis to Predict Treatment Outcome", *Annals of Oncology,* Vol. 4, Supp. 4, pp. S31–S34 (1993); and, Ravdin, P. M., et al., "A practical application of neural network analysis for predicting outcome of individual breast cancer patients", *Breast Cancer Research and Treatment,* Vol. 22, pp. 285–293 (1992));

ovarian cancer (See Wilding, P., et. al., "Application of backpropogation neural networks to diagnosis of breast and ovarian cancer", Cancer Letters, Vol. 77, pp. 145–153 (1994)).

thyroid disease (See, Sharpe, P. K., et. al.; "Artifical Neural Networks in Diagnosis of Thyroid Function from in Vitro Laboratory Tests," *Clin. Chem.,* Vol. 39, No. 11, pps. 2248–2253 (1993));

prostate cancer (See Snow, P. S. et al., "Artificial Neural Networks in the Diagnosis and Prognosis of Prostate Cancer: A Pilot Study" *J. Urology,* Vol. 152: 1923–1926 (1994)).

cervical cancer (See U.S. Pat. No. 4,965,725 to Rutenberg); and, cardiology (See U.S. Pat. No. 5,280,792 to Leong et al. and Furlong, J. W., "Neural Network of Serial Cardiac Enzyme Data: A Clinical Application of Artifical Machine Intelligence", *Am. J. Clin. Pathol,* Vol. 96, No. 1, pp. 134–141 (July 1991).

Neural networks are capable of pattern recognition particularly suited to making diagnoses. Unlike current methods for arriving at a diagnosis from a logical set of rules, neural networks do not require explicit encoding of process knowledge in a set of rules. Neural networks learn from examples. Neural networks learn more efficiently when the data to be input into the neural network is preprocessed.

There are two basic approaches in computer assisted clinical pattern classification techniques. The first approach applies known knowledge and facts (physiological, anatomical, molecular biological, etc.) of a given disease process and attempts to establish links between observed or measured data and one of several possible classification classes. Such existing knowledge and facts are often expressed as rules (e.g. clinical expert systems), certain forms of numerical functions (e.g. statistical distributions in parametric statistical inferences), or even complex models that can only be described with systems of equations (e.g. pharmacokinetic models).

The second approach uses numerical procedures to adaptively construct and modify a numerical classification system based on available training data which are essentially sets of input values paired with known classification results. In this approach, the human expert knowledge is not or can not be expressed in an explicit form. Instead, the knowledge is implicitly provided in the training data with confirmed classifications. The extraction of such knowledge through supervised learning (learning from examples) and the adaptive construction of the classification system are left entirely to the learning algorithm. Classification systems with this second approach include various forms of neural network classifiers such as Multilayer Feedforward Perceptrons.

Both approaches have their shortcomings. The first approach uses explicit knowledge in the subject area to associate observed unknown data with a known class. However, in many practical situations, such knowledge is incomplete, or a portion of it cannot be expressed in explicit and precise terms, so that it can be directly coded into the classification system. On the other hand, the pure numerical pattern classification approach places the burden of constructing the classification system entirely to the adaptive learning process. The performance of the obtained system is limited to the amount and extent of information contained in the training data and the effectiveness of the learning algorithm in extracting such information, despite the fact that there may exist a tremendous amount of prior knowledge about the subject area. In some cases where there is no preprocessing such as preselection or scaling of the patient data, the training of a neural network may be extremely difficult if not impossible since the number of input variables may be too large and the relationship of these variables to a specific disease may be too weak to achieve the desired predictive accuracy.

Accordingly what is needed is an approach to diagnosing and prognosing disease that incorporates an apparatus and a system capable of accommodating a large number of factors, such as biomarker and demographic factors. This system should be capable of processing a large number of patients and patient variables such as biomarker and demographic factors. This approach to diagnosis and prognosis of disease should select factors with high predictive values, preprocess these factors, and input the data into a computer-based neural network or multiple neural networks in order to train the neural network(s) to predict or diagnose disease. These neural network(s) should produce a diagnostic index comprised of one or several output values indicative of the presence (diagnosis) or future occurrence (prognosis) of a disease. The system should possess the capacity to input patient data into the trained neural network and produce an output value to indicate if the patient has or will have the disease.

Furthermore, since clinicians will rarely have such computer-based neural network capabilities at their disposal, what is also needed is a system whereby patient data can be transmitted to a computer-based neural network as described above, which will receive the data, input it into the trained neural network, produce an output value indicative of a diagnosis or prognosis and then transmit the information concerning the diagnosis or prognosis to another location, such as the originating data transmitting station, or perhaps directly to the clinician's office. Such a system would provide access to sophisticated and highly trained prognostic and diagnostic neural networks which would enhance the accuracy of clinician's diagnostic and prognostic capability. This system should be capable of receiving high volumes of patient data and rapidly processing the data through the neural networks to obtain diagnoses and prognoses of disease.

Such a system could be used for diagnosis and prognosis of any disease or condition for which a neural network may be specifically trained.

SUMMARY OF THE INVENTION

The present invention is an apparatus and a process for diagnosing, screening or prognosing diseases. More particularly, the present invention relates to a computer-based method employing trained neural networks, and a process for diagnosing, screening or prognosing diseases in patients such as humans or animals, and for determining the severity and cause of the disease. This objective is accomplished by performing the following steps: collecting data about patients, such types of data optionally including biological, physical, demographic, racial, environmental, and medical historical data; digitizing the data selecting those data that are associated with the diagnosis of a disease; scaling digitized values; performing tests to analyze the discriminating power of these data; grouping individual data values; preprocessing these data; inputting selected data into a computer-based neural network in order to train the neural network; analyzing the contributions of individual data inputs to the neural network; selecting the optimally trained neural network based on performance, accuracy and cost, the neural network being trained to produce a diagnostic index; and inputting other patient data into the trained neural network to produce an output value which indicates whether the patient may have or be susceptible to the disease.

The present invention also includes an apparatus and process for rapidly diagnosing, screening or prognosing diseases in large numbers of patients, wherein the patient data is transmitted to a central facility from a remote location. At the central facility, patient data is received and introduced into a computer system which performs the following functions: analysis of the patient data to evaluate correctness of the data format; scaling the data to provide values for different types of in similar ranges; introduction of scaled patient data into a trained neural network for computation of an output value; comparison of the output value to a diagnostic index produced by the trained neural network; formulation of a diagnosis or prognosis based on this comparison; transmission of the diagnosis or prognosis to a remote location, optionally the location which sent the original patient data set or the office of a health care provider.

This embodiment of the present invention permits the rapid evaluation of large data sets comprised of patient data including biomarker data and demographic data, formulation of a diagnosis or prognosis for a particular disease or for several diseases, and rapid transmission of the results to the health care provider or facility responsible for the patient. This system not only provides improved diagnostic capability resulting in enhanced health to the patient, but also reduces cost due to wasted time, delayed treatment and incorrect diagnosis. This system provides the capability to screen numerous patient samples for diagnosis and prognosis of disease and enables health care providers to access sophisticated computer-based neural networks specifically trained to diagnose disease with high levels of precision and accuracy.

In one embodiment, the present invention may be used to rapidly and accurately diagnose and prognose prostate cancer, even at very early stages. In this embodiment, large numbers of patient data sets comprised of biomarkers and optionally demographic data, may be screened rapidly and economically to diagnose and predict prostate cancer with high precision and accuracy. In addition, this invention facilitates determination of the stage of prostate cancer and distinguishes between benign prostatic hyperplasia and prostate cancer.

In another embodiment, the present invention may be used to rapidly and accurately diagnose and prognose osteoporosis and osteopenia, even at very early stages. In this embodiment, large numbers of patient data sets comprised of biomarkers and optionally demographic data, may be screened rapidly and economically to diagnose and predict osteoporosis and osteopenia with high precision and accuracy. In addition, this invention facilitates determination of the extent of osteoporosis and osteopenia and provides information about the causative variables.

It is an object of this invention to diagnose and prognose any disease in a patient for which adequate data, such as biomarker and demographic data, exist in a patient population to specifically train a neural network to produce a diagnostic index with a high level of predictive utility, and to accurately and reliably diagnose the disease in new sets of patient data. Large numbers of multivariable patient data sets may be screened for the presence of a disease or to prognose a disease using this system.

Accordingly, it is an object of the present invention to provide a method for diagnosing, screening or prognosing and determining the severity of a disease.

Still another object of the present invention is to provide a system comprised of a method and apparatus comprising a computer-based trained neural network system that will diagnose, screen or prognose and determine the severity of a disease by receiving patient data from another location through a data receiving means, transmitting the data into a computer or through several computers containing a computer-based trained neural network, processing the patient data through the trained neural network, or optionally multiple trained neural networks, to produce an output value, which is a diagnostic value, transmitting these diagnostic values to another location, optionally to another computer for transmission to a remote location, optionally comprising a computer, or other data receiving means. This system may contain one or several computers and one or several trained neural networks.

It is another object of the present invention is to provide an apparatus for diagnosing, screening or prognosing and determining the severity of a disease.

A feature of the present invention is that it provides a method for screening, prognosing and diagnosing prostate cancer.

Another feature of the present invention is that it provides a method for screening, prognosing and diagnosing osteoporosis and-osteopenia.

Still another feature of the present invention is that it provides a method for screening, prognosing and diagnosing breast cancer.

Yet another feature of the present invention is that it provides a method for screening and diagnosing ovarian cancer.

Another feature of the present invention is that it provides a method for screening, prognosing and diagnosing colon cancer.

An additional feature of the present invention is that it provides method for screening, prognosing and diagnosing testicular cancer.

An advantage of the present invention is that it provides a method for diagnosing disease which will provide a better understanding of the probable cause of the disease.

Another advantage of the present invention is that it provides a method for diagnosing cancer which will provide a better understanding of the probable cause of the cancer.

Another advantage of the present invention is that it provides a diagnostic test for cancer which can be used to rapidly and economically screen data sets from large numbers of patients.

Still another advantage of the present invention is that it provides a test for osteoporosis which will also give information as to the underlying cause of the osteopenic condition.

Another advantage of the present invention is that it provides a diagnostic test for osteoporosis which can be used to screen large numbers of individuals.

An advantage of the present invention is to provide a method for diagnosing osteoporosis and determining the underlying cause of the osteopenia without having to subject the patient to radiation.

These and other objects, features and advantages of the present invention will become apparent after a review of the following detailed description of the disclosed embodiment and the appended claims.

BRIEF DESCRIPTION OF THE FIGURES

FIG. 1 illustrates a feed forward neural network having multiple outputs.

FIG. 2 illustrates a feed forward neural network having a single output.

FIGS. 5A, 5B and 5C show the training data used to construct the prostate cancer neural network prognostic system.

FIGS. 6A, 6B, 6C and 6D show the training data used to construct the neural network ProstAsure™ system for prostate cancer detection.

FIGS. 7A–7I shows the test data used to construct the neural network ProstAsure™ system for prostate cancer detection.

FIGS. 8A, 8B, 8C and 8D show the training data used to construct the QuiOs™ osteoporosis neural network diagnostic system.

FIGS. 9A–9I show the testing data used to test the QuiOs™osteoporosis neural network diagnostic system.

FIG. 10 demonstrates the sensitivity and specificity of the QuiOs™ system in diagnosing osteopenia.

FIG. 17 provides ProstAsure™ reference ranges for normal, BPH and prostate cancer in different age groups.

FIG. 18 provides diagnostic guidelines for samples in the ProstAsure™ test data set.

FIG. 19 shows statistically significant ProstAsure™ results in the diagnosis normal, BPH and cancer patients.

FIG. 20 demonstrates ProstAsure™ results in 193 test cancer cases.

FIG. 24 shows the sensitivity and specificity of ProstAsure™ in detecting and discriminating prostate cancer and identifying normal and BPH patients.

FIGS. 25A–25G are a mathmetical description of the ProstAsure™ algorithm.

FIGS. 26A–26R are a mathematical description of the QuiOs™ algorithm.

DETAILED DESCRIPTION

Figure 3:
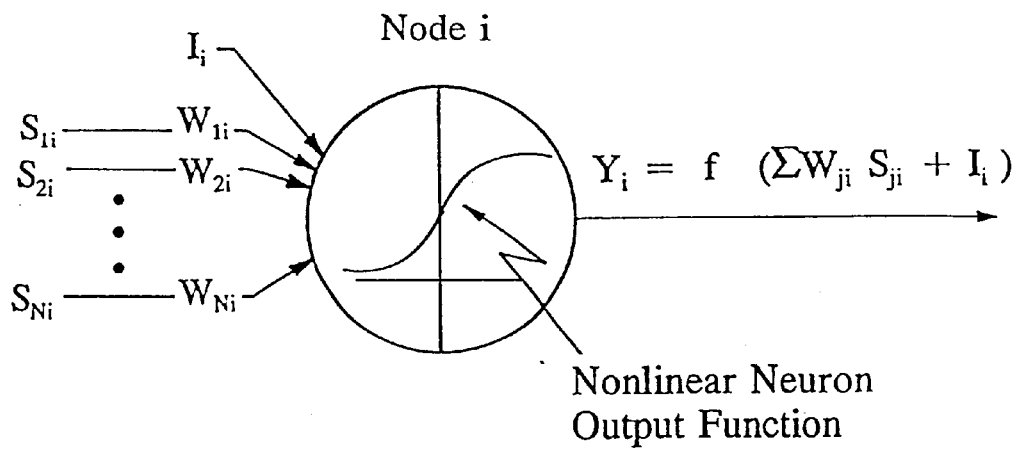
FIG. 3 is an equation illustrating the mathematical relationship between the input and output of a typical neuron.

The following patent applications are incorporated herein by reference in their entirety: U.S. Provisional Application Ser. No. 60/001,425 filed Jul. 25, 1995; U.S. application Ser. No. 08/472,632 filed Jun. 7, 1995; PCT Application PCT/US95/01379 filed Feb. 2, 1995; U.S. application Ser. No. 08/323,446 filed on Oct. 13, 1994; U.S. application Ser. No. 08/315,851 filed on Sep. 30, 1994; U.S. application Ser. No. 07/990,772 filed on Dec. 14, 1992; PCT Application PCT/US92/10879 filed Dec. 14, 1992; U.S. application Ser. No. 07/964,486 filed on Oct. 21, 1992; U.S. application Ser. No. 07/806,980 filed on Dec. 12, 1991.

As used herein, the term "disease" is defined as a deviation from the normal structure or function of any part, organ or system of the body (or any combination thereof). A specific disease is manifested by characteristic symptoms and signs, including biological, chemical and physical changes and is often associated with a variety of other factors including but not limited to demographic, environmental, employment, genetic and medically historical factors. Certain characteristic signs, symptoms, and related factors can be quantitated through a variety of methods to yield important diagnostic information.

The term "patient" refers to any human or animal.

For purposes of this application, the quantifiable signs, symptoms and/or analytes in biological fluids and tissues characteristic of a particular disease are defined as "biomarkers" for the disease. Current diagnostic and prognostic methods depend on the identification and evaluation of these biomarkers, both individually and as they relate to one another. The term "biomarkers" includes all types of biological data from a patient.

The patient data may include a variety of types of data which have some association with the disease. The information may be biological. Such data may be derived from measurement of any biological parameter. Such substances include, but are not limited to, endocrine substances such as hormones, exocrine substances such as enzymes, and neurotransmitters, electrolytes, proteins, carbohydrates, growth factors, cytokines, monokines, fatty acids, triglycerides, and cholesterol.

Other types of biological data may be derived from histological analysis of organs, tissues or cells removed from patients, including histological analyses performed at the light microscopic and electron microscopic levels utilizing any number of techniques including, but not limited to, structural analysis, histochemical, immunocytochemical, in situ hybridization, and autoradiographic techniques.

Biological data may be derived from analysis of cells removed from patients and grown in culture. Various characteristics of these cells may be examined histologically and biochemically. For example, cells removed from a patient and placed in culture may be examined for the presence of specific markers associated with the presence of a disease. Cells may be examined for their metabolic activity or for the products made and released into the culture medium.

Biological data about a patient includes results from genetic and molecular biological analysis of the nuclear and cytoplasmic molecules associated with transcription and translation such as various forms of ribonucleic acid, deoxyribonucleic acid and other transcription factors, and the end product molecules resulting from the translation of such ribonucleic acid molecules.

Also included in the category of biological data are the various structural and anatomical analytical methods used with patients such as radiographs, mammograms, fluorographs and tomographs, including but not limited to X-ray, magnetic resonance imaging, computerized assisted tomography, visualization of radiopaque materials introduced into the body, positron emission tomography, endoscopy, sonograms, echocardiograms, and improvements thereof.

Biological data also includes data concerning the age, height, growth rate, dental health, cardiovascular status, reproductive status (pre-pubertal, pubertal, post-pubertal, pre-menopausal, menopausal, post-menopausal, fertile, infertile), body fat percentage, and body fat distribution. Biological data also includes the results of physical examinations, including but not limited to manual palpation, digital rectal examination, prostate palpation, testicular palpation, weight, body fat amount and distribution, auscultation, testing of reflexes, blood pressure measurements, heart and related cardiovascular sounds, vaginal and other gynecologic examinations, including cervical, uterine and ovarian palpation, evaluation of the uterine tubes, breast examinations, and radiograpic and infrared examination of the breasts.

Additional biological data can be obtained in the form of a medical history of the patient. Such data includes, but is not limited to the following: medical history of ancestors including grandparents and parents, siblings, and descendants, their medical problems, genetic histories, psychological profiles, psychiatric disease, age at death and cause of death; prior diseases and conditions; prior surgeries; prior angioplasties, vaccinations; habits such as exercise schedules, alcohol consumption, cigarette consumption and drug consumption; cardiac information including but not limited to blood pressure, pulse, electrocardiogram, echocardiogram, coronary arteriogram, treadmill stress tests, thallium stress tests and other cardiovascular imaging techniques. All of the aforementioned types of biological data are considered as "biomarkers" for the purposes of the present application.

The term "biological fluid" includes, but is not limited to, blood, serum, cerebrospinal, peritoneal, salivary, lacrimal, peritoneal, reproductive, intraocular, digestive, respiratory, pleural, pericardial, lymphatic, urine, intracellular and extracellular fluids, and neural fluids.

The term "demographic data" includes information concerning the patient's race, species, sex, ethnicity, environment, exposure to environmental toxins and radiation, stress level, behavioral patterns, previous occupations and current occupation. Demographic data may also be used to provide patient information that is useful in the diagnosis and prognosis of disease.

The present invention provides a method for diagnosing, screening or prognosing a disease in a patient comprising the steps of measuring the concentrations of a predetermined set of biomarkers known to be associated with the disease; converting these concentrations to digitized values; preprocessing the digitized values to make preprocessed values; and sending the preprocessed values to a computer-based neural network in order to train the neural network to diagnose or prognose the disease, whereby the diagnostic index from the neural network indicates when the patient has the disease or may develop the disease.

The present invention also comprises an apparatus for diagnosing, screening or prognosing a disease in a patient comprising a means for digitizing the concentrations of a predetermined set of biomarkers known to be associated with the disease from the patient; a means for preprocessing the digitized values; and a computer-based trained neural network coupled to the digitizing and scaling means for generating network output values; means for comparing the output values from the neural network to the diagnostic index to produce a diagnostic value which indicates when the patient has the disease or may develop the disease.

In accordance with the first embodiment of the present invention, a trained neural network is utilized to determine a diagnostic index corresponding to the presence and severity of a disease by analyzing a set of predetermined biomarkers or demographic data for that disease. In accordance with the invention, the concentrations of certain biomarkers or demographic data related to the incidence of a particular disease are determined for a patient. These data are converted to digitized values. These digitized values are then preprocessed (scaling, truncation, linear/non-linear combination, etc.) and the preprocessed values, optionally together with one or several secondary values computed from the original values are then sent to a trained neural network to yield a -diagnostic index. Preprocessing of the data occurs at this stage and serves to decrease the burden on the neural network and enhance the accuracy and sensitivity of the neural network for diagnosis and prognosis of disease. A neural network is trained by introducing a population of patients in which a disease state is known, along with the biomarker values or demographic data for those patients and "teaching" the neural network to recognize the patterns in the biomarkers. After the neural network is trained, biomarker values from patients with unknown disease states are introduced to the trained neural network. The neural network then processes the information to produce an output value whereby the output values from the neural network are diagnostic values which indicate whether the patient has the disease or may develop the disease.

Although not wanting to be bound by this statement, the inventors propose that the artificial neural network, especially the multi-layer feedforward network, may, through their weight connections, correspond to data patterns that are important for categorizing diseases. Additionally, the neural network can identify unique patterns of data associated with a variety of disorders that may help to classify borderline cases that do not appear to fit into either a malignant or benign pattern.

Multiple Neural Networks

The present invention also comprises a method for diagnosing, screening or prognosing a disease in a patient comprising the steps of measuring the concentrations of a predetermined set of biomarkers known to be associated with the disease from the patient, digitizing the concentrations preprocessing the digitized values to make preprocessed values, scaling the digitized values of the analytes, and introducing the preprocessed values to a first trained neural network, and sending the output value from the first neural network and a second set of predetermined biomarkers, which could include one or more of the biomarkers in the first set of predetermined biomarkers, to a second trained neural network, whereby the output values from the second neural network are compared to the diagnostic index to produce a diagnostic value which indicates when the patient has the disease or may develop the disease.

A second embodiment of the present invention involves a two step analysis of the biomarkers by neural network. This avoids the bias created by a dominant predictive variable when training a network. The dominant biomarker or predictive variable is excluded from the first analysis by neural network and is then included in a second analysis by neural network. For example, if age is thought to be the dominant predictive variable in the diagnosis of osteoporosis, that variable is not included in the training of the first neural network, and the training data set is limited to the other selected biomarkers. After obtaining a diagnostic index using the first set of biomarkers, a second neural network is trained using the diagnostic index and the entire set of input variables, including age, to yield another diagnostic index. The final diagnostic index is a composition of an artificial neural network generated index and results from heuristic analysis using other non-numerical patient information.

In another embodiment, the present invention provides a system, including the ProstAsure™ system, comprising an apparatus and method for diagnosing, screening or prognosing prostate cancer in patients. In this embodiment, data obtained from analysis of biomarkers and optionally from demographic information is preprocessed (e.g. scaled) and input into a trained neural network. Prostate specific antigen (PSA), prostatic acid phosphatase (PAP), and three forms of creatine kinase (BB, MB, and MM) are used as the biomarkers in this invention. It is to be understood that other biomarkers and demographic data may be used in this invention. For example, the results of a digital rectal examination in which the prostate is palpated may optionally be combined with other biomarkers or demographic data. The trained neural network provides an output value which indicates whether the patient has prostate cancer. The trained neural network is capable of providing highly accurate diagnoses and prognoses at early stages in the progression of prostate cancer, thereby displaying a high degree of sensitivity and specificity. The stage of prostate cancer is determined, even at very early stages in the disease. In addition, this invention distinguishes benign prostatic hyperplasia from prostate cancer, and distinguishes prostate cancer from non-cancerous conditions.

Another specific embodiment of the present invention includes a system comprising a method and apparatus for diagnosing and determining the severity and underlying cause of osteopenia and osteoporosis in a patient using a computer-based trained neural network. In a preferred embodiment, the method comprises determining the serum level of the following biomarkers: calcium, phosphate, total alkaline phosphatase, an alkaline phosphatase isoenzyme, estradiol, and progesterone. The alkaline phosphatase isoenzyme is preferably t-lymphocyte derived alkaline phosphatase or blood, liver or intestinal alkaline phosphatase isoenzyme. Optionally, the age of the patient or demographic data may be included in the trained neural network. The bone density coefficient that is calculated by the algorithm correlates to a very high degree to bone density as measured by standard methods, such as radiographic absorptometry, quantitative computed tomography, dual photon absorptometry and direct measurement of bone density. The bone density coefficient that is measured is then compared to an osteopenic severity scale.

Another embodiment of the present invention is directed to a computer assisted method for screening, prognosing and diagnosing diseases utilizing a neural network to obtain a conclusive diagnosis. The present invention can be adapted to existing diagnostic devices that have a collection means, a sample detecting means capable of detecting the quantity of an analyte in a biological fluid and a means of either printing or displaying the results of the tests on video display means.

The inventors have discovered that biomarkers collectively alter in response to a disease process, and collectively constitute a new diagnostic biomarker with better disease predictability than the individual biomarkers. When the biomarkers are processed and analyzed as a group in a computer-based trained neural network to yield a single diagnostic index, the sensitivity and specificity of the diagnosis is increased, making it possible for a physician to detect the presence of a disease earlier and with greater precision, or estimate a prognosis with greater precision, than by analysis of the individual biomarkers.

In accordance with one embodiment of the present invention, a biological fluid or several biological fluids are first collected from a patient. Biomarkers associated with a specific disease are measured in the biological fluids using standard laboratory techniques, to determine their concentrations, or in some cases their presence or absence. It is to be understood that this process can be carried out automatically in conventional diagnostic machines. For purposes of illustration, descriptions of the methods for obtaining the values for the biomarkers for osteopenia and also for prostate cancer are provided elsewhere in this section.

The biomarkers relied upon to diagnose a disease by the method of the present invention must be predictive of the suspected disease and must be statistically significant for analysis by a neural network. The selection of biomarkers that offers statistically significant discriminating power in the diagnosis of disease involves several steps. First an inventory of biomarkers that have shown certain relevancy in the diagnosis of the disease of interest must be conducted. In general, only the biomarkers that reflect different aspects of the disease process or other diagnostic information need to be included. Second, the selected biomarkers need to have a reasonable diagnostic value in terms of sensitivity, specificity, and positive and negative predictive powers. The design and implementation of experimental protocol from which the biomarkers are developed and evaluated should also be considered. Third, if the number of candidate biomarkers is large, a formal discriminating power analysis may be conducted. However, many of the standard statistical analysis methods may not be adequate for highly nonlinear classification problems. Typically, biomarker values and demographic data values are scaled to provide relatively similar ranges of values between different biomarkers or demographic variables. In this manner, the variances due to the different numerical ranges inherent in the measurement of different variables are decreased. Preprocessing of the input variables comprised of biomarkers and other demographic data is an important step in the training of the neural network. If the number of candidates are not too large, they may be all included in the initial attempt of neural network training. If one or several of the input biomarkers to the network are irrelevant to the classification decision making process, it will be reflected in the network connection weights of the trained neural networks. These values may then be removed from the biomarker set for a particular disease. Other methods for evaluating the statistical significance of a biomarker selected for analysis by neural network and selecting biomarkers for training a neural network are well known in the art.

Biomarkers which meet the criteria delineated above, namely, they are predictive of a particular disease and statistically significant for analysis by neural network, are identified below for several examples of diseases including prostate cancer, osteoporosis, ovarian cancer, colon cancer, breast cancer, and testicular cancer. It is to be understood that these biomarkers for the specific diseases described below are examples of the present invention and are not to be construed as imposing any limitation on the scope of the present invention

| Ovarian Cancer I | Prostate Cancer I | Colon Cancer |
|---|---|---|
| LASA-P ® | LASA-P ® | LASA-P ® |
| CA125 | PAP | CA 19-9 |
| DM/70K | PSA | CEA |
| Ovarian Cancer II | | Prostate Cancer II |
| CA125 | | PAP |
| MCSF | | PSA |
| OVX1 | | CK-MB |
| LASA | | CK-MM |
| CA7-24 | | CK-BB |
| CA19-9 | | |
| Breast Cancer | Testicular Cancer | Osteoporosis |
| LASA-P ® | LASA-P ® | Calcium |
| CEA | AFP | Phosphate |
| HER2/neu in Plasma | HCG-Beta | Estradiol |
| | CA 15-3 ® | Progesterone |
| | | ALP |
| | | ALP Isoenzyme 1 |
| | | ALP Isoenzyme 2 |

A key to the abbreviations used above is provided below:

| | |
|---|---|
| AFP: | Alpha-Fetoprotein |
| CA125: | Cancer Antigen 125 |
| CA 15-3 ®** | Breast Antigens 115D8/DF3 |
| CA 19-9: | Carbohydrate Antigen 19-9 |
| CEA: | Carcinoembryonic Antigen |
| CK-MM | Creatine kinase, MM subfraction |
| CK-MB | Creatine kinase, MB subfraction |
| CK-BB: | Creatine kinase, BB subfraction |
| DM/70K: | Ovarian marker NB/70K |
| HCG-Beta: | Human Chorionic Gonadotropin, Beta Sub-Unit |
| HER 2/neu in Plasma: | c-erb B-2 (HER2/neu) oncoprotein in plasma |
| LASA-P ®*: | Lipid-Associated Sialic Acid in Plasma |
| M-CSF | Macrophage colony-stimulating factor |
| PAP: | Prostatic Acid Phosphatase |
| PSA: | Prostate Specific Antigen |

*LASA-P is a registered trademark of DIANON Systems, Inc.
**CA 15-3 is a registered trademark of Centocor, Inc.

A large number of diseases may be diagnosed in accordance with the method of the present invention. To be suitable for diagnosis by the present method, biomarkers and demographic data for the disease must be quantifiable. The biomarkers and demographic data must also be predictive of the disease and must be statistically significant relative to one another. The method of the present invention is equally suited to the diagnosis of any disease in which biomarkers and demographic data can be identified, including but not limited to infectious diseases, and genetic abnormalities.

After determining the biomarkers for a disease, the biomarker values are digitized, preprocessed and analyzed by a computer-based, trained neural network to yield a single diagnostic value. The most common neural network architecture for pattern classification problems is the feedforward network, which typically consists of an input layer, one or more hidden layers, and an output layer. FIGS. 1 and 2 illustrate the arrangement of neurons in two different feedforward networks.

The elements that make up each layer of a neural network are referred to as neurons or nodes. Inputs are fed forward from the input layer to the hidden layers and then to the output layer. The number of neurons in each layer is determined before the network is trained. Typically, there is one input neuron or node for each input variable, and one output node for each output. The inputs to the neural network are predictor variables. These predictor variables can be quantitative or qualitative. Neural networks make no data distribution assumptions and can simultaneously use both quantitative and qualitative inputs. In the present invention, the biomarker values, and the optionally generated secondary values are rescaled during preprocessing to values between 0.0 and 1.0 or between −1.0 and 1.0, constitute the input variables.

The outputs of the network represent output categories. For example, a malignancy may be represented by maximal output of the malignant output neuron and silence of the benign neuron, whereas a benign process is represented by maximal output of the benign neuron and silence of the malignant neuron. A simple arithmetic function combines the outputs of the two neurons to yield a single diagnostic index. In the alternative, a single output neuron may be used. An output of greater than 0.5 would indicate a malignancy and an output of less than 0.5 would indicate a benign condition. In this way a diagnostic index is directly obtained. Alternatively, a reversed denotation could be used.

The number of hidden layers and the number of nodes in the hidden layers are configurable parameters that have a significant influence on the performance of the network. In practice, the optimal number of hidden neurons is determined empirically. The means for determining the optimum number of hidden neurons is well known to those skilled in the art and depends on the complexity of the problem being solved.

In the present invention, one embodiment of the neural network is a multi-layer feedforward perceptron using a backpropogation training algorithm. The number of hidden layers and the number of neurons in each hidden layer was determined to adequately match the level of complexity of the diagnostic problem. With the assumption that the samples in the training set are representative of all possible situations encountered in real applications with no significant contradictions, and the number and stratification of samples in the generalization and cross-validation test are statistically adequate, the criteria outlined below are used to determine if a chosen network configuration is appropriate.

If the network continues to fail to correctly classify large portions of the samples in the training set, even after many adjustments of training algorithm parameters, the network complexity should be increased.

On the other hand, if the network achieves a high rate of correctly classifying the training set but fails to accurately classify a large number of samples in the testing set, network structure is probably too complex for the problem being solved, i.e. it has sufficient inherent flexibility to fit the training data set, but not sufficient predictive power to classify the test data set. If this is the case, the number of neurons in the hidden layers should gradually be reduced, or, if there are multiple hidden layers, the hidden layers should be gradually reduced.

It is also possible to achieve generalization with a neural network of slightly too many hidden neurons. This is done by periodically testing a partially trained neural network with cross-validation test data during training, and stopping at the moment when the cross-validation error reaches a minumum value and starts to increase.

It is usually not always necessary to have a large training sample set. If the samples in a training set have already represented all possible cases with adequate statistical significance, the addition of new samples generally does not increase the amount of information in the training samples. Instead it may decrease the useful information to noise ratio in the samples. At the other extreme, too small a training set will generally not be able to cover all possible variations in the population. The resultant network often simply memorizes all the cases in the training set and does not generalize at all.

The input and output layers are not directly connected. Every input neuron is connected to every neuron in the following hidden layer and neuron in a hidden layer is connected to every neuron in the following adjacent hidden layer or output layer, depending on the number of hidden layers. Each of the multiple connections to a particular neuron is weighted. In the hidden and output layers, each node sums the input activations, multiplied by the respective connection weights plus a bias term. The weighted sum then passes through a non-linear output function, typically a sigmoidal function, which gives the network the ability to represent complex non-linear relationships. A neuron fires if the sum of the weighted inputs to it are greater than a threshold value. As illustrated in FIG. 3, once a neuron is above a threshold, the magnitude of its output is a sigmoid function of the net input. The end result of activity in the neural network is the net output, a complex nonlinear function of the inputs.

In summary and in accordance with the present invention, first the values of the biomarkers or demographic variables for a specific disease are determined and scaled. The biomarkers are fed forward from the input layer to the hidden layer (or layers) and then to the output layer of the neural network. The number of neurons in the input layer is determined before the network is trained and corresponds to the number of biomarkers predictive for a specific disease. The biomarkers are preselected and preprocessed biomarker values are. There is one input neuron for each diagnostic variable or biomarker, and one output neuron for each desired output. Other than the identified biomarkers, diagnostic variables may include demographic information. The number of neurons in the output layer depends on the type of output desired. The number of neurons in the hidden layer is determined empirically during training.

The neural network used for diagnosing a specific disease must be trained to do so. In accordance with the present invention in one embodiment, the neural network is trained by back propagation. Back propagation refers to the technique of training a neural network to accurately model a set of input and output examples by determining the best connection weights between the values, and is well known in the art. Other techniques which may be used to train a neural network for purposes of this invention may include any other non-linear global optimization technique, such as the genetic search algorithm; however, the feed forward, back propagation network is most popular. At the initial stages of training the neural network, the connection weights in the network are randomized. The training data are then presented to the network one datum at a time. In accordance with the present invention, the training data consists of the biomarker values or demographic values for a group of patients, and the diagnosis for each of those patients. The biomarker values and, optionally, demographic values are digitized and preprocessed, and the preprocessed values are the input variables used to train the network. For each patient, the network uses the patient's preprocessed values to estimate a diagnosis, which is then compared to the actual diagnosis. If the network's diagnosis is correct, then the connection strengths and thresholds within the network are not changed, and the next patient is presented to the network. If the estimate of the diagnosis is not correct, the connection weights and thresholds in both the hidden layer and the output layer are adjusted to reduce the size of the classification error. After adjustments are made, the next patient is presented. Training proceeds until all patients in the training group are correctly classified or some preset stopping criteria are satisified (e.g. a maximum number of iterations).

When training the neural network, the trainer may set the decision limits regarding the definition of a classification error, i.e. an incorrect diagnosis. The relevant parameter is the error tolerance, which specifies how close the estimated output has to be to the actual output to be correct. For example, if two output neurons are used and the training tolerance is set at 5%, the estimate of malignancy is considered correct if the malignant output neuron fires at 95% of maximum and the benign neuron fires at 5% of maximum. Similarly, a correct estimate of a benign diagnosis means that the benign output neuron first at 95% of maximum, while the malignant neuron fires at 5% of maximum. The methods for determining a classification error are well known to those skilled in the art.

In a preferred embodiment of this invention, if a single output neuron is used, a benign normal diagnosis is set at an output of 0.1 and a malignant or abnormal diagnosis is set at an output of 0.9. Alternatively the reversed denotation can be used. Error tolerance is an adjustable parameter and is significant in determining the success of the network at making an accurate diagnosis.

After the neural network is trained for the desired disease, biomarker values and optionally demographic values from patients with unknown disease conditions and possibly no disease are digitized, preprocessed and introduced to the trained neural network. The neural network then processes the information to produce a value corresponding to a diagnosis of the presence or absence of the particular disease. In accordance with the present invention, this is accomplished by using either one single output neuron or multiple output neurons. If more than one output neuron are used, the output from the neurons are combined to generate a single diagnostic index.

Figure 4:
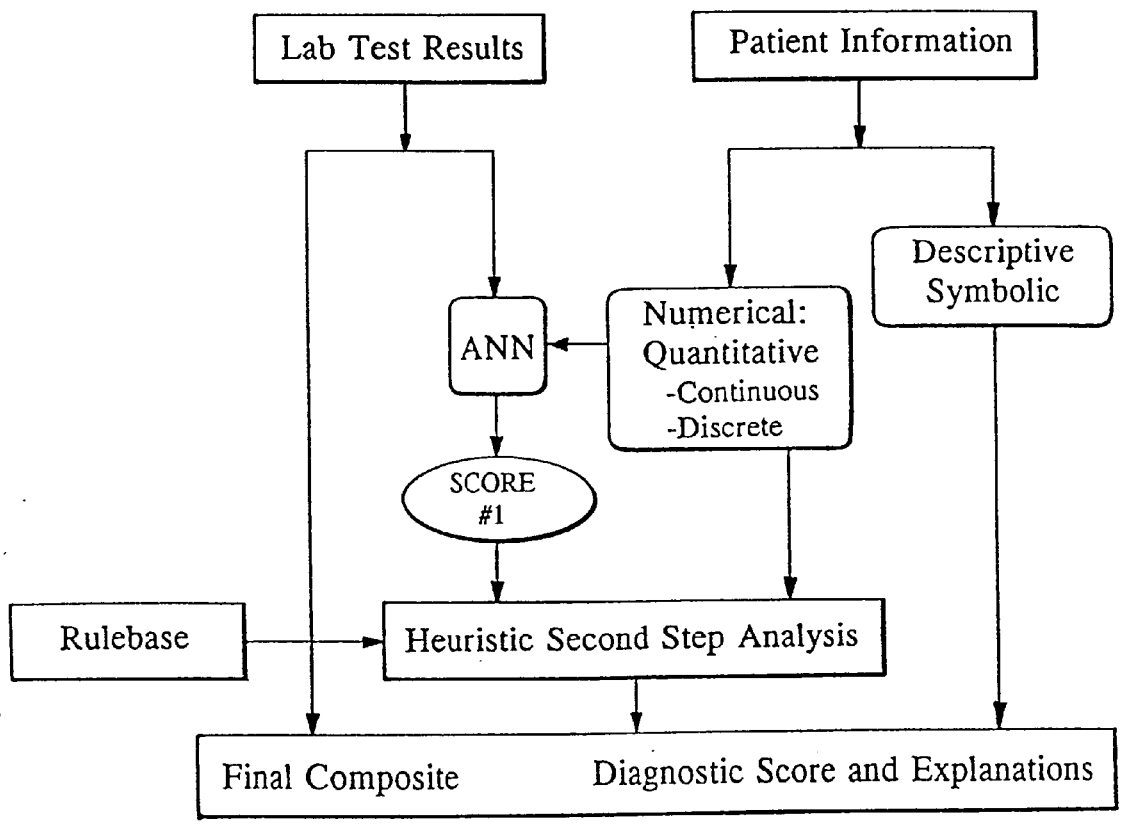
FIG. 4 is a schematic illustration of the second preferred embodiment of the present invention.

As illustrated by FIG. 4, in a second embodiment of the present invention, the diagnostic value obtained by analysis of the biomarkers by a trained neural network is further analyzed by a set of heuristic rules in combination with additional patient information. The additional patient information includes things such as family medical history and demographic information. This data is then processed to yield a second single diagnostic value. In another embodiment, the simultaneous, multi-access reasoning technology system of the present invention utilizes both existing knowledge and implicit information that can only be numerically extracted from training data. Use of existing knowledge may be in the form of setting normal reference ranges of biomarkers specific to the patient being diagnosed. The system has four major functional blocks as described in FIG. 20:

1. Input Data Preprocessing In this block, the observed data values of individual subjects go through sequences of transformations and combinations. The purpose of this procedure is to convert the raw input data into a form that preserves useful information in the most explicit form while eliminating much of the irrelevant "noisy" data. In addition, secondary input variables may be generated using the original inputs. The transformations, which are often nonlinear in nature, can also help to lessen the stress on the adaptive learning and classification block.

2. Mechanistic (Realistic) Modeling and Simulation: In this block, available knowledge and information about a particular disease process are used to establish mechanistic (realistic) models of some of the normal processes (physiological, anatomical, pharmacological, pathological, molecular biological, genetic, etc.) that are relevant to the origination of measured patient data including categories and variables such as but not limited to the following:

Electrical Diagnostic Methods
 EEG
 EKG
 EMG
 Tomographs
 Nerve Conduction Tests
Imaging Diagnostic Methods
 X-ray
 NMR
 CT Scan
 PET Scan
 Fluorography
 Mammography
 Sonography
 Infrared
 Echocardiograms
Clinical Laboratory Diagnostic Methods for Determination of Biomarkers in Various Biological Fluids
 Blood
 Urine
 Saliva
 Gastrointestinal fluids
 Reproductive fluids
 Cerebrospinal fluid
 PCR
 Gene Markers
 Radioimmunoassay, ELISA
 Chromatography
 Receptor assays
Histologic Diagnostic Methods
 Tissue analysis
 Cytology
 Tissue typing
 Immunocytochemistry
 Histopathological Analysis
 Electron Microscopy
 In situ hybridization
Pharmacokinetic Diagnostic Methods
 Therapeutic Drug Monitoring
 Receptor characterization and measurement
Miscellaneous Factors
 Physical exam
 Medical history
 Psychiatric and psychological history
 Behavioral patterns
 Behavioral testing
 Demographic data
 Patterns of drug, alcohol, tobacco, and food intake
 Environmental influences (employment, exposure to chemicals, radiation, toxins, etc.)
 Gross pathology Such models are based on input data with the individual patient under consideration, or information of a class of patents to which the individual patient belongs. The simulation output of these models forms the basis for comparison with the observed patient data and the detection of difference and abnormality in the next functional block.

3. Detection of Differences and Abnormalities: One of the key concepts in this simultaneous multi access reasoning technology system is the utilization of existing knowledge (i.e. CADRS and above diagnostic methods) and facts of normal and disease processes to avoid overloading the numerically oriented adaptive pattern classification subsystem with normal variations in observed data due to differences in patient conditions. In this block, the output results of the mechanistic models are compared with the observed patient data. The differences (not necessarily the simple numerical differences in values) are then fed as input into the adaptive pattern classification subsystem to produce the desired clinical indicators.

4. Adaptive Pattern Classification Subsystem: The classification functions/algorithms in this block, due to the complex nature of clinical problems, are often non-linear in nature which include linear or stepwise linear systems as special cases. The construction of the classification functions and the determination of their parameters are based on known properties of the classification problem and most importantly, the implicit information contained in the available training data. Examples of such adaptive classification systems include various forms of artificial neural networks which classify information.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

In some of the following examples which utilize a neural network in the analysis of the data, a Neural Shell 2, Release 1.5 (Ward Systems Group, Inc.) neural network development program was used for the training of the neural network -on a Pentium 60 mhz computer (Magitronic, Inc.). In other Examples, different computer hardware is used.

EXAMPLE 1

The following example describes the training of a neural network to prognose prostate cancer.

A total of 52 samples were divided into 2 groups, a training set and a generalization testing set. The training set contained 40 samples (28 stable and 12 progressing) and the generalization testing set contained 12 samples (9 stable and 3 progressing).

The initial network architecture was selected based on the level of complexity of the classification task. A multi-layer feedforward network was used. Selection of the initial architecture involved the selection of the number of hidden layers and the number of neurons in each hidden layer. Several trial iterations were performed to determine an adequate configuration that showed good results on both the training sample set and the generalization test sample set. The present network had one hidden layer, having nine neurons, and two output neurons.

Initially, connection weights among the neurons were randomly set. The neural network had five input neurons, corresponding to five input variables significant for prostate cancer: TPS, PSA, PAP, CEA, and testosterone. The training data are shown in FIG. 5. During training, the five input variables for each patient were first linearly scaled into the continuous range between 0.0 and 1.0. The resultant five numbers were then presented as an input vector to the input neurons of the artificial neural network.

For each of the input vectors, the network generated an output based on the connection weights among the network neurons. The output can be a single value or a vector of numbers, depending on the number of output neurons used. The network used had two output neurons. The outputs of the two neurons were processed by the following mathematical equation to yield a single diagnostic index:

$$Index = \frac{(ANN2-ANN1)}{2} + 0.5$$

Each neuron in the network participated in the output calculation by passing the sum of all inputs to the neuron through a non-linear s-shaped function (often a logistic function) and sending the result to each and every one of the neurons in the following adjacent layer. The generated output or each output neuron was compared to the desired "target" output. A value of 0.1 corresponded to a diagnosis of stable and an output of 0.9 corresponded to a diagnosis of progressing. The difference was used to calculate an error term to guide the training algorithm, i.e., the back propagation algorithm, in the adjustment of network connection weights in an attempt to reduce the differences between network outputs and target values over the training sample set.

After training, the neural network correctly classified 100% of the samples.

When presented with the generalization test results, the trained neural network correctly identified 100% of the stable samples and 66% of the samples where the disease was progressing.

EXAMPLE 2

The mathematical description of the ProstAsure™ Algorithm is provided in FIG. 25 which is attached hereto. The training data and test data for ProstAsure™ are provided in FIGS. 6 and 7, respectively. The training data set shows patient data for age, PSA, PAP, CK-BB, CK-MB, CK-MM, total CK, digital rectal examination, and ethnic group.

The ProstAsure™ system displayed the following sensitivities and specificities (expressed as a percentage) for cancer detection in the test data and training data:

| Sensitivity for Detecting | Test | Training |
| --- | --- | --- |
| Prostate Cancer (PC) | 80.3% | 84.4% |
| Stage 2 PC | 85.3 | 85.1 |
| Stages T2, T3 and TN × M1(PC) | 87.9 | 87.9 |
| For detecting BPH as BPH | 66.1 | 68.9 |
| Specificity for Identifying | Percent | |
| Non-Cancer as Non-Cancer | 92.8% | 91.8 |
| Presumed Normal as Normal | 67.6 | 69.2 |

*BPH = Benign prostatic hyperplasia

These results of the ProstAsure™ system were highly statistically significant when analyzed with a Pearson Chi-Square test. Chi-Square value=128.8, with 4 degrees of freedom and a p value <0.00001. These results demonstrate the sensitivity and specificity of the ProstAsure™ system to diagnose prostate cancer, to distinguish stages of the disease, and to recognize benign prostatic hyperplasia and normals as such.

EXAMPLE 3

This example illustrates the construction and training of a neural network for diagnosis of osteoporosis. The training and test data are shown in FIGS. 8 and 9 respectively. The mathematical description of the QuiOs™ algorithm is attached hereto as FIG. 26. This example illustrates the construction and training of a neural network for diagnosis of osteoporosis.

FIG. 8 provides the data used to train the neural network to diagnose osteoporosis. The biomarkers selected included age, calcium, phosphate, estradiol (ETWO), progesterone, total alkaline phosphatase, total intestinal alkaline phosphatase, and % liver alkaline phosphatase. FIG. 8 further includes the diagnostic index obtained by the neural network.

FIG. 9 provides the data use to test the network trained with the data in FIG. 9, and the neural network diagnostic index obtained.

In practicing one aspect of the present invention, the severity of disease in a set of humans or animals with varying severity of disease is measured by a standard method or methods. The measurement is then assigned a numerical value corresponding to a severity scale. The scale ranges from humans or animals with no disease, to humans or animals with severe disease. The scale is preferably a numerical scale. For example, one could assign a value which corresponds to normal or slight disease, another value which corresponds to moderate disease and a third value which corresponds to severe disease.

The concentration of a predetermined set of blood constituents in the set of humans or animals with varying severity of disease is then determined. According to the present invention, it is preferable to measure the blood constituents in the same set of humans or animals in which the severity of disease was measured by the conventional method or methods.

Osteopenia

An example of practicing one embodiment of the present invention is a method for diagnosing osteopenia in a patient. The method preferably utilizes six blood constituents. These constituents are calcium, phosphate, total alkaline phosphatase, an alkaline phosphatase isoenzyme, estradiol, and progesterone. The alkaline phosphatase isoenzymes preferred for practicing the present invention include lymphocyte-derived alkaline phosphatase isoenzyme and bone, liver or intestinal alkaline phosphatase isoenzymes. The present invention includes calculating a bone density quotient using the aforementioned six blood constituents by entering the values for the tests into an QuiOs™ algorithm which is attached hereto as FIG. 26. Age, weight and height are also included in the QuiOs™ algorithm.

In addition to diagnosing the osteopenic state of the patient, an indication of the underlying cause of the osteopenia can be determined using the present invention. For example, by practicing the present invention as described herein, one can determine whether the osteopenia in a patient is caused by post-menopausal lack of estrogen or is caused by some other condition, such as cancer. This allows the attending physician to be better able to prescribe the appropriate treatment for the osteopenia.

Figure 11:
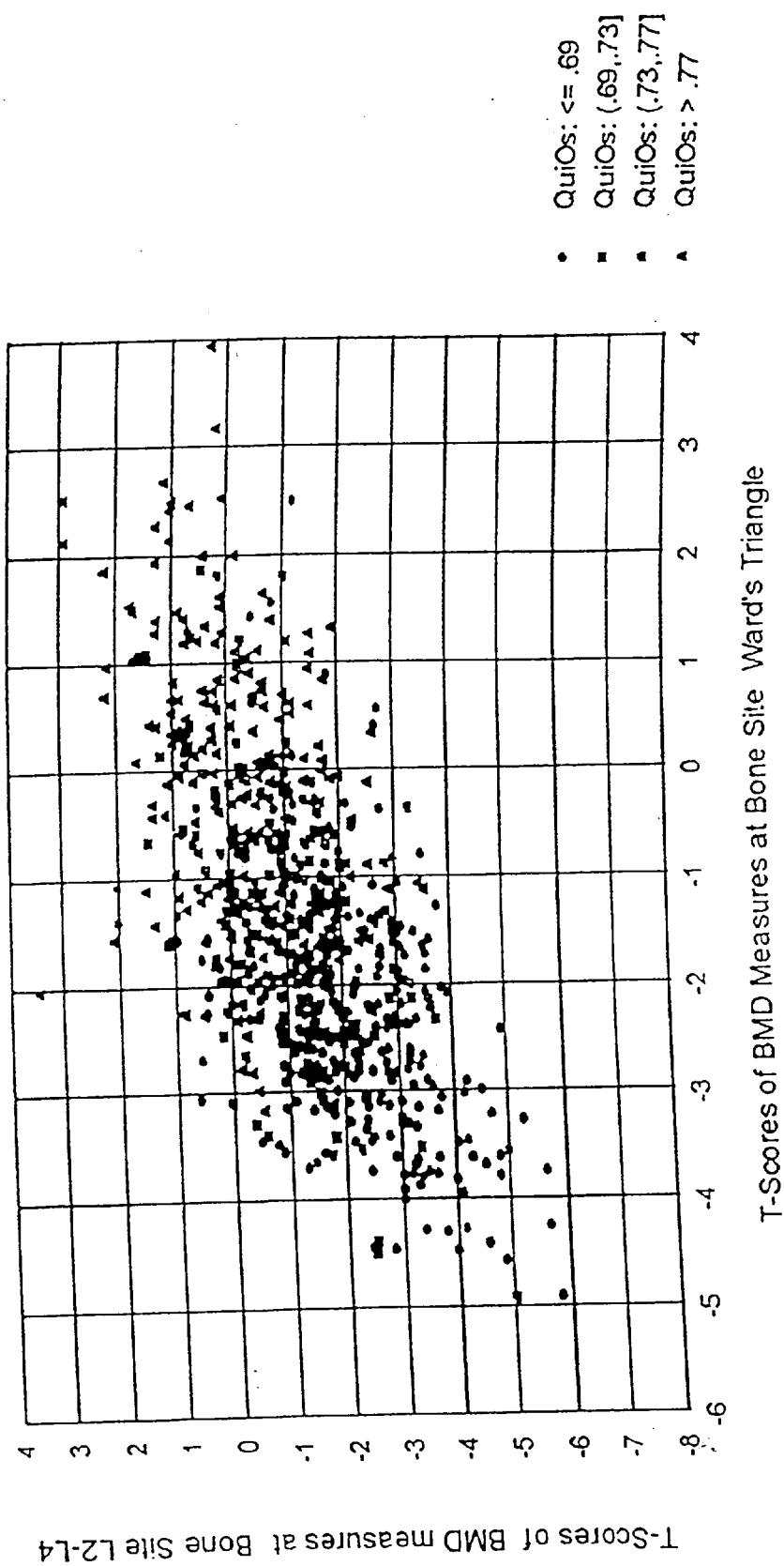
FIG. 11 is a scatterplot of 726 test samples showing that QuiOs™ values correlate with bone mineral density (BMD) measurements at L2–L4 and Ward's triangle in the form of T-scores.
Figure 12:
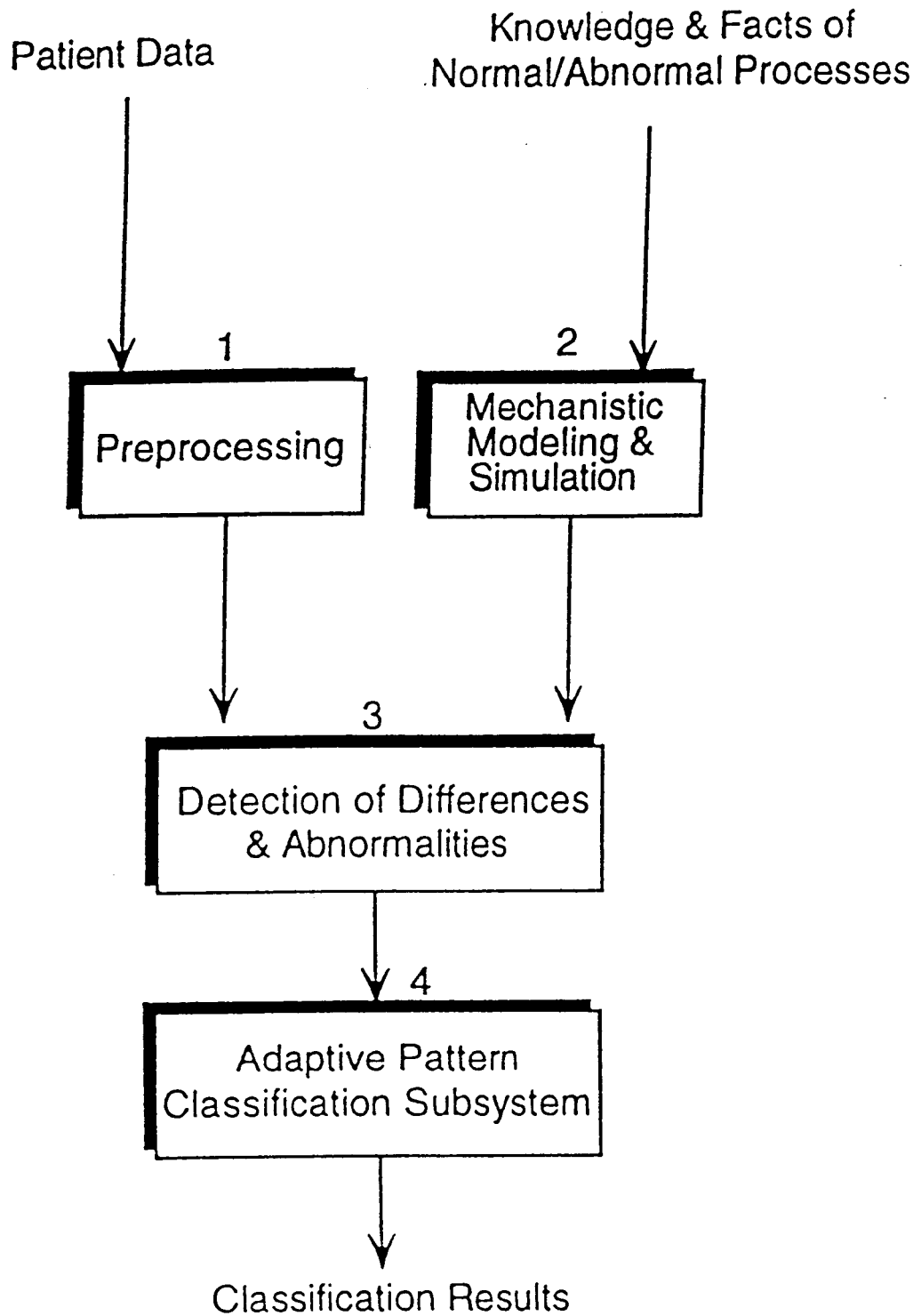
FIG. 12 is a schematic representation of the simultaneous multi access reasoning technology.

Five of the serum tests that are used in the present invention are tests that are commonly performed by clinical laboratories. The test for t-lymphocyte derived alkaline phosphatase is experimental only; however, the test for blood, liver and intestinal alkaline phosphatase isoenzymes are also known. The type of test used to determine the six serum constituents is not critical to the present invention as long as the tests give accurate blood concentrations of the constituents being measured. The results are shown in FIGS. 10 and 11 and show excellent sensitivity and specificity in the diagnosis of osteopenia.

EXAMPLE 4

Figure 13A:
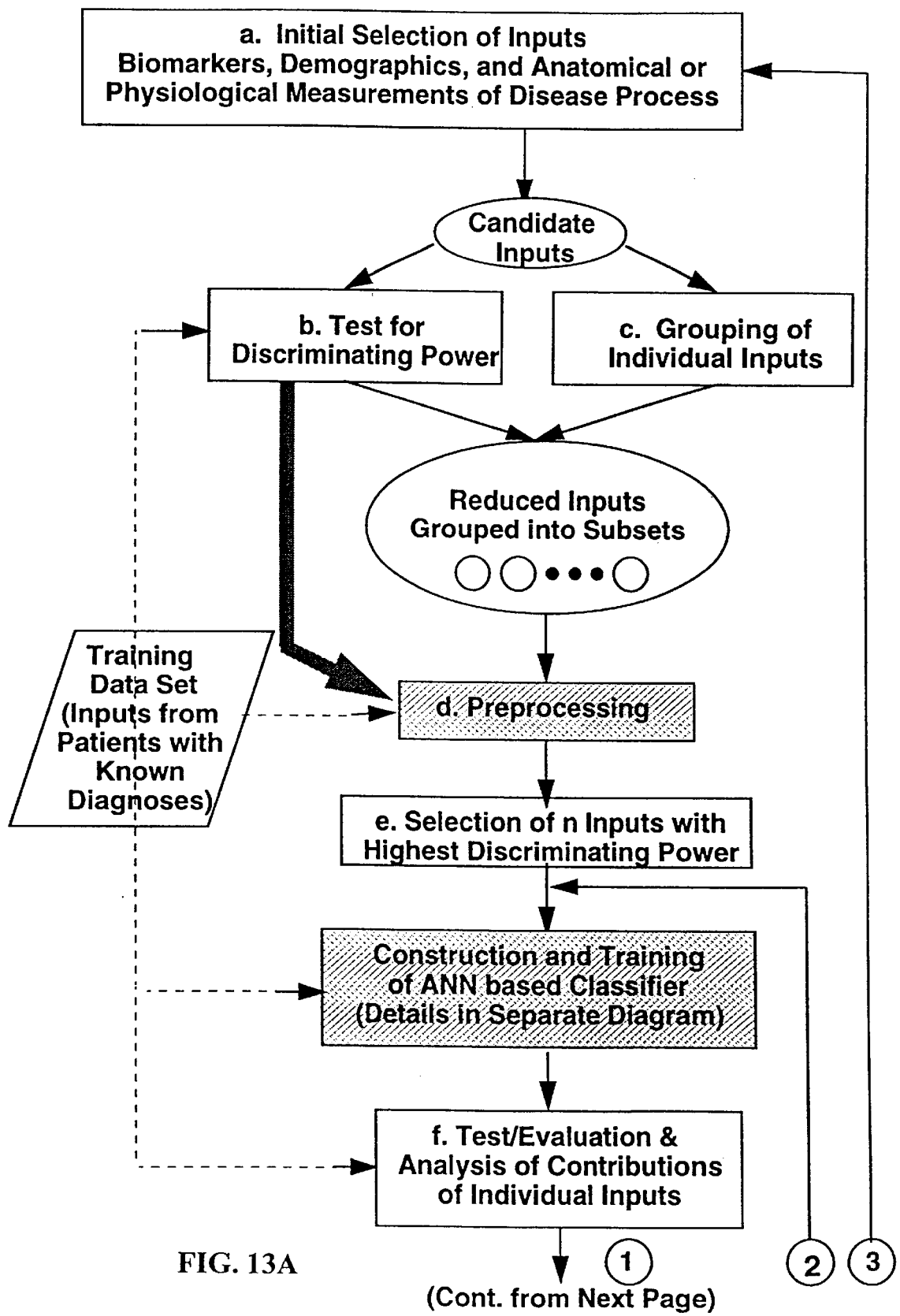
FIGS. 13A and 13B provides an schematic representation of an approach for the construction and training of a computer-based neural network based classifier for the diagnosis and prognosis of disease.
Figure 13B:
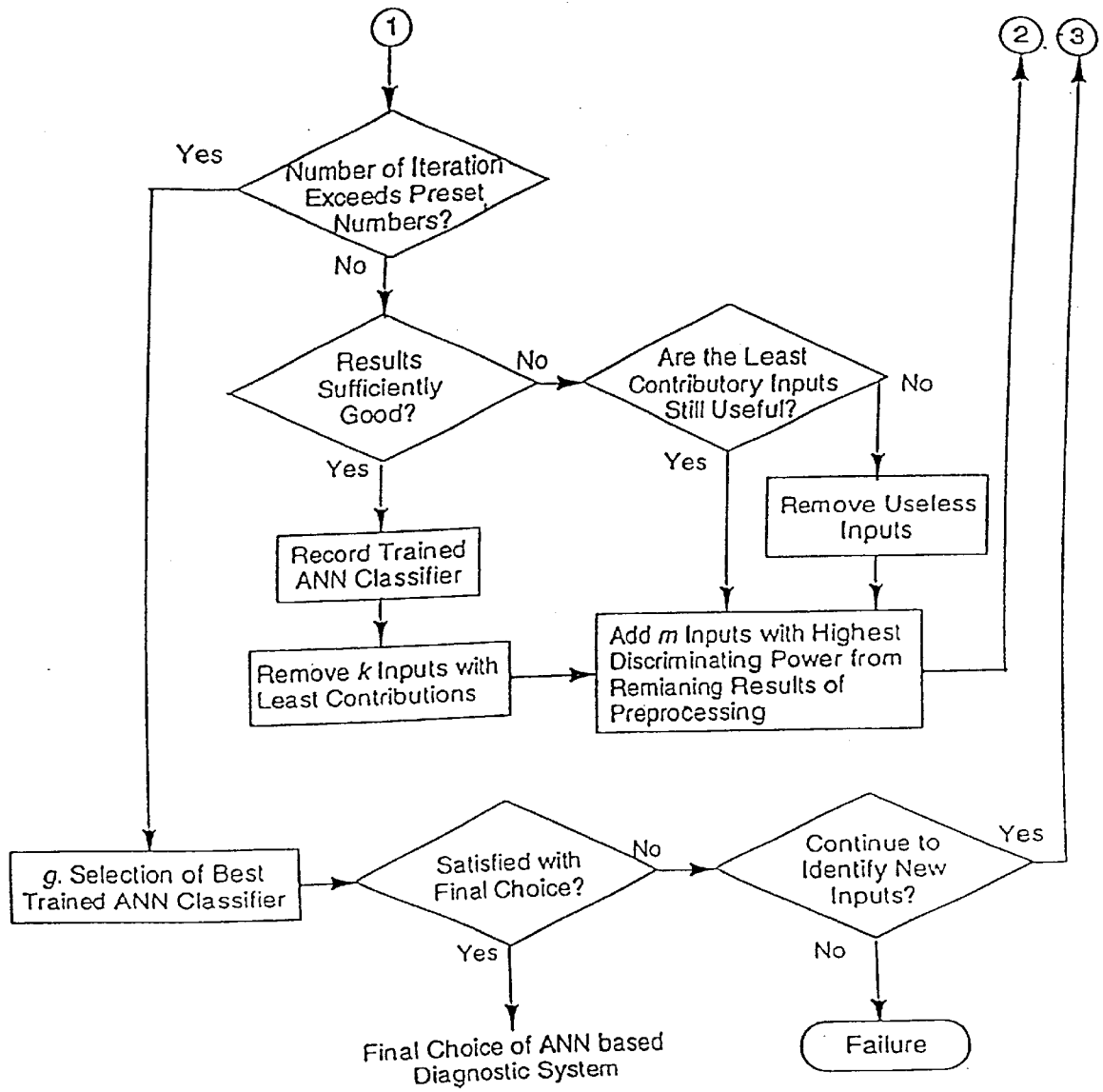

This example provides an explanation of an approach for the construction and training of a computer-based neural network based classifier for the computer assisted diagnosis and prognosis of disease. The lettered subsection headings refer to the lettered labels in FIG. 13.

a. Initial Selection of Inputs Biomarkers and other measures (anatomical, physiological, pathological, etc.) that are relevant to the disease process are selected in such a way that useful information may be extracted for the diagnosis of the disease and the stage of progression of the disease. The selection relies heavily on medical expertise, on current knowledge in biomedical basic science and on advances in clinical research.

b. Test for Discriminating Power A statistical analysis of discriminating power of the selected inputs, individually, and in linear and nonlinear combinations is performed using test data from the training set. The types of software used include commercial statistical packages (e.g. MatLab™ by The Math Works, Inc., Statistira For Windows release 4.5 by StatSoft, Inc.) and programs developed by Horus staff for clustering analysis with nonlinear combination and transformation of input values. Scientific data visualization techniques are used to guide the construction of nonlinear combination and transformation. Inputs that fail to show any discriminating power in separating patient data-points of different diagnostic groups in the training data are removed from the pool of selected inputs.

c. Grouping of Individual Inputs Several of the initially identified inputs may be closely related or simply different measures of the same aspects of the disease process and offer similar yet slightly different values. They are grouped together into subsets of inputs. During the development of neural network based classifiers (which provide a classification system implemented with neural networks), inputs from each subset are used one at a time (ones with higher discriminating power first) to form the list of actual inputs to the classifiers. Biomedical expert knowledge is used in the grouping procedure. For example, two slightly different tests measuring the same biological phenomenon such as CA125 and CA125II might be grouped together. Statistical analyses of interaction, association and agreement between inputs help to identify such groups (e.g., Chi-Square, paired-t test, etc.).

d. Preprocessing The preprocessing step includes preparation of input values, preprocessed values to be used as actual inputs to neural network based classifiers. This step includes linear or non-linear transformation (e.g. re-scaling) of original input biomarker or demographic values which may be digitized values and/or the creation of secondary inputs using linear or non-linear combination of original input values. Software and procedures used in this step are similar to that in step b, "Testing for discriminating power", described above. In step b, the goal is to determine whether or not a particular biomarker or other measurement provides any useful information. In this step d, however, the purpose is to find a set of inputs to the neural network based classifier that in addition to having sufficient discriminating information, should also provide such information in a way that alleviates the burden of neural network training. In this step, statistical, mathematical, and computational tools are used to help "pre-digest" the information. For example, two inputs combined in a non-linear formula provides more explicit information for classification. Add an input that is the computed value using this formula makes the training easier. Expert knowledge in both biomedical and clinical science field (e.g. whether certain types of transformation or combination is biologically "plausible") and experience in pattern classification are used. For example, by viewing samples in the input variable space, one may be able to estimate the complexity in sample distribution and use this information to adjust the neural network structure. Due to the nature of nonlinear operation and the often large number of inputs used in combination, direct numerical evaluation of the effectiveness of the newly created secondary inputs may be very difficult. Scientific data visualization is extensively used to provide guidance in the construction and the evaluation of secondary inputs. For example, color coding and coordination system transformation allows the viewing of data in higher than 3-dimensional space. This helps to understand the distribution of samples in the input variable space and the construction of preprocessing steps.

This preprocessing step is very important. Previous workers in this area assumed that the non-linear nature of the neural network would be able to fully utilize information in the training data in the form of the original input values. (see Astion, M. L. and Wilding, P., "Application of Neural Networks to the Interpretation of Laboratory Data in Cancer Diagnosis", Clinical Chemistry 38: 34–38 (1992) in which there is no mention of preprocessing). However, this step of "untangling" of multi-threaded and inter-related information to facilitate the training of the neural network plays a vital role in the success of developing neural network based diagnostic systems.

- e. Selection of Inputs with Highest Discriminating Power
  This step involves the selection of input values from original input values, which are possibly transformed, and from newly created secondary inputs, to form a list of actual inputs to the neural network based classifier. The initial number of selected inputs in the list is based on the results from discriminating power estimation in steps b and d and the available knowledge of the complexity of the problem.
- f. Test/Evaluation and Analysis of Contributions of Individual Inputs In this step, the performances of the trained neural network based classifiers are evaluated with data from the test data set that have not been involved in the construction and training of the neural network based classifier which is a classification system that uses neural networks as its classification decision making component. Because of the nonlinear nature in neural network based computation, direct analysis of contribution of individual inputs in producing the final output of an neural network classifier is often not possible. The following steps are used: 1) inspection of network connection strength initiated from each input; 2) sensitivity analysis that compares the relative change in neural network output with changes in single input values; and 3) more complete analytical methods such as using Monte Carlo sampling methods to construct a sensitivity surface with respect to simultaneous changes in multiple inputs.
- g. Selection of Best Trained Neural Network Classifier
  The iterative process of adding/deleting input values and construction/evaluation of neural network classifiers produces multiple configurations of neural network based diagnostic systems. The selection of "best" are based on the two primary considerations: 1) the effectiveness of the system in both absolute terms and in comparison with existing methods; and 2) the number of inputs and the cost associated with them.

EXAMPLE 5

Figure 14:
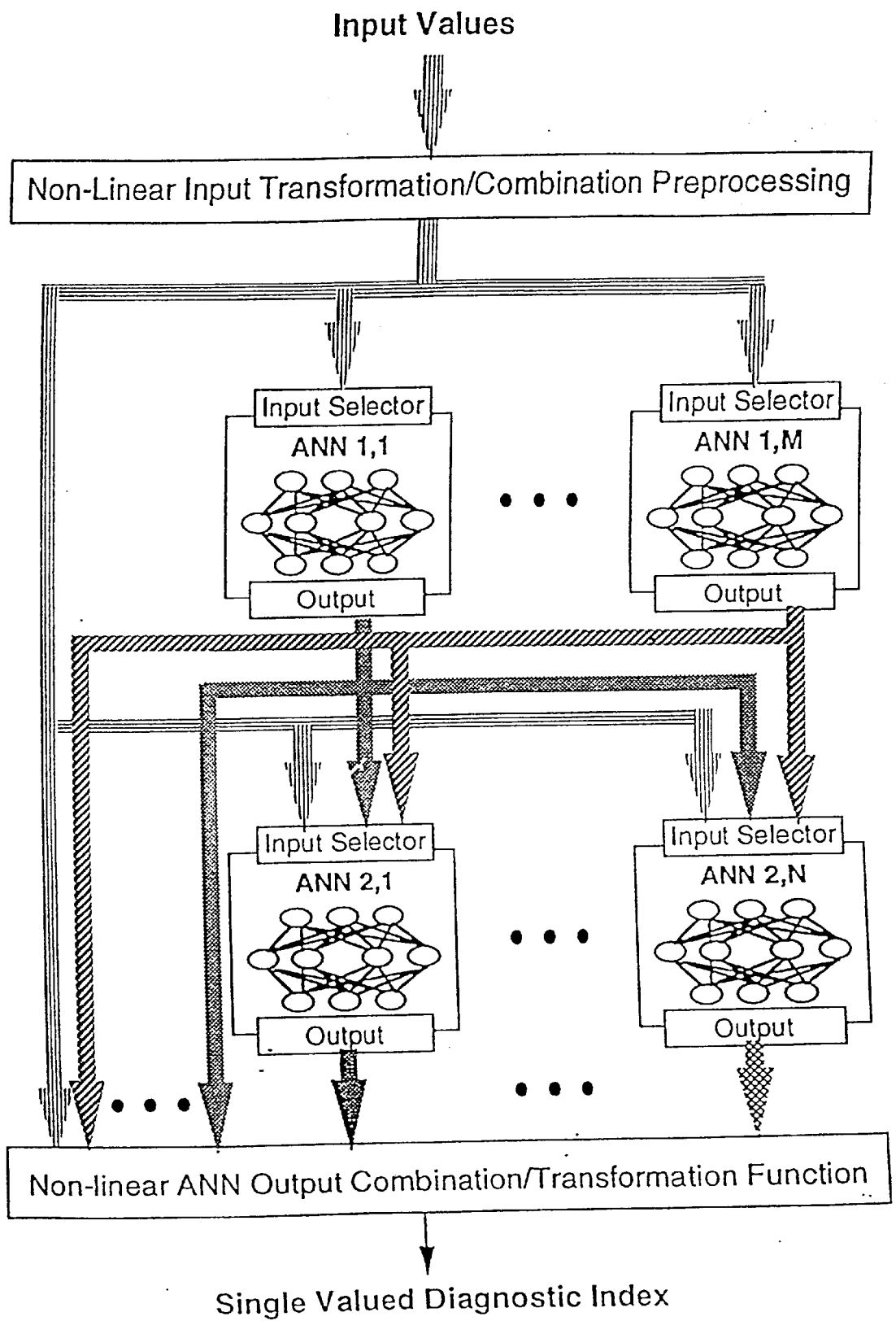
FIG. 14 shows a configuration of a neural network based diagnostic system.

Procedure for Construction and Training of Neural Network Based Classifier for Computer Assisted Diagnostic Apparatus The following list describes the steps used in the construction and training process as shown in FIG. 14.

1. If the total number of diagnostic groups equals 2, go to next step. Otherwise, based on known facts about the disease process, organize the separation of groups into a binary classification decision tree. For each pair of groups that requires a binary classification (yes/no, positive/negative, etc.) repeat steps 2–6.
2. Develop neural networks in the first level. (ANN 1,1 through ANN 1,M)
   a. Select an appropriate data set for training and testing.
   b. If the total number of recorded neural networks exceeds a preset number, go to step 3.
   c. Configure a new neural network and select a subset from the total input list (done by setting the neural network input selector).
   d. Train multiple neural networks of the same configuration with various initial conditions and training parameters. For each trained neural network, if the results overlap significantly with a previously trained neural network including networks with different network configurations (in terms of patients in each group being classified correctly or incorrectly), discard the one that has the inferior performance. Repeat until no significant performance improvement is observed in newly trained neural networks or all reasonable variations of initial conditions and parameters have been exhausted.
   e. If all reasonable network configurations and their variations have been exhausted, go to next step, otherwise go to step 3.
3. Compare performance of all recorded neural networks and purge those with poor or duplicated performance. If two neural networks offer similar results, delete the one with more complicated network structure.
4. Record all remaining neural networks.
5. Develop neural networks in the second level (neural networks (ANNs) 2,1 through ANN 2,N). Augment the original list of inputs with output values from remaining neural networks in the first level and repeat steps 2–4.
6. Combine output from one or several recorded neural networks into a single classification index using linear or nonlinear methods. Evaluate its performance in separating the two diagnostic groups using test data not involved in network training. Select the best binary classification function for the pair of diagnostic group.
7. Combine the obtained binary classification functions according to the binary classification decision tree to form a "super function" that produces a single valued diagnostic index with the Horus arbitrary unit and reference ranges for each of the different diagnostic groups.

EXAMPLE 6

Figure 15:
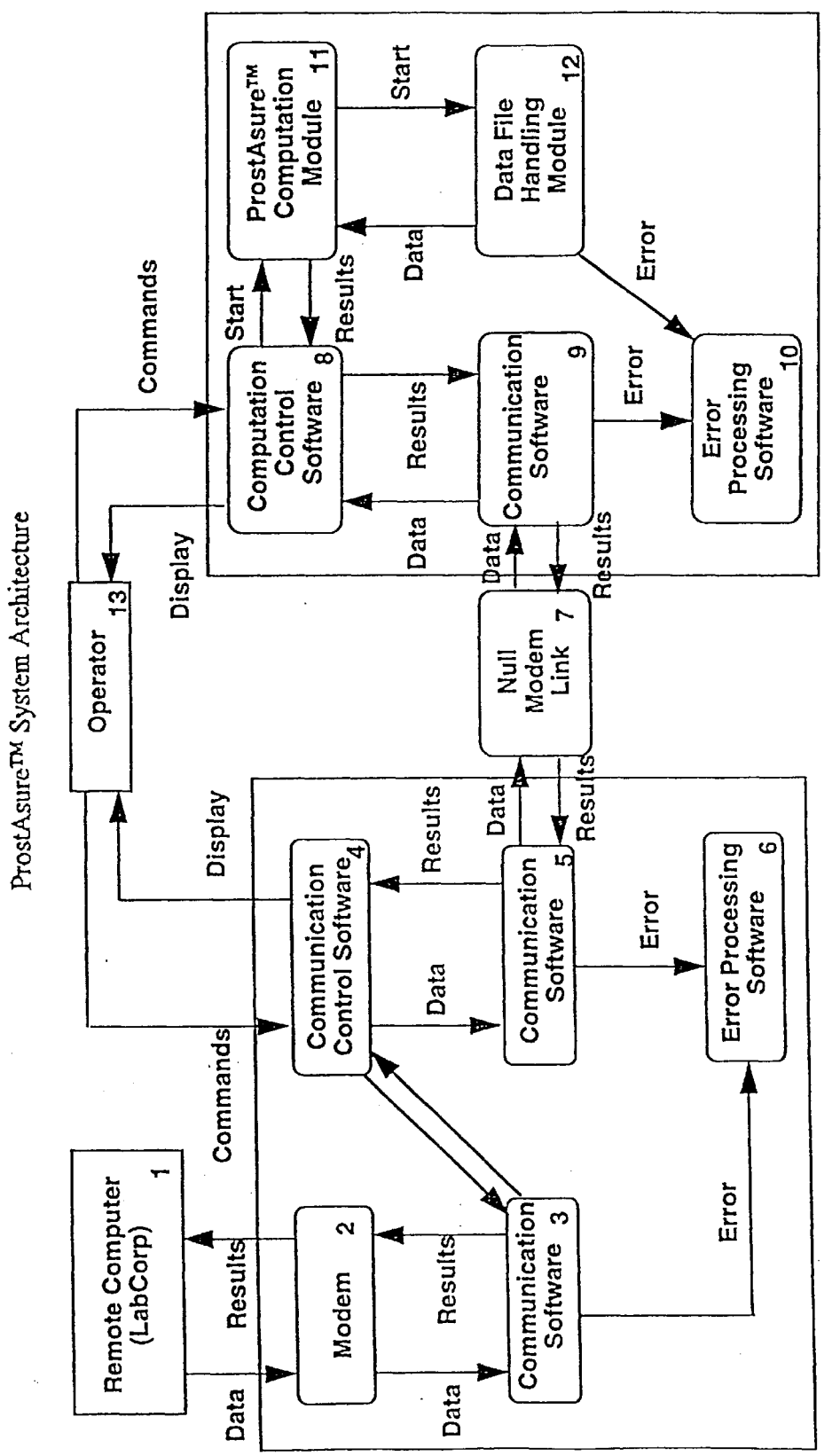
FIG. 15 is a schematic overview of the ProstAsure™ computer-based neural network system architecture for receiving patient data, analyzing the patient data with a trained neural network and transmitting results.

ProstAsure™ Computer-Based System for Neural Network Analysis of Patient Data for Diagnosis of Prostate Cancer This is a computer-based system which provides the capability to receive patient data, analyze the data with a trained neural network, produce an output value indicative of the presence or absence of prostate cancer, transmit the value to another computer, and transmit the value to another location. The system is schematically illustrated in FIG. 15. The individual boxes in FIG. 15 are numbered and referred to in the following description. This system provides high capacity to receive and analyze a large volume of patient data, to rapidly produce output values to diagnose prostate cancer and to optionally transmit these results to remote locations. This system permits the rapid analysis of numerous sets of patient data and provides diagnostic values to the clinical laboratory and to the health care provider. It is to be understood that FIG. 15 represents a preferred embodiment of the present invention and that other system configurations, such as different hardware configurations involving a single computer or multiple computers may be employed in the practice of this invention for the diagnosis of any disease including prostate cancer.

The data files contain data from patient tests that are required for the computation of the diagnostic index for prostate cancer. The data file is a standard ASCII file. Each patient record consists of one line in the file. Lines in the file are delimited with carriage return; line feed (CR/LF) pairs. The fields in a record are delimited with an ASCII character ',', and each record contains the following seven fields: 1) identification (ID)—alphanumeric; 2) Age—numeric; 3) prostate specific antigen (PSA)—numeric; 4) PAP—numeric; 5) CKBB—numeric; 6) CKMB—numeric; 7) CKMM—numeric. Each alphanumeric field contains a string of characters consisting of letters 'a' through 'z', 'A' through 'Z', digits '0' through '9', and the characters '_', '-', '.', '$'. A numeric field contains a string representation of a decimal number. It may contain a single decimal point '.'. The space character ' ' and comma character ',' are not allowed within a number.

Each patient record occupies a single line in the input data file. Data fields in a record are separated by commas. In the result file to be returned to LabCorp, the input values are repeated and then followed by two additional data fields also separated by commas: the computed ProstAsure™ (HORUS Therapeutics, Rochester, N.Y.) value, and an integer valued error code.

Figure 16:
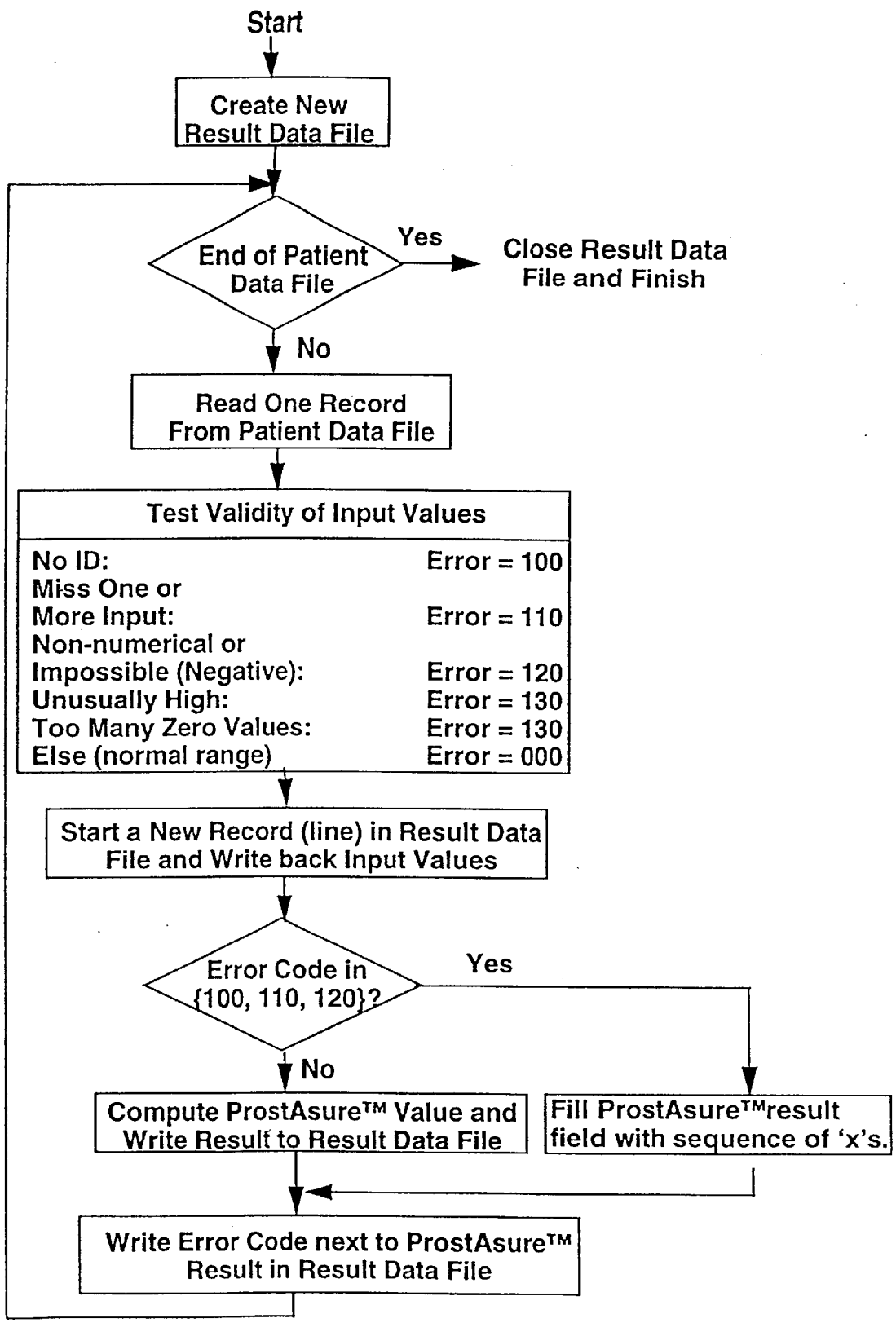
FIG. 16 is the system architecture for analyzing patient data input and computation of ProstAsure™ diagnostic values.
Figure 21:
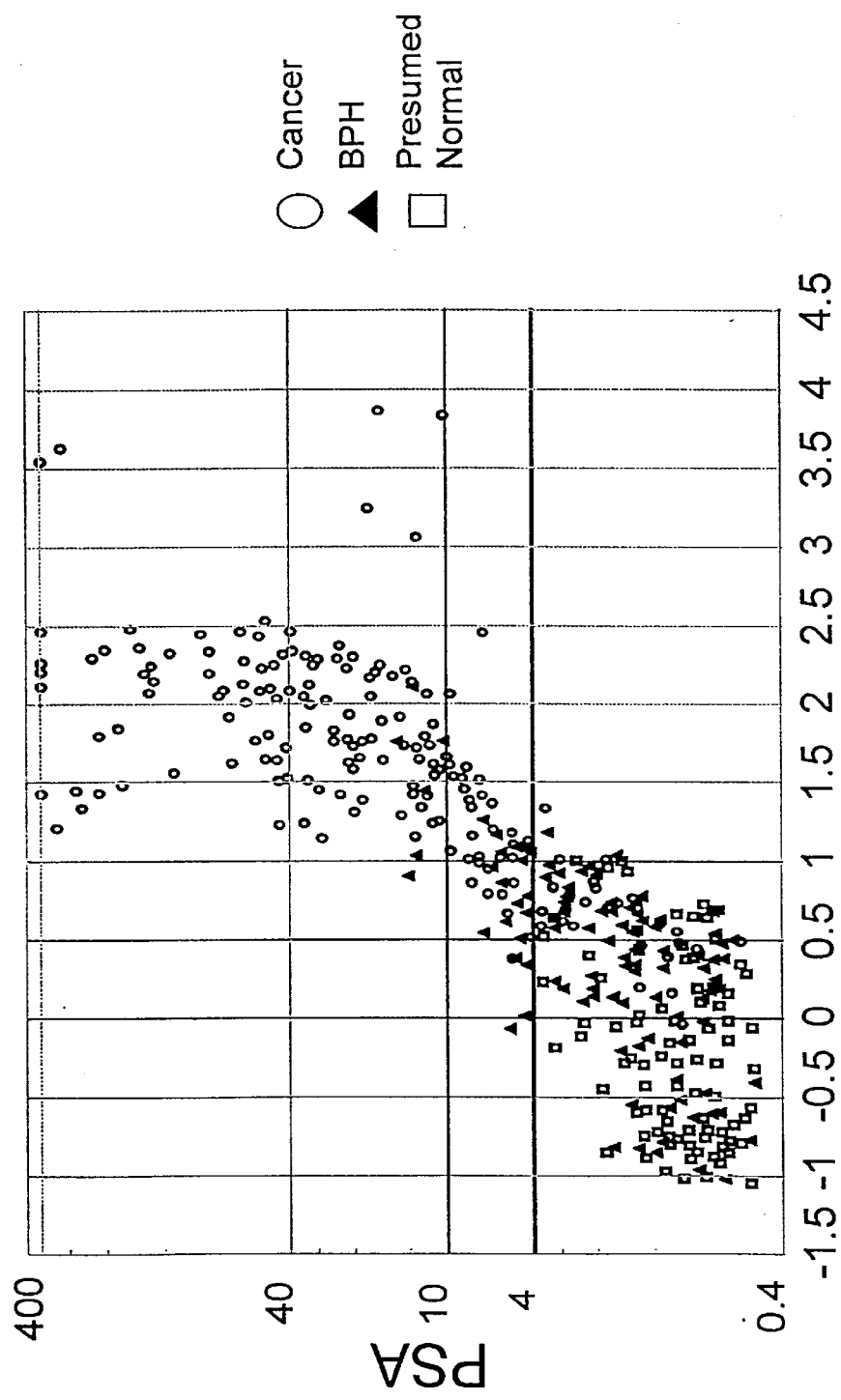
FIG. 21 is a scatterplot of ProstAsure™ values vs. PSA values in 416 test samples. By non-linearly combining multiple biomarkers ProstAsure™ effectively separates normal, BPH and cancer patients better than using a single biomarker (PSA).
Figure 22:
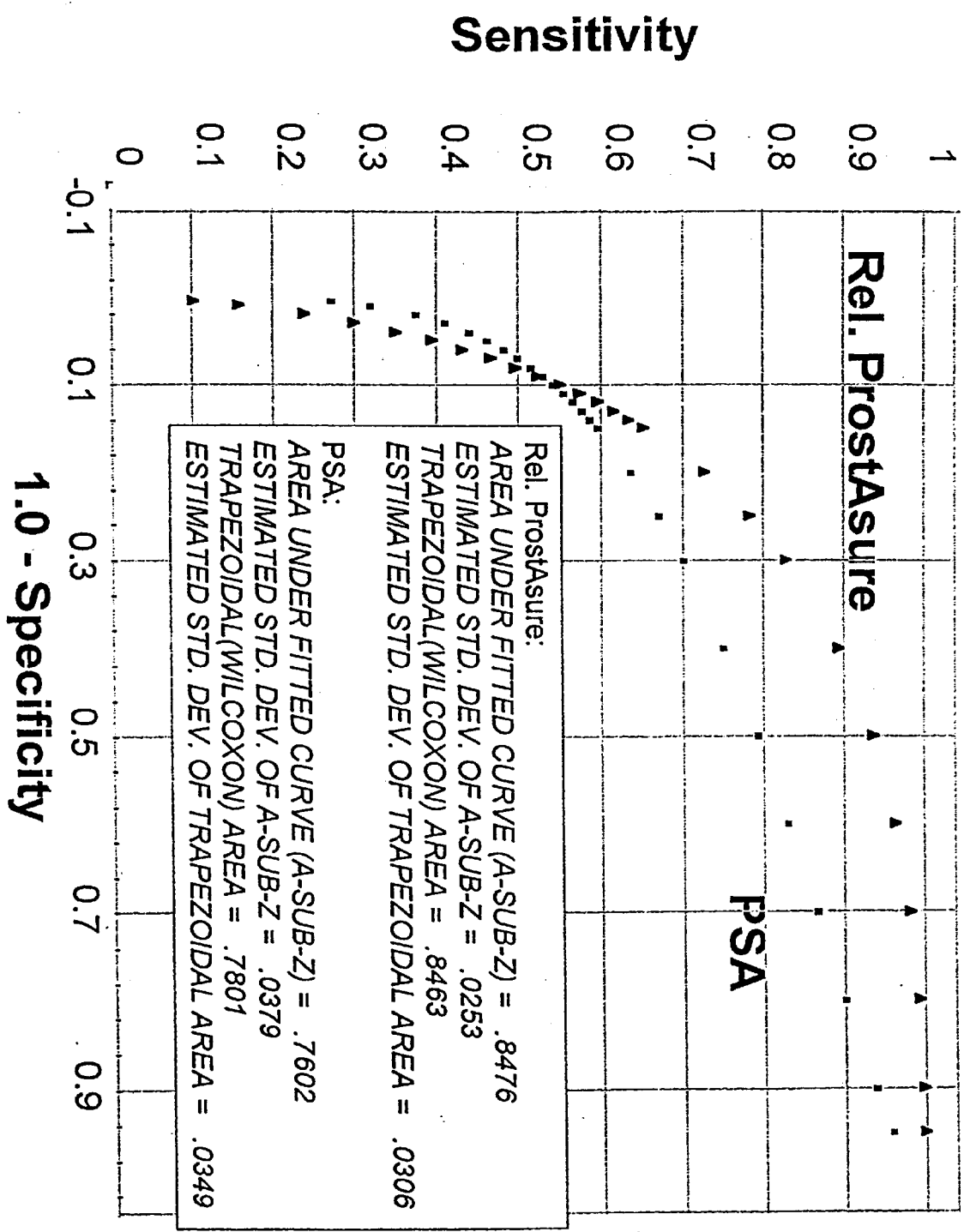
FIG. 22 shows receiver-operating characteristic (ROC) curves comparing the diagnostic power of ProstAsure™ and PSA alone. The area under the curve is a measure of the usefulness of a test. The Rel. ProstAsure™ refers to normalization with age-specific reference ranges. ProstAsure™ significantly outperforms PSA with statistical significance in separating cancer from normal and BPH.
Figure 23:
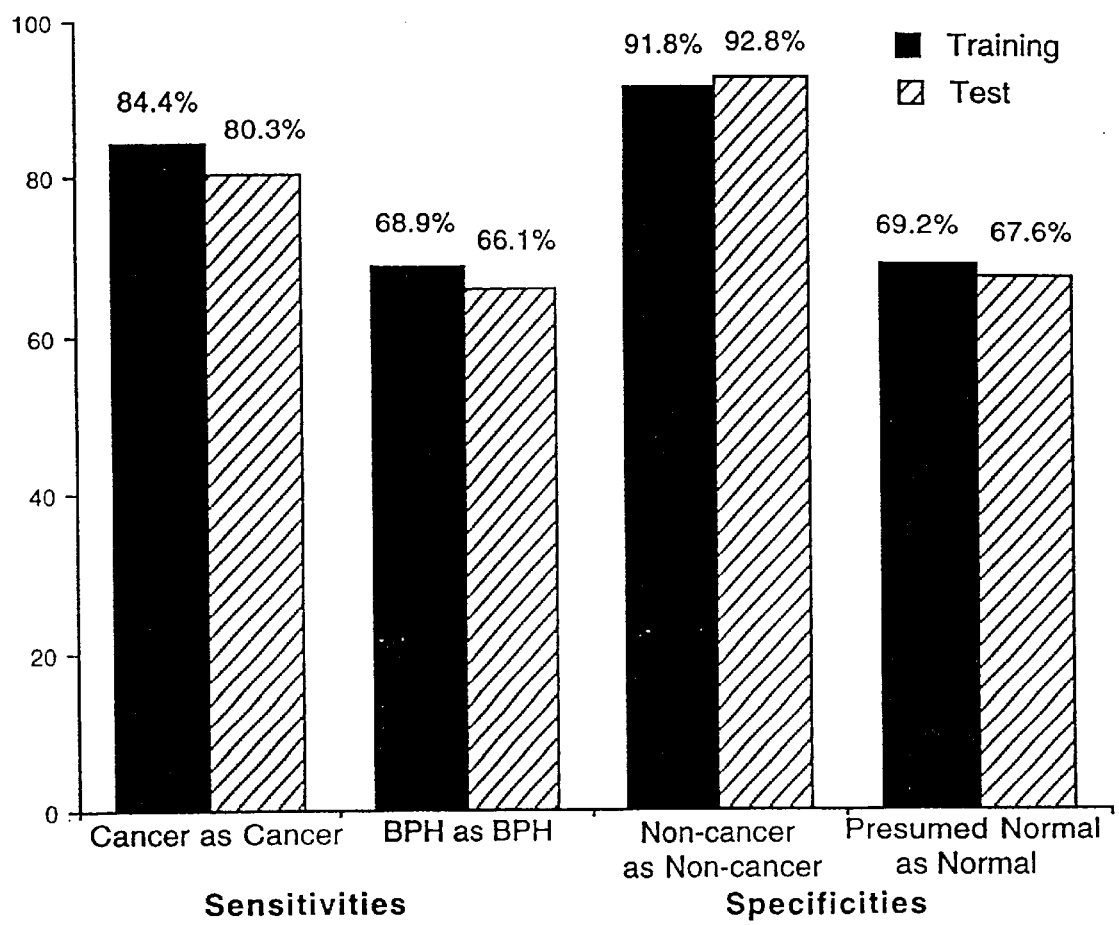
FIG. 23 demonstrates ProstAsure™ sensitivities and specificities computed with training and test data.

Prior to the actual computation of the ProstAsure™ value, a patient record is checked for errors according to the following error detection criteria in the order as they are listed as shown in FIG. 16. Whenever an error other than code 130 happens, error check stops. No ProstAsure™ Value is computed for the patient. The ProstAsure™ field in the output file record is filled with "xxxx" and the first non-130 error code will attach as the last field. When all criteria have been checked and no error or only code 130 has been detected, the ProstAsure™ value is computed and reported in the result file record. The error code 0 or 130 is attached accordingly as the last field.

Error codes are defined as follows:
Error code 110—The record contains fewer than 7 comma separated fields. An empty field followed by a comma is still considered as a field and will not trigger this test.
Error code 100—The first field (ID field) is empty.
Error code 120—One of the remaining data fields is not in a valid numerical format (including an empty field) or one of the data fields has a negative value.
Error code 130—One of the laboratory test values exceeds 5 times the upper bound of the normal patient reference range; or three (3) or more laboratory test results have zero values; or age=0 or age>150.

The ProstAsure™ system consists of two computer workstations and associated communication devices and links (FIG. 15). The following paragraphs provide an overview of the system.

ProstAsure™ Station I (14) is primarily a communication control station. It downloads test data from a remote computer system (LabCorp) (1) via a modem (2) and a telephone line and uploads the ProstAsure™ results back to the remote system. Station I (14) is linked to Station II (15) by a direct null modem cable (7) on their corresponding serial ports. Station I (14) sends successfully downloaded data files to Station II (15) and receives ProstAsure™ result files, from Station II for uploading. Station I controls the timing of download intervals. It processes error conditions (6) by retrying and/or alarming operators (13) depending on the error conditions. Station I compares the data portions of outgoing result files and incoming data files (5) before uploading (4) and (3) to ensure integrity of the result files.

ProstAsure™ Station II (15) is the main computation station for ProstAsure™ algorithm computation (11) and houses the trained neural network (11). Station II (15) receives data files from Station I (14) and sends (8 and 9) results files to Station I (14). Station II (15) reads and verifies the data received from Station I. If invalid data are detected (12 and 10), the ProstAsure™ result field will be marked with "x" characters and a special error code will also reflect the condition. If the data values are detected to be unusual but valid, the ProstAsure™ result will be provided; however, an error code will indicate the condition. Station II invokes a dynamic link library (DLL) from the commercial software package NSHELL2 release 2.0 (Ward Systems Group, Inc., Frederick, Md.) a leading neural network software, to perform the computations of neural network structures. Station II contains error handling procedure (10) to process various error conditions. It alarms (9 and 10) the operators (13) under critical error conditions. Station II is also responsible for archiving the original data files and result files.

The ProstAsure™ system uses Kermit software (Columbia University) for communications between two Stations I and II and between Station I and remote computer systems. Kermit is reliable, well tested communication protocol. The ProstAsure™ system software runs under Microsoft Windows environment, which provides a consistent, friendly user interface. ProstAsure™ software is designed to execute in full screen mode to simplify the operations.

System Description

System Requirements:

A schematic overview of the system is provided in FIG. 15.

Station I 14: Station I requirements include the following: a Pentium computer 75 Mhz or higher, a minimum of 8 Mb RAM, a minimum of 1.0 Gb Hard Drive, an internal modem at speed 9600 bps or higher, a SVGA monitor, and Microsoft Windows for Work group (WFW) 3.11.

Station II 15: Station II requirements include the following: a Pentium 75 Mhz or higher, a minimum of 8 Mb RAM, a minimum of 1.0 Gb Hard Drive, an internal 850 MB tape drive, a super VGA monitor, and Microsoft Windows for Workgroup (WFW) 3.11.

The system requires a laser printer that has Microsoft Windows supported printer driver. Also required is null modem 7 and RS-232 cable for connection between Station I and II via serial ports.

Actually Installed System

An example of an actually installed system is as follows:

Station I is composed of: NEC Ready Pentium Systems ™
    (Pentium 100 MHz CPU, 16 Mb RAM,
  1.0 Gb Hard Drive)
    NEC MultiSync XV17 ™ Monitor;
    preloaded with MS Windows for
  Workgroup 3.11.
Station II is composed of: NEC Ready Pentium Systems ™
    (Pentium 100 MHz CPU, 16 Mb RAM,
  1.0 Gb Hard Drive)
    Internal 850 Mb Tape unit:
    NEC MultiSync XV17 ™ Monitor,
    preloaded with MS Windows for
  Workgroup 3.11.
Printer:    HP LaserJet III
References:  Operations Procedure;
    Ready Pentium Systems User's Guide;
    NEC Ready Pentium Systems Hardware
    Ref./Operations Guide;
    NEC MultiSync XV17 ™ User's Guide.

Functions of the Systems

In the following description of procedures, the term "emergent warning procedure" defines an automated procedure to report an abnormal situation in the computer software or hardware system, or in the data file transferring mechanism that requires the immediate attention or intervention of a human operator and/or the Director of Operation 13. In the "emergent warning procedure", 1) the affected computer produces a loud siren that can be heard throughout the facility; 2) the affected computer screen blinks and displays the error message and the corresponding error code; and 3) the computer system automatically dials the pager number of the officer on duty.

Station I 14 downloads patient test data from and uploads computed results back to the host computer (1) (a HP3000 UNIX based workstation) located at the Laboratory Corporation of America (LabCorp) facility in Research Triangle Park, North Carolina. Station I serves as a buffer and a firewall between the external data source (LabCorp host computer) and the ProstAsure™ processing workstation (Station II) 15. The following are detailed descriptions of functions provided by Station I. These are also the functions tested during system validation.

I-1: Initiating remote connection via modem to the host computer. Invoking the automated login procedure using the MS DOS Kermit software and the downloading procedure to obtain a new patient data file for processing. It uses the Kermit ASCII file transfer protocol.

I-2: Connection and file down loading automatically occurs every 60 minutes. In case of a failed connection, a reconnection automatically repeated in 10 sec. interval. After a continuous sequence of 10 failed such attempts, System I issues error code #200 and starts the "emergent warning procedure".

I-3: Upon completion of data file down loading, System I initiates connection to Station II and sends the newly received data file to Station II. If Station I fails to send data after 10 repeated attempts, it issues error code #230 and starts "emergent warning procedure".

Station II processes the received data, computes ProstAsure™ index for each patient, and sends the results together with the original input values to Station I.

I-4: Upon successful reception of completed result data file, Station I then compares input values of each patient in the result data file with the input values in the originally received data file to ensure a complete match. If any error occurs, the "emergent warning procedure" is invoked and error code #300 or #310 (number of records do not match) or #320 (at least one record has unmatched input values) are displayed. When 300 series errors happen, no results are sent to the LabCorp host computer and the Director of Operations is notified immediately.

I-5: Connecting to LabCorp and sending data back to the LabCorp host computer. (Similar to I-1, except for performing file unloading instead of file downloading).

I-6: Similar to I-2, if the connection attempt fails, Station I repeats connection attempts in 10 seconds intervals. After a continuous sequence of 10 failed such attempts, Station I displays error code #290 and starts "emergent warning procedure".

Station II receives data from and sends data to Station I. Station II processes data using the ProstAsure™ algorithm. The following functions are provided by Station II. These functions are tested during system validation.

II-1: Upon establishing connection initiated by Station I, Station II receives the transmitted patient file.

II-2: Station II sequentially processes patient records in the data file using the ProstAsure™ algorithm. (See FIG. 25)

II-3: Upon completion of Step II-2, Station II initiates connection to Station I and sends the result data file to Station I using the MS DOS Kermit ASCII file transfer protocol. If file sending fails after 10 repeated attempts, Station II issues error code #260 and starts the "emergent warning procedure". A record (line) in the result data file consists of the input data values as used in the computation plus two additional fields, the computed ProstAsure™ value of the patient and a three digit code indicating whether the computation is normal or abnormal. In the abnormal case, the code is an error code which contains information about the type of abnormality that has occurred.

II-4: After completion of sending the result data file to Station I, the data file and the result file which consists of the data file plus two additional field columns: 1) computed values, and 2) error codes, are archived in two designated directories in Station II, "c:\pacompu\padata\" and "c:\pacompu\paresult\" with the file names reflecting encoded date and time tag in the form: mmddhhnn.yy, where mm:month, dd:date, hh:hours, nn:minutes, and yy:year.

EXAMPLE 7

The present invention includes use of a computer-assisted neural network to diagnose ovarian cancer. This new version uses biomarkers listed above under the heading of Ovarian Cancer II and includes CA125, M-CSF, OVX1, LASA, CAA7-24 and CA19-9. When tested with an independent data set of 186 subjects, the test achieves a sensitivity of 89% and a specificity of 89%.

It should be understood, of course, that the foregoing relates only to preferred embodiments of the present invention and that numerous modifications or alterations may be made therein without departing from the spirit and the scope of the invention as set forth in the appended claims.

We claim:

1. A computer based system for screening for a disease, prognosing a disease, diagnosing a disease, determining a presence or an absence or a severity of a disease, or a likelihood of obtaining a disease, comprising:
   a computation station for receiving and processing a patient data file, said computation station comprising a trained neural network for processing said patient data file and producing an output value corresponding to a presence or an absence or a severity of a disease, or a likelihood of obtaining a disease, wherein said trained neural network is trained with a method comprising:
   preprocessing patient biomarkers, comprising:
      selecting patient biomarkers associated with the disease process;
      statistically and/or computationally testing discriminating power of the selected patient biomarkers individually in linear and/or non-linear combination for indicating the presence or the absence or the severity of the disease, or the likelihood of obtaining the disease;
      applying statistical, mathematical, or computational tools, and/or expert knowledge for the derivation of secondary inputs to the neural network that are linear or non-linear combinations of the original or transformed biomarkers;
      selecting only those patient biomarkers or derived secondary inputs that show discriminating power; and
      training the computer-based neural network using the preprocessed patient biomarkers or derived secondary inputs.

2. The computer based system of claim 1, further comprising a communication station in communication with said computation station;
   wherein said communication station transmits said patient data file to said computation station for introduction into said trained neural network;
   wherein said output value from said trained neural network is stored in a result data file; and
   wherein said communication station receives said result data file from said computation station.

3. The computer based system of claim 2, further comprising a remote computer in communication with said communication station;
   wherein said remote computer transmits patient data to said communication station;
   wherein said communication station stores said patient data in said patient data file prior to transmitting said patient data file to said computation station; and
   wherein said communication station transmits said result data file received from said computation station to said remote computer.

4. The computer based system of claim 2, further comprising a first remote computer and a second remote computer in communication with said communication station;
   wherein said first remote computer transmits patient data to said communication station;
   wherein said communication station stores said patient data in said patient data file prior to transmitting said patient data file to said computation station; and
   wherein said communication station transmits said result data file received from said computation station to said second remote computer.

5. The computer based system of claim 1, wherein said patient data comprises patient biomarkers and patient demographic data.

6. The computer based system of claim 1, wherein said trained neural network is trained to determine the likelihood of obtaining a disease, screen for the disease, determine the severity of the disease, or diagnose or prognose the disease, wherein the disease is selected from the group consisting of osteoporosis, osteopenia, breast cancer, ovarian cancer, colon cancer, prostate cancer, and testicular cancer.

7. The computer based system of claim 6, wherein the disease is prostate cancer and the biomarkers are patient age, LASA-P®, PAP, PSA, CK-MB, CK-MM, CK-BB or any combination of the biomarkers.

8. The computer based system of claim 6, wherein the disease is osteoporosis and the biomarkers are patient age, serum calcium, serum phosphate, estradiol, progesterone, ALP, ALP Isoenzyme 1, ALP Isoenzyme 2, or any combination of the biomarkers.

9. The computer based system of claim 6, wherein the disease is ovarian cancer and the biomarkers are patient age, LASA-P®, CA125, CA12511, DM/70K, MCSF, OVX1, CA7-24, CA19-9 or any combination of the biomarkers.

10. The computer based system of claim 6, wherein the disease is breast cancer and the biomarkers are patient age, LASA-P®, CEA, CA15-3®, HER2/neu, or any combination of the biomarkers.

11. The computer based system of claim 6, wherein the disease is testicular cancer and the biomarkers are patient age, LASA-P®, AFP, HCG-Beta, CA15-3® or any combination of the biomarkers.

12. The computer based system of claim 6, wherein the disease is colon cancer and the biomarkers are patient age, LASA-POR, CA19.9, CEA or any combination of the biomarkers.

13. The computer based system of claim 1, wherein said computation station comprises more than one trained neural network.

14. The computer based system of claim 1, further comprising an emergent warning procedure for detecting and reporting an abnormal situation in the computer based system.

15. The computer based system of claim 14, wherein the emergent warning procedure reports the abnormal situation through an audible signal.

16. The computer based system of claim 1, further comprising a second trained neural network; and
   wherein said output value produced by said trained neural network is introduced into said second trained neural network, which produces a second output value corresponding to the presence or the absence or the severity of the disease, or the likelihood of obtaining the disease.

17. The computer based system of claim 16, further comprising a communication station in communication with said computation station;
   wherein said communication station transmits said patient data file to said computation station for introduction into said trained neural network;
   wherein said second output value from said second trained neural network is stored in a result data file; and
   wherein said communication station receives said result data file from said computation station.

18. The computer based system of claim 17, further comprising a remote computer in communication with said communication station;
   wherein said remote computer transmits patient data to said communication station;
   wherein said communication station stores said patient data in said patient data file prior to transmitting said patient data file to said computation station; and wherein said communication station transmits said result data file received from said computation station to said remote computer.

19. The computer based system of claim 18, further comprising a second remote computer in communication with said communication station; and wherein said second remote computer receives said result data file from said computation station.

20. The computer based system of claim 1, wherein the patient biomarkers are demographic data, electrical diagnostic data, imaging diagnostic data, histologic diagnostic data, concentrations of biomarkers in a biological fluid, or a combination of these biomarkers.

21. In a networked computer environment comprising a communication station in communication with a computation station, said computation station comprising a trained neural network, a method for prognosing a disease, diagnosing a disease, determining a severity of a disease, screen for a disease, or a determine a likelihood of obtaining a disease in a patient, comprising the computer implemented steps of:

at said communication station, receiving patient data and storing said patient data in a patient data file;

at said computation station, receiving said patient data file from said communication station and introducing said patient data file into a trained neural network, wherein said trained neural network is trained with a method comprising:

preprocessing patient biomarkers, comprising:

selecting patient biomarkers associated with the disease process;

statistically and/or computationally testing discriminating power of the selected patient biomarkers individually in linear and/or non-linear combination for indicating the presence or the absence or the severity of the disease, or the likelihood of obtaining the disease;

applying statistical, mathematical, or computational tools, and/or expert knowledge for the derivation of secondary inputs to the neural network that are linear or non-linear combinations of the original or transformed biomarkers;

selecting only those patient biomarkers or derived secondary inputs that show discriminating power; and training the computer-based neural network using the preprocessed patient biomarkers or derived secondary inputs; and at said computation station, in response to said trained neural network processing said patient data file, receiving an output value from said trained neural network, said output value corresponding to the presence of the disease, the absence of the disease, the severity of the disease, or the likelihood of obtaining the disease.

22. Computer-readable media having stored thereon computer-executable instructions for performing the method of claim 21.

23. The method of claim 21, further comprising the steps of:

at said computation station, storing said output value in a result data file; and from said computation station, transmitting said result data file to said communication station.

24. The method of claim 23, wherein said networked computer environment further comprises a remote computer in communication with said communication station; and wherein the method further comprises the steps of:

at said communication station, receiving patient data from said remote computer, and from said communication station, transmitting said result data file received from said computation station to said remote computer.

25. Computer-readable media having stored thereon computer-executable instructions for performing the method of claim 24.

26. The method of claim 24, wherein said networked computer environment further comprises a first remote computer and a second remote computer in communication with said communication station; and wherein the method further comprises the steps of:

at said communication station, receiving patient data from said first remote computer, and from said communication station, transmitting said result data file received from said computation station to said second remote computer.

27. The method of claim 21, wherein said patient data comprises patient biomarkers and patient demographic data.

28. The method of claim 21, wherein said trained neural network is trained to determine the likelihood of obtaining a disease, screen for the disease, determine the severity of the disease, or diagnose or prognose the disease, wherein the disease is selected from the group consisting of osteoporosis, osteopenia, breast cancer, ovarian cancer, colon cancer, prostate cancer, and testicular cancer.

29. The method of claim 28, wherein the disease is prostate cancer and the biomarkers are patient age, LASA-P®, PAP, PSA, CK-MB, CK-MM, CK-BB or any combination of the biomarkers.

30. The method of claim 28, wherein the disease is osteoporosis and the biomarkers are patient age, serum calcium, serum phosphate, estradiol, progesterone, ALP, ALP Isoenzyme 1, ALP Isoenzyme 2, or any combination of the biomarkers.

31. The method of claim 28, wherein the disease is ovarian cancer and the biomarkers are patient age, LASA-P®, CA125, CA12511, DM/70K, MCSF, OVX1, CA7-24, CA19-9 or any combination of the biomarkers.

32. The method of claim 28, wherein the disease is breast cancer and the biomarkers are patient age, LASA-P®, CEA, CA15-3®, HER2/neu, or any combination of the biomarkers.

33. The method of claim 28, wherein the disease is testicular cancer and the biomarkers are patient age, LASA-P®, AFP, HCG-Beta, CA15-30 or any combination of the biomarkers.

34. The method of claim 28, wherein the disease is colon cancer and the biomarkers are patient age, LASA-P®, CA19.9, CEA or any combination of the biomarkers.

35. The method of claim 21, further comprising the steps of:

at said computation station, introducing said output value produced by said trained neural network into a second trained neural network, said second trained neural network producing a second output value corresponding to the presence or the absence or the severity of a disease, or the likelihood of obtaining a disease;

at said computation station, storing said second output value a result data file; and at said communication station, receiving said result data file from said computation station.

36. Computer-readable media having stored thereon computer-executable instructions for performing the method of claim 35.

37. The method of claim 21, further comprising the steps of detecting an abnormal situation during processing in said computation station; and reporting the abnormal situation through an audible signal.

38. Computer-readable media having stored thereon computer-executable instructions for performing the method of claim 37.

39. The method of claim 21, wherein the patient biomarkers are demographic data, electrical diagnostic data, imaging diagnostic data, histologic diagnostic data, and concentrations of biomarkers in a biological fluid or a combination of these biomarkers.

* * * * *